US007638122B2

(12) United States Patent
Yu et al.

(10) Patent No.: US 7,638,122 B2
(45) Date of Patent: Dec. 29, 2009

(54) STAT3 ANTAGONISTS AND THEIR USE AS VACCINES AGAINST CANCER

(75) Inventors: Hua Yu, Tampa, FL (US); Drew Pardoll, Brookeville, MD (US); Richard Jove, Tampa, FL (US)

(73) Assignees: University of South Florida, Tampa, FL (US); Johns Hopkins University, Baltimore, MD (US)

( * ) Notice: Subject to any disclaimer, the term of this patent is extended or adjusted under 35 U.S.C. 154(b) by 1062 days.

(21) Appl. No.: 10/383,707

(22) Filed: Mar. 7, 2003

(65) Prior Publication Data

US 2004/0175369 A1 Sep. 9, 2004

(51) Int. Cl.
A61K 35/12 (2006.01)
A61K 35/14 (2006.01)
A61K 41/00 (2006.01)

(52) U.S. Cl. .................. 424/93.71; 435/70.1; 435/377

(58) Field of Classification Search .................. None
See application file for complete search history.

(56) References Cited

U.S. PATENT DOCUMENTS

| 4,690,915 | A | | 9/1987 | Rosenberg |
| 4,853,380 | A | * | 8/1989 | Schwartz .................. 514/184 |
| 5,045,316 | A | | 9/1991 | Kaplan |
| 5,093,246 | A | | 3/1992 | Cech et al. |
| 5,159,694 | A | | 10/1992 | Overath et al. |
| 5,290,551 | A | * | 3/1994 | Berd .................. 424/193.1 |
| 5,716,622 | A | | 2/1998 | Darnell et al. |
| 5,731,155 | A | | 3/1998 | Schreiber et al. |
| 5,883,228 | A | | 3/1999 | Darnell, Jr. et al. |
| 5,935,993 | A | | 8/1999 | Tang et al. |
| 5,972,598 | A | | 10/1999 | Chaudhary et al. |
| 5,976,835 | A | | 11/1999 | Darnell, Jr. et al. |
| 6,130,087 | A | * | 10/2000 | Srivastava et al. ......... 435/372.3 |
| 6,159,694 | A | | 12/2000 | Karras |
| 6,235,873 | B1 | | 5/2001 | Bromberg et al. |
| 6,265,160 | B1 | | 7/2001 | Leonard |
| 6,426,366 | B1 | | 7/2002 | Novogrodsky et al. |
| 6,469,013 | B2 | | 10/2002 | Uckun et al. |
| 6,602,709 | B1 | * | 8/2003 | Albert et al. ................. 435/372 |
| 7,348,139 | B1 | * | 3/2008 | Herman et al. .................. 435/6 |
| 2002/0155108 | A1 | * | 10/2002 | Barbera-Guillem ...... 424/140.1 |
| 2004/0052762 | A1 | | 3/2004 | Yu et al. |

FOREIGN PATENT DOCUMENTS

| WO | WO97/26328 | | 7/1997 |
| WO | WO 99/28465 | | 6/1998 |
| WO | WO 98/30688 | | 7/1998 |
| WO | WO 98/41090 | | 9/1998 |
| WO | WO99/58126 | * | 11/1999 |
| WO | 00/44774 | | 8/2000 |
| WO | WO02/18572 | | 3/2002 |
| WO | WO 02/20032 | * | 3/2002 |

OTHER PUBLICATIONS

Abstract of Wheeler (Salud p'ublica de M'exico, (Jul.-Aug. 1997) 39 (4) 283-7).*
Bachman et al (Journal of Immunology, 2005, vol. 175, pp. 4677-4685).*
Todryk et al (Immunology, 2000, vol. 99, pp. 334-337).*
Efferson et al (Anticancer research, 2005, vol. 25, pp. 715-724).*
Matzinger, Annual Review of Immunology, 1994, vol. 12, pp. 991-1045.*
Bohm et al, Journal of Investigative Dermatology, 2001, vol. 117, pp. 132-140.*
Jones et al (Advanced Drug Delivery Reviews 1998, vol. 31, pp. 153-170.*
Ko et al (Food and Chemical Toxicology, 2000, vol. 38, pp. 861-865).*
Biragyn et al., "Toll-Like Receptor 4-Dependent Activation of Dendritic Cells by β-Defensin 2," *Science*, 2002, 298:1025-1029.
Bloom et al., "Identification of Tyrosinase-related Protein 2 as a Tumor Rejection Antigen for the B16 Melanoma," *J. Exp. Med.*, 1997, 185(3):453-460.
Bowman et al., "Stat3-mediated Myc expression is required for Src transformation and PDGF-induced mitogenesis," *Proc. Natl. Acad. Sci. USA*, 2001, 98(13):7319-7324.
Bowman et al., "STATs in oncogenesis," *Oncogene*, 2000, 19:2474-2488.
Bromberg and Darnell Jr., "The role of STATs in transcriptional control and their impact on cellular function," *Oncogene*, 2000, 19:2468-2473.
Bromberg et al., "Stat3 as an oncogene," *Cell*, 1999, 98(3):295-303, Erratum in *Cell*, 1999, 99(2):239, Abstract only.
Caldenhoven et al., "STAT3β, a Splice Variant of Transcription Factor STAT3, Is a Dominant Negative Regulator of Transcription," *J. Biol. Chem.*, 1996, 271(21):13221-13227.
Catlett-Falcone et al., "Constitutive activation of Stat3 signaling confers resistance to apoptosis in human U266 myeloma cells," *Immunity*, 1999, 10(1):105-115.
Celluzzi and Falo Jr., "Cutting Edge: Physical Interaction Between Dendritic Cells and Tumor Cells Results in an Immunogen That Induces Protective and Therapeutic Tumor Rejection," *J. Immunol.*, 1998, 160:3081-3085.

(Continued)

*Primary Examiner*—Karen A Canella
(74) *Attorney, Agent, or Firm*—Fish & Richardson P.C.

(57) ABSTRACT

The present invention relates to methods for treating and/or preventing cancer. In particular the present invention relates to ex vivo immunotherapeutic methods. The methods comprise decreasing Stat3 (signal transducer and activator of transcription3) expression and/or function in tumor cells and the administration of such cells to a subject in need of treatment and/or prevention. Other methods of the invention comprise activating T-cells by co-culturing the T-cells with the tumor cells with decreased Stat3 expression or function. The invention further encompasses methods comprising decreasing Stat3 expression or function in antigen-presenting cells and co-administering tumor cells and the antigen-presenting cells with decreased Stat3 function to a patient. The invention further relates to methods for stimulating dendritic cell differentiation.

12 Claims, 16 Drawing Sheets

OTHER PUBLICATIONS

Figure 1A:
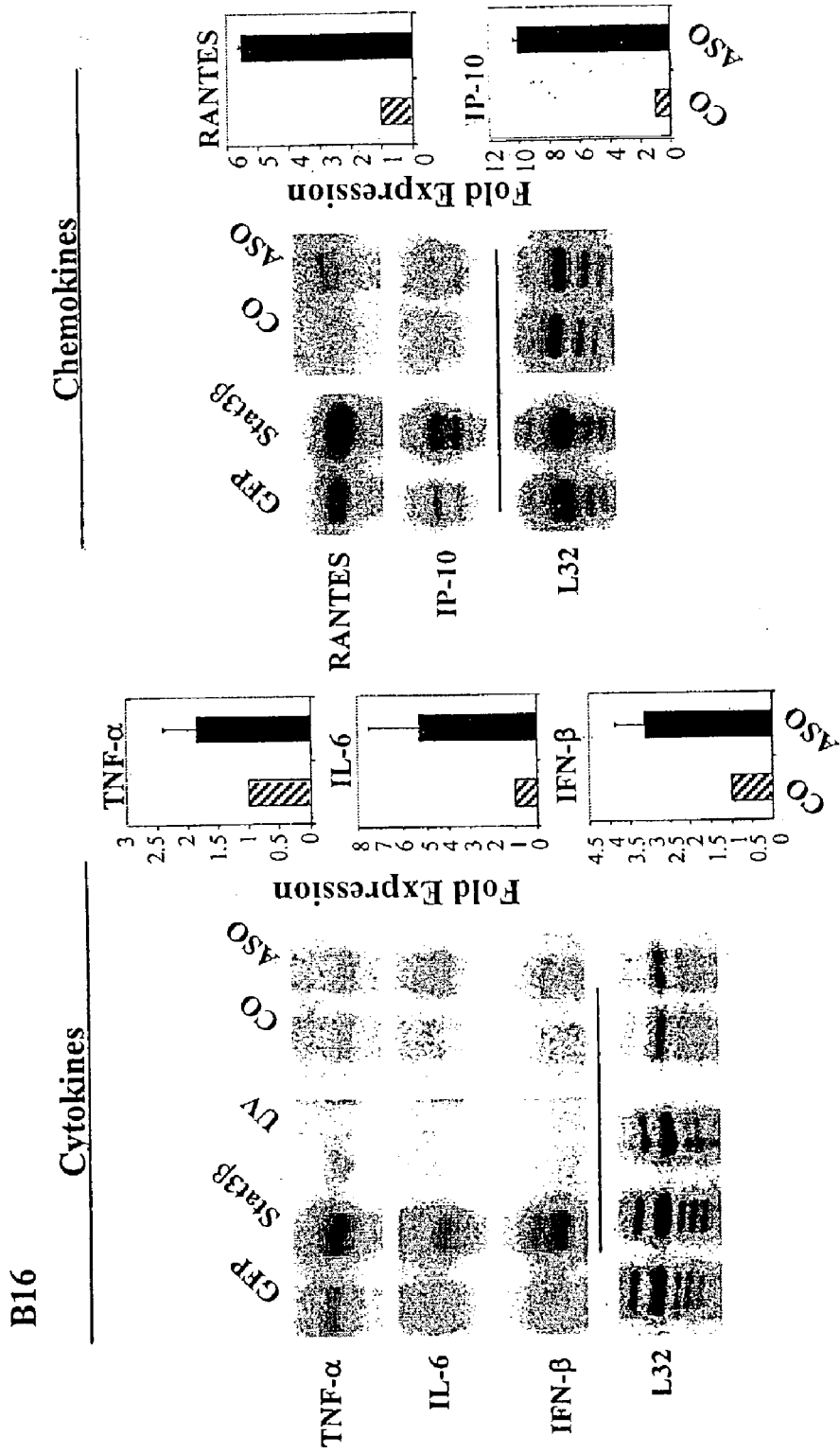

De Bruijn et al., "Peptide loading of empty major histocompatibility complex molecules on RMA-S cells allows the induction of primary cytotoxic T lymphocyte responses," *Eur. J. Immunol.*, 1991, 21(12):2963-2970.

De Bruijn et al., "Phagocyte-induced antigen-specific activation of unprimed CD8+ T cells in vitro," *Eur. J. Immunol.*, 1995, 25(5):1274-1285.

De Bruijn et al., "Mechanisms of induction of primary virus-specific cytotoxic T lymphocyte responses," *Eur. J. Immunol.*, 1992, 22(11):3013-3020.

Darnell Jr., "STATs and Gene Regulation," *Science*, 1997, 277:1630-1635.

Darnell Jr. et al., "Jak-STAT pathways and transcriptional activation in response to IFNs and other extracellular signaling proteins," *Science*, 1994, 264(5164):1415-1421.

Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci. USA*, 1993, 90:3539-3543.

Fearon and Locksley, "The instructive role of innate immunity in the acquired immune response," *Science*, 1996, 272(5258):50-53.

Fuchs and Matzinger, "Is cancer dangerous to the immune system?" *Semin. In Immunol.*, 1996, 8:271-280.

Fujii et al., "Functional dissection of the cytoplasmic subregions of the IL-2 receptor βc chain in primary lymphocyte populations," *EMBO J.*, 1998, 17(22):6551-6557.

Gabrilovich et al., "Vascular Endothelial Growth Factor Inhibits the Development of Dendritic Cells and Dramatically Affects the Differentiation of Multiple Hematopoietic Lineages In Vivo," *Blood*, 1998, 92(11):4150-4166.

Gabrilovich et al., "Production of vascular endothelial growth factor by human tumors inhibits the functional maturation of dendritic cells," *Nat. Med.*, 1996, 2(10):1096-1103, Erratum in *Nat. Med.*, 1996, 11:1267, Abstract only.

Gallucci et al., "Natural adjuvants: endogenous activators of dendritic cells," *Nat. Med.*, 1999, 5(11):1249-1255.

Gong et al., "Induction of Antitumor activity by immunization with fusions of dendritic and carcinoma cells," *Nat. Med.*, 1997, 3(5):558-561.

Grandis et al., "Constitutive activation of Stat3 signaling abrogates apoptosis in squamous cell carcinogenesis in vivo," *Proc. Natl. Acad. Sci. USA*, 97(8):4227-4232.

Greenberg, *Basic and Clinical Immunology*, 1987, 6th ed., Stites et al. (eds.), Chapter 14, pp. 186-196.

Greenberg et al., *Basic and Clinical Tumor Immunology*, 1983, Herbermann et al. (eds.), pp. 301-335.

Guo et al., "Effective tumor vaccine generated by fusion of hepatoma cells with activated B cells," *Science*, 1994, 263(5146):518-520.

Hadden, "T-cell adjuvants," *Int. J. Immunopharmacol.*, 1994, 16(9):703-710.

Han et al., "Molecular Role of TGF-β, Secreted from a New Type of CD4+ Suppressor T cell, NY4.2, in the Prevention of Autoimmune IDDM in NOD Mice," *J. Autoimmunity*, 1997, 10(3):299-307.

Houbiers et al., "In vitro induction of human cytotoxic T lymphocyte responses against peptides of mutant and wild-type p53," *Eur. J. Irnmunol.*, 1993, 23(9):2072-2077.

Inaba et al., "Direct Activation of CD8+ Cytotoxic T Lymphocytes by Dendritic Cells," *J. Exp. Med.*, 1987, 166:182-194.

Janeway Jr., "Approaching the asymptote: Evolution and revolution in immunology," *Cold Spring Harb. Symp. Quant. Biol.*, 1989, 54 Pt 1:1-13.

Kadowaki et al., "Natural Interferon α/β-producing Cells Link Innate and Adaptive Immunity," *J. Exp. Med.*, 2000, 192(2):219-225.

Kaplan et al., "Demonstration of an interferon γ-dependent tumor surveillance system in immunocompetent mice," *Proc. Natl. Acad. Sci. USA*, 1998, 95:7556-7561.

Korpelainen et al., "Endothelial receptor tyrosine kinases activate the STAT signaling pathway: mutant Tie-2 causing venous malformations signals a distinct STAT activation response," *Oncogene*, 1999, 18:1-8.

Lu et al., "CD40-independent Pathways of T Cell Help for Priming of CD8+ Cytotoxic T Lymphocytes," *J. Exp. Med.*, 2000, 191(3):541-550.

Macatonia et al., "Primary Stimulation by Dendritic Cells Induces Antiviral Proliferative and Cytotoic T Cell Responses In Vitro," *J. Exp. Med.*, 1989, 169:1255-1264.

McLemore et al., "Stat-3 Activation Is Required for Normal G-CSF-Dependent Proliferation and Granulocytic Differentiation," *Immunity*, 2001, 14:193-204.

Medzhitov and Janeway, "Innate immunity: impact on the adaptive immune response," *Curr. Opin. Immunol.*, 1997, 9(1):4-9.

Mellman and Steinman, "Dendritic Cells: Specialized and Regulated Antigen Processing Machines," *Cell*, 2001, 106:255-258.

Mule et al., "Adoptive immunotherapy of established pulmonary metastases with LAK cells and recombinant interleukin-2," *Science*, 1984, 225(4669):1487-1489.

Niu et al., "Roles of activated Src and Stat3 signaling in melanoma tumor cell growth," *Oncogene*, 2002, 21:7001-7010.

Niu et al., "Overexpression of a Dominant-Negative Signal Transducer and Activator of Transcription 3 Variant in Tumor Cells Leads to Production of soluble Factors That Induce Apoptosis and Cell Cycle Arrest," *Cancer Research*, 2001, 61:3276-3280.

Niu et al., "Gene Therapy with Dominant-negative Stat3 Suppresses Growth of the Murine Melanoma B16 Tumor in Vivo," *Cancer Research*, 1999, 59:5059-5063.

Pardoll, "Cancer vaccines," *Nat. Med.*, 1998, 4(5 Suppl.):525-531.

Rosenberg et al., "A progress report on the treatment of 157 patients with advanced cancer using lymphokine-activated killer cells and interleukin-2 or high-dose interleukin-2 alone," *N. Engl. J. Med.*, 1987, 316(15):889-897.

Rosenberg et al., "Use of tumor-infiltrating lymphocytes and interleukin-2 in the immunotherapy of patients with metastatic melanoma. A preliminary report," *N. Engl. J. Med.*, 1988, 319(25):1676-1680.

Shankaran et al., "IFNγ and lymphocytes prevent primary tumour development and shape tumour immunogenicity," *Nature*, 2001, 410:1107-1111.

Shen et al., "Constitutively activated Stat3 protects fibroblasts from serum withdrawal and UV-induced apoptosis and antagonizes the proapoptotic effects of activated Stat1," *Proc. Natl. Acad. Sci. USA*, 2001, 98(4):1543-1548.

Starr and Hilton, "Negative regulation of the JAK/STAT pathway," *Bioessays*, 1999, 21(1):47-52.

Takeda et al., "Enhanced Th1 activity and development of chronic enterocolitis in mice devoid of Stat3 in macrophages and neutrophils," *Immunity*, 1999, 10(1):39-49.

Topalian et al., "Tumor-Specific Cytolysis by Lymphocytes Infiltrating Human Melanomas," *J. Immunol.*, 1989, 142(10):3714-3725.

Turkson et al., Phosphotyrosyl Peptides Block Stat3-mediated DNA Binding Activity, Gene Regulation, and Cell Transformation, *J. Biol. Chem.*, 2001, 276(48):45443-45455.

Turkson et al., "Stat3 Activation by Src Induces Specific Gene Regulation and Is Required for Cell Transformation," *Mol. Cell. Biol.*, 1998, 18(5):2545-2552.

Udono et al., "Cellular requirements for tumor-specific immunity elicited by heat shock proteins: Tumor rejection antigen gp96 primes CD8+ T cells in vivo," *Proc. Natl. Acad. Sci. USA*, 1994, 91:3077-3081.

Urban et al., "Mechanisms of Syngeneic Tumor Rejection. Susceptibility of Host-selected Progressor Variants to Various Immunological Effector Cells," *J. Exp. Med.*, 1982, 155:557-573.

Uyttenhove et al., "Escape of Mouse Mastocytoma P815 After Nearly Complete Rejection is Due to Antigen-Loss Variants Rather Than Immunosuppression," *J. Exp. Med.*, 1983, 157:1040-1052.

Wortzel et al., "Multiple tumour-specific antigens expressed on a single tumour cell," *Nature*, 1983, 304(5922):165-167.

Yu et al., "Enhanced DNA-binding activity of a Stat3-related protein in cells transformed by the Src oncoprotein," *Science*, 1995, 269(5220):81-83.

Johnson et al., "Peptide and Protein Drug Delivery," *Encyclopedia of Controlled Drug Delivery*, vol. 2 (1999) pp. 816-833.

Wadia et al., "Transmembrane Delivery of Protein and Peptide Drugs by TAT-Mediated Transduction in the Treatment of Cancer," *Advanced Drug Delivery Reviews*, vol. 57 (2005) pp. 579-596.

Negoro S. et al. "Activation of JAK/STAT pathway transduces cytoprotective signal in rat acute myocardial infarction" *Cardiovascular Research*, 2000, 47: 797-805.

Negoro S. et al. "Activation of signal transducer and activator of transcription 3 protects cardiomyocytes from hypoxia/reoxigenation-induced oxidative stress through the upregulation of manganese superoxide dismutase" *Circulation*, 2001, 104: 979-981.

Yamaguchi-Takihara et al. "A novel role for STAT3 in cardiac remodeling" *Trends in Cardiovascular Medicine*, 2000, 10 (7):298-303.

Office Action in CA 2 261 621 dated May 6, 2008.

Office Action in U.S. Appl. No. 11/512,049 dated Jul. 10, 2008.

Examination Report in EP Appl. 00905724.1 dated Jul. 22, 2005.

European Search Report in EP07010488.0 dated Jul. 9, 2008.

"T-9142 Tyrphostin AG 490" [online]. LC Laboratories, [retrieved on Oct. 26, 2004]. Retrieved from the Internet: <URL: www.lclabs.com/PRODFILE/S-Z/T-9142.php4>.

Aftab et al., "Ras-independent transformation by v-Src," *Proc. Natl. Acad. Sci. USA*, 1997, 94:3028-3033.

Anderson et al., "Multiple myeloma: new insights and therapeutic approaches," *Hematology*, 2000, pp. 147-165.

Bowman and Jove, "STAT proteins and cancer," *Cancer Control*, 1999, 6:615-619.

Bowman et al., "Signal Transducers and Activators of Transcription: Novel Targets for Anticancer Therapeutics," *Cancer Control*, 1999, 6(5):427-435.

Burger et al., "IL-6 induced proliferation of a myeloma cell line is accompanied by activation of the JAK/STAT pathway and inhibited by tyrphostin AG490," *Ann. Hematology*, 1998, 77:S21.

Bright et al., "IL-12 induced Jak-Stat pathways in T lymphocytes: Regulation by tyrphostin," *J. Allergy Clin. Immunol*, 1997, 99(1):S287.

Campbell et al., "Constitutive activation of KAJ1 in Src transformed cells," *J. Biol. Chem.*, 1997, 272:2591-2594.

Catlett-Falcone et al., "STAT Proteins as Novel Targets for Cancer Therapy," *Curr. Opin. Oncology*, 1999, 11:490-496.

Ceresa et al., "Signal Transducer and Activator of Transcription-3 Series Phosphorylation by Insulin Is Mediated by a Ras/Raf/MEK-Dependent Pathway," *Endocrinol.*, 1997, 138:4131-4137.

Coll et al., "Antitumor activity of bax and p53 naked gene transfer in lung cancer: in vitro and in vivo analysis," *Human Gene Therapy*, 1998, 9:2063-2074.

Dalton et al., "Drug resistance in Multiple Myeloma: Approaches to circumvention," *Sem. Oncol.*, 1999, 26(Supp. 13):23-27.

De Groot et al., "STAT5 activation by BCR-Abl contributes to transformation of K562 leukemia cells," *Blood*, 1999, 94:1108-1112.

Dudley et al., "A Synthetic Inhibitor of the Mitogen-activated Protein Kinase Cascade," *Proc. Natl. Acad. Sci USA*, 1995, 92:7686-7689.

Eck et al., "Gene-Based Therapy," *The Pharmacological Basis of Therapeutics*, 1996, pp. 77-101.

Fan et al., "Dual Leucine Zipper-bearing Kinase (DLK) Activates p46SAPK and p38mapk but not ERK2," *J. Biol. Chem.*, 1996, 271:24788-24793.

Fanger et al., "MEKKs, GCKs, MLKs, PAKs, TAKs, and tpls: Upstream Regulators of the c-Jun Amino-terminal Kinases," *Curr. Opin. Genet. Dev.*, 1997, 7:67-74.

Frank et al., "Bystander effect in the adenovirus-mediated wild-type p53 gene therapy model of human squamous cell carcinoma of the head and neck," *Clin. Cancer Res.*, 1998, 4:2521-2528.

Frank et al., "B Lymphocytes from Patients with Chromic Lymphocytic Leukemia Contain Signal Transducer and Activator of Transcription (STAT) 1 and STAT3 Constitutively Phosphorylated on Serine Residues," *J. Clin. Invest.*, 1997, 100:3140-3148.

Fujio et al., "Signals Through gp130 Upregulate bcl-x Gene Expression Via STAT 1-binding cis-Element in Cardiac Myocytes," *J. Clin. Invest.*, 1997, 99:2898-2905.

Fukada et al., "Two Signals Are Necessary for Cell Proliferation Induced by a Cytokine Receptor gp130: Involvement of STAT3 in Anti-apoptosis," *Immunity*, 1996, 5:449-460.

Garcia et al., "Constitutive activation of Stat3 by the Src and JAK tyrosine kinases participates in growth regulation of human breast carcinoma cells," *Oncogene*, 2001, 20:2499-2513.

Garcia et al., "Constitutive activation of Stat3 in fibroblasts transformed by diverse oncoproteins and in breast carcinoma cells," *Cell Growth Differentiation*, 1997, 8:1267-1276.

Garcia and Jove, "Activation of STAT Transcription Factors in Oncogenic Tyrosine Kinase Signaling," *J. Biomed. Sci.*, 1998, 5:79-85.

Gollob et al., "The Functional Synergy Between IL-12 and IL-2 Involves p38 Mitogen-Activated Protein Kinase and Is Associated with the Augmentation of STAT Serine Phosphorylation," *J. Immunol.*, 1999, 162:4472-4481.

Gordon, "Use of vanadate as protein-phosphotyrosine phosphatase inhibitor," *Meth. Enzymol.*, 1991, 477-482.

Grandis et al., "Requirement of STAT3 but not STAT1 Activation for Epidermal Growth Factor Receptor-mediated Cell Growth In Vivo," *J. Clin. Invest.*, 1999, 102(7):1385-1392.

Grigorieva et al., "Constitutively Activated Stat3 in Myeloma Cells," *Blood*, 1996, 10:104A.

Grillot et al., "Genomic Organization, Promoter Region Analysis and chromosome localization of the mouse bcl-x gene," *J. Immunol.*, 1997, 158:4750-4757.

Han et al., "Preferential inhibition of glioblastoma cells with wild-type epidermal growth factor receptors by a novel tyrosine kinase inhibitor ethyl-2,5-dihydroxycinnamate," *Oncol. Res.*, 1997, 9:581-587.

Han et al., "Tyrphostin AG 1478 preferentially inhibits human glioma cells expressing truncated rather than wild-type epidermal growth factor receptors," *Cancer Res.*, 1996, 56(17):3859-3861.

Heller et al., "Treatment of cutaneous and subcutaneous tumors with electrochemotherapy using intralesional bleomycin," *Cancer*, 1998, 83:148-157.

Horvath et al., "A STAT Protein Domain that Determines DNA Sequence Recognition Suggests a Novel DNA-binding Domain," *Genes Dev.*, 1995, 9:984-994.

Ihle and Kerr, "JAKs and STATSs in Signaling by the Cytokine Receptor Superfamily," *Trends in Genetics*, 1995, 11:69-74.

Johnson et al., "Overexpressed pp60c-src can induce focus formation without complete transformation of NIH 3T3 cells," *Mol. Cell. Biol.*, 1985, 5:1073-1083.

Jove et al., "Preface: STAT signaling," *Oncogene*, 2000, 19:2466-2467.

Kelekar et al., "Bad Is a BH3 Domain-Containing Protein That Forms an Inactivating Dimer with Bcl-xl," *Mol. Cell. Biol.*, 1997, 17:7040-7046.

Keller and Erschler, "Effect of IL-6 receptor antisense oligodeoxynucleotide on in vitro proliferation of myeloma cells," *J. Immunol.*, 1995, 154:4091-4098.

Khosravi-Far et al., "Activation of Rac1, RhoA, and mitogen-activated protein kinases is required for Ras transformation," *Mol. Cell. Biol.*, 1995, 15:6443-6453.

Landowski et al., "Mutations in the Fas Antigen in Patients With Multiple Myeloma," *Blood*, 1997, 90:4266-4270.

Lei et al., "Enhancement of chemosensitivity and programmed cell death by tyrosine kinase inhibitors correlates with EGFR expression in non-small cell lung cancer cells," *Anticancer Research*, 1999, 19:221-228.

Liang et al., "Chemosensitization of glioblastoma cells to bis-dichloroethyl-nitrosourea with tyrphostin AG17," *Clin. Cancer Res.*, 1998, 4(3):773-781.

Liu et al., "Constitutive activation of the Jak2/Stat5 signal transduction pathway in growth factor-independent megakaryocytic leukemic cell lines," *Blood*, 1999, 93:2369-2379.

Lund et al., "The Src family kinase Lck can induce STAT3 phosphorylation and DNA-binding activity," *Cell Signal*, 1999, 11:789-796.

Lund et al., "Activation of STAT transcription factors by Herpesvirus Saimiri Tip-484 requires p56Lck," *J. Virol.*, 1997, 71:6677-6682.

Meydan et al, "Inhibition of acute lymphoblastic leukemia by a Jak-2 inhibitor," *Nature*, 1996, 379(6566):645-648.

Nakajima et al., "A central role for Stat3 in IL-6-induced regulation of growth and differentiation in M1 leukemia cells," *EMBO J.*, 1996, 15:3651-3658.

Nelson et al., "Activation of STAT3 by the c-Fes protein tyrosin kinase," *J. Biol. Chem.*, 1998, 273:7072-7077.

Nieborowska-Skorska et al., "Signal Transducer and Activator of Transcription (STAT) 5 Activation by BCR/ABL Is Dependent on Intact Src Homology (SH)3 and SH2 Domains of BCR/ABL and Is Required for Leukemogenesis," *J. Exp. Med.*, 1999, 189(8):1229-1242.

Nielsen et al., "Constitutive activation of a slowly migrating isoform of Stat3 in mycosis fungoides: tyrphostin AG490 inhibits Stat3 activation and growth of mycosis fungoides tumor cell lines," *Proc. Natl. Acad. Sci. USA*, 1997, 94:6764-6769.

Okabe et al., "In vivo antitumor activity of herbimycin A, a tyrosine kinase inhibitor, targeted against BCR/ABL oncoprotein in mice bearing BCR/ABL-transfected cells," *Leukemia Research*, 1994, 18:867-873.

Orkin et al., "Report and Recommendation of the Panel to Assess the NIH Investment in Research on Gene Therapy," *NIH*, 1995.

Palumbo et al., "The tyrphostin AG17 induces apoptosis and inhibition of cdk2 activity in a lymphoma cell line that overexpresses bcl-2," *Cancer Research*, 1997, 57:2434-2439.

Penar et al, "Inhibition of epidermal growth factor receptor-associated tyrosine kinase blocks glioblastoma invasion of the brain," *Neurosurgery*, 1997, 40:141-151.

Pumiglia et al., "Raf-1 N-Terminal Sequences Necessary for Ras-Raf Interaction and Signal Transduction," *Mol. Cell. Biol.*, 1995, 15:398-406.

Sartor et al., "Role of EGF receptor and STAT3 activation in autonomous proliferation of SUM-102PT human breast cancer cells," *Cancer Res.*, 1997, 57:978-987.

Sasse et al., "Mutational Analysis of Acute-Phase Response Factor/Stat3 Activation and Dimerization," *Mol. Cell. Biol.*, 1997, 17(8):4677-4686.

Schwab et al., "Characterization of an interleukin-6-mediated autocrine growth loop in the human multiple myeloma cell line, U266," *Blood*, 1991, 77:587-593.

Scott and Smith, "Searching for Peptide Ligands With an Epitope Library," *Science*, 1990, 249:306-390.

Sinibaldi et al., "Induction of p21 AF1/CIP1 and cyclin D1 expression by the Src oncoprotein in mouse fibroblasts: role of activated STAT3 signaling," *Oncogene*, 2000, 19:5419-5427.

Sporeno et al., "Human Interleukin-6 Receptor Super-antagonists with High Potency and Wide Spectrum on Multiple Myeloma Cells," *Blood*, 1996, 87:4510-4519.

Tan et al., "Injection of complementary DNA encoding interleukin-12 inhibits tumor establishment at a distant site in a murine renal carcinoma model," *Cancer Res.*, 1996, 56:3399-3403.

Tsai et al., "Enhancement of chemosensitivity by tyrphostin AG825 in high-p185-neu expressing non-small cell lung cancer cells," *Cancer Research*, 1996, 56:1068-1074.

Turkson et al., "Requirement for Ras/Racl-Mediated p38 and c-Jun N-Terminal Kinase Signaling in Stat3 Transcriptional Activity Induced by the Src Oncoprotein," *Mol. Cell. Biol.*, 1999, 19:7519-7528.

Turkson and Jove, "STAT proteins: novel molecular targets for cancer drug discovery," *Oncogene*, 2000, 19:6613-6626.

Verma et al., "Gene therapy—promises, problems and prospects," *Nature*, 1997, 389:239-242.

Wagner et al., "The SIF binding element confers sis/PDGF inducibility onto the c-fos promoter," *EMBO J.*, 1990, 9:4477-4484.

Wang et al., "Activation of Stat3 preassmbled with platelet-derived growth factor-beta receptors requires Src kinase activity," *Oncogene*, 2000, 19:2075-2085.

Wasik et al., "Suppression of proliferation and phosphorylation of Jak3 and STAT5 in malignant T-cell lymphoma cells by derivatives of octylamino-undecyl-dimethylxanthine," *Leukemia and Lymphoma*, 1998, 28:551-560.

Whalen et al., "Megakaryocytic differentiation induced by constitutive activation of mitogen-activated protein kinase kinase," *Mol. Cell. Biol.*, 1997, 17:1947-1958.

Whitmarsh et al., "A Mammalian Scaffold Complex that Selectively Mediates MAP Kinase Activation," *Science*, 1998, 281:1671-1674.

Yu et al., "Constitutive activation of the JAK-STAT pathway in T lymphoma overexpressing the Lck protein tyrosine kinase," *J. Immunol.*, 1997, 159:5206-5210.

Zhang et al., "Activation of Stat3 in v-Src transformed fibroblasts requires cooperation of Jak1 kinase activity," *J. Biol. Chem.*, 2000, 275:24935-24944.

Zong et al., "Unique Signal Transduction of Eyk: Constitutive Stimulation of JAK-STAT Pathway by an Oncogenic Receptor-type Tyrosine Kinase," *EMBO J.*, 1996, 15:4515-4525.

Zushi et al., "STAT3 mediates the survival signal in oncogenic ras-transfected intestinal epithelial cells," *Int. J. Cancer*, 1998, 78(3):326-330.

Zushi et al., "Role of heparin-binding EGF-related peptides in proliferation and apoptosis of activated ras-stimulated intestinal epithelial cells," *Int. J. Cancer*, 1997, 73(6):917-923.

WIPO Authorized Officer Nora Lindner, International Preliminary Report on Patentability in PCT/US2004/006783 mailed Mar. 5, 2009, 9 pages.

EPO Examination Report in EP 01 970 740.5 mailed Oct. 20, 2008, 4 pages.

\* cited by examiner

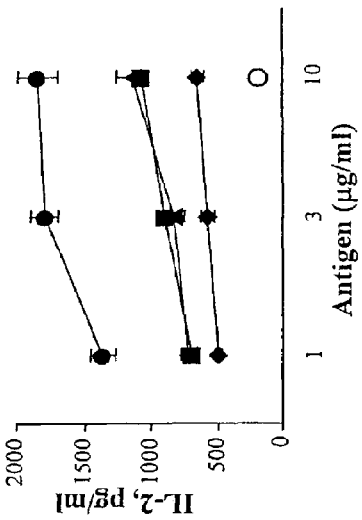
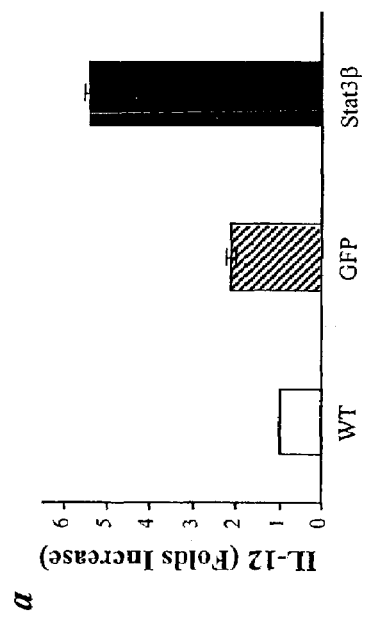
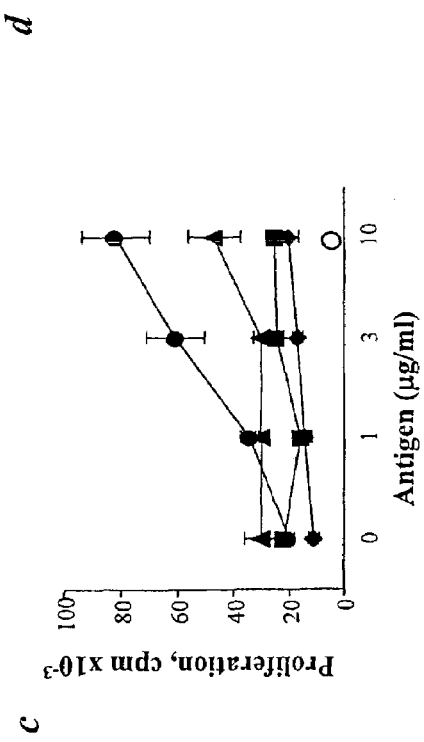
FIG. 4A
FIG. 4B
FIG. 4C
FIG. 4D

*a*     Anti-CD3e

*b*

STAT3 ANTAGONISTS AND THEIR USE AS VACCINES AGAINST CANCER

The development of this invention was supported by grant numbers CA75243, CA55652 and CA77859 awarded by the National Institutes of Health. The Government has certain rights in this invention.

1. INTRODUCTION

The present invention relates to methods for treating and/or preventing cancer. In particular the present invention relates to ex vivo immunotherapeutic methods. The methods comprise decreasing Stat3 (signal transducer and activator of transcription3) expression and/or function in tumor cells and the administration of such cells to a subject in need of treatment and/or prevention. Other methods of the invention comprise activating T-cells by co-culturing the T-cells with the tumor cells with decreased Stat3 expression or function. The invention further encompasses methods comprising decreasing Stat3 expression or function in antigen-presenting cells and co-administering tumor cells and the antigen-presenting cells with decreased Stat3 function to a patient. The invention further relates to methods for stimulating dendritic cell differentiation.

2. BACKGROUND OF THE INVENTION

Signal transducers and activators of transcription (STATs) are latent cytoplasmic transcription factors that function as intracellular effectors of cytokine and growth factor signaling pathways (Darnell, 1997, Science 277(5332):1630-1635). STAT proteins were originally defined in the context of normal cell signaling where STATs have been implicated in control of cell proliferation, differentiation, and apoptosis (Bromberg and Darnell, 2000, Oncogene, 19:2468-2473; Darnell et al., 1994, Science 264:1415-1421).

Stat3β is a truncated form of Stat3 that contains the dimerization and DNA binding domain but lacks the transactivation domain (Catlett-Falcone et al., 1999, Immunity, 10:105-115). As a consequence, Stat3β can bind DNA but cannot transactivate gene expression, thus blocking Stat3 signaling in a trans-dominant negative fashion in most cases. Blocking Stat3 by Stat3β in U266 cells, which are cells that are inherently resistant to Fas-mediated apoptosis and express high levels of the antiapoptotic protein Bcl-x L, down-regulated expression of the Stat3-regulated $BCl-X_L$ gene, resulting in a dramatic sensitization of cells to Fas-mediated apoptosis in vitro (Catlett-Falcone et al., 1999, supra).

Recent studies in genetically-deficient mice demonstrate that multiple components of both the innate and adaptive immune system can act as extrinsic tumor suppressors (Kaplan et al., 1998, Immunology 95:7556-7561; Shankaran et al., 2001, Nature 410: 1107). Indeed, tissue disruption, such as that associated with invasion and metastatic spread of cancer, can stimulate pro-inflammatory signals similar to pathogen infection, which activate antigen presenting cells, leading to antigen-specific immune responses. However, the immune system is generally tolerant to established cancers (Fuchs and Matzinger, 1996, Semin. in Immunol. 8:271-280; Pardoll, 1998, Nat Med 4:525-531), suggesting that cancers can develop mechanisms to inhibit production of and/or sensing of immunologic danger signals.

Stat3 is a negative regulator of inflammatory responses, as mice devoid of the Stat3 gene in macrophages and neutrophils produce elevated levels of pro-inflammatory cytokines upon lipopolysaccharide (LPS). induced stimulation of the immune system, leading to development of chronic enterocolitis (Takeda et al, 1999, Immunity 10:39-49). Stat3 is a common point of convergence for oncogenic tyrosine kinases, and constitutively-activated Stat3 enhances tumor cell proliferation and prevents apoptosis (Catlett-Falcone, 1999, Immunity 10:105-115; Grandis et al., 2000, Proc Natl Acad Sci 97:4227-4232; Bromberg et al., 1999, Cell 98:295-303; Bowman et al., 2001, Proc Natl Acad. Sci 98:7319-7324).

2.1 The Immune Response

Cells of the immune system arise from pluripotent stem cells through two main lines of differentiation, the lymphoid lineage and the myeloid lineage. The lymphoid lineage produces lymphocytes, such as T cells, B cells, and natural killer cells, while the myeloid lineage produces monocytes, macrophages, and neutrophils and other accessory cells, such as dendritic cells, platelets, and mast cells. Lymphocytes circulate and search for invading foreign pathogens and antigens that tend to become trapped in secondary lymphoid organs, such as the spleen and the lymph nodes, where such antigens are taken up by antigen-presenting cells (APCs). The interaction between T cells and APCs triggers several effector pathways, including activation of cytotoxic T lymphocytes (CTLs) and stimulation of T cell production of cytokines. CTLs then kill target cells that carry the same class I MHC molecule and the same antigen that originally induced their activation.

2.2 Antigen Presentation

Major histocompatibility complex (MHC) molecules present antigens on the cell surface of antigen-presenting cells. Cytotoxic T lymphocytes then recognize MHC molecules and their associated peptides and kill the target cell. Antigens are processed by two distinct routes depending upon whether their origin is intracellular or extracellular. Intracellular or endogenous protein antigens, i.e., antigens synthesized within the antigen-presenting cell, are presented by class I MHC molecules to $CD8^+$ cytotoxic T lymphocytes. $CD8^+$ CTLs are antigen-specific effector cells derived from pluripotent stem cells via the lymphoid lineage that are important in resisting pathogens, cancer and allograft rejection, and are expressed in most cell types (Terstappen et al., 1992, Blood 79:666-677). On the other hand, extracellular antigenic determinants are presented on the cell surface of "specialized" or "professional" APCs (macrophages, for example) by class II MHC molecules to $CD4^+$ "helper" T cells (see generally, W. E. Paul, ed., Fundamental Immunology. New York: Raven Press, 1984).

Class I and class II MHC molecules are the most polymorphic proteins known. A further degree of heterogeneity of MHC molecules is generated by the combination of class I and class II MHC molecules, known as the MHC haplotype. In humans, HLA-A, HLA-B and HLA-C, three distinct genetic loci located on a single chromosome, encode class I molecules. Because T cell receptors specifically bind complexes comprising antigenic peptides and the polymorphic portion of MHC molecules, T cells respond poorly when an MHC molecule of a different genetic type is encountered. This specificity results in the phenomenon of MHC-restricted T cell recognition and T cell cytotoxicity.

The process of presenting an antigen to T cells involves antigen capture by an APC, either by binding to a receptor or by uptake in the fluid phase. This is followed by proteolytic degradation of the antigen, and formation of a complex between the antigenic peptide and an MHC molecule within the APC (Lanzavecchia, 1996, Curr. Opin. Immunol. 8:348-354). In pathogen-infected cells, proteins of the pathogen are degraded inside the cells, and some of the resulting peptides are transported into the lumen of the endoplasmic reticulum where they form complexes with class I MHC molecules. Additionally, antigens can be chaperoned by heat shock proteins into an endogenous pathway whereby antigenic peptides become associated with class I MHC molecules (Suto et al., 1995, Science 269:1585-1588; Srivastava et al., 1994, Immunogenetics 39:93-98). These class I MHC protein—peptide complexes are then transported to and accumulate on the cell surfaces, where they are recognized by receptors on T cells (Yewdell et al., 1992, Adv. Immunol. 52:1-123; Bevan, 1995, J. Exp. Med. 182:639-641).

Cytotoxic T lymphocytes and helper T cells develop and undergo selection in the thymus. These cells are distinguished by the presence of one of two surface markers, CD4 (helper T cells) or CD8 (CTLs). These lymphocytes circulate in the periphery and become "primed" in the lymphoid organs on encountering the appropriate signals defined by the two signal model originally proposed for B cells (Bretscher & Cohn, 1970, Science 169:1042-1049). The first signal is received through the T cell receptor after it engages antigenic peptides complexed with class I MHC molecules on the surface of APCs. The second signal is provided either by a secreted chemical signal or cytokine, such as interleukin-1 (IL-1), or by a plasma-membrane-bound costimulatory molecule, such as B7. Cytokines, such as interferon-γ, interleukin-2 (IL-2), interleukin-4 (IL-4), interleukin-7 (IL-7), and interleukin-12 (IL-12), produced by $CD4^+$ helper T cells, are required.

Helper T cells receiving both signals are activated to proliferate and to secrete a variety of interleukins. CTLs receiving both signals are activated to kill target antigenic cells. However, T cells receiving the first signal in the absence of costimulation become anergized, leading to tolerance (Lamb et al., 1983, J. Exp. Med. 157:1434-1447; Mueller et al., 1989, Annu. Rev. Immunol. 7:445-480; Schwartz, 1992, Cell 71:1065-1068; Mueller and Jenkins, 1995, Curr. Opin. Immunol. 7:375-381).

Cell surface receptor molecules, such as B7, present on the antigen-presenting cell embrane, are recognized by a coreceptor on the cell surface of helper T cells, called CD28, a member of the Ig superfamily. In addition to antigen-specific interactions during antigen presentation, antigen non-specific adhesive mechanisms also operate. These stabilize the binding of T lymphocytes to APC. Receptor molecules on APC, such as ICAM-1/CD54, LFA-3/CD58, and B7, bind corresponding co-receptors on T cells.

2.3 Adoptive Immunotherapy

The cytotoxic T cell response is the most important host response for the control of growth of antigenic tumor cells (Anichimi et al., 1987, Immunol. Today 8:385-389). Studies with experimental animal tumors as well as spontaneous human tumors have demonstrated that many tumors express antigens that can induce an immune response. Some antigens are unique to the tumor, and some are found on both tumor and normal cells. Several factors influence the immunogenicity of the tumor, including, for example, the specific type of carcinogen involved, and immunocompetence of the host and the latency period (Old et al., 1962, Ann. N.Y. Acad. Sci. 101:80-106; Bartlett, 1972, J. Natl. Cancer. Inst. 49:493-504). It has been demonstrated that T cell-mediated immunity is of critical importance for rejection of virally and chemically induced tumors (Klein et al., 1960, Cancer Res. 20:1561-1572; Tevethia et al., 1974, J. Immunol. 13:1417-1423).

Adoptive immunotherapy for tumors refers to the therapeutic approach wherein immune cells with antitumor reactivity are administered to a tumor-bearing host, with the objective that the cells cause the regression of an established tumor, either directly or indirectly. Immunization of hosts bearing established tumors with tumor cells or tumor antigens has generally been ineffective since the tumor may have already elicited an immunosuppressive response (Greenberg, 1987, Chapter 14, in Basic and Clinical Immunology, 6th ed., ed. by Stites, Stobo and Wells, Appleton and Lange, pp. 186-196). Thus, prior to immunotherapy, it had been necessary to reduce the tumor mass and deplete all the T cells in the tumor-bearing host (Greenberg et al., 1983, page 301-335, in Basic and Clinical Tumor Immunology, ed. Herbermann R R, Martinus Nijhoff).

Animal models have been developed in which hosts bearing advanced tumors can be treated by the transfer of tumor-specific syngeneic T cells (Mulé et al., 1984, Science 225: 1487-1489). Investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg et al., 1988, N. Engl. J. Med., 319:1676-1680). For example, TIL expanded in vitro in the presence of IL-2 have been adoptively transferred to cancer patients, resulting in tumor regression in select patients with metastatic melanoma. Melanoma TIL grown in IL-2 have been identified as $CD3^+$ activated T lymphocytes, which are predominantly CD8+ cells with unique in vitro anti-tumor properties. Many long-term melanoma TIL cultures lyse autologous tumors in a specific class I MHC- and T cell antigen receptor-dependent manner (Topalian et al., 1989, J. Immunol. 142:3714).

Application of these methods for treatment of human cancers would entail isolating a specific set of tumor-reactive lymphocytes present in a patient, expanding these cells to large numbers in vitro, and then putting these cells back into the host by multiple infusions. Since T cells expanded in the presence of IL-2 are dependent upon IL-2 for survival, infusion of IL-2 after cell transfer prolongs the survival and augments the therapeutic efficacy of cultured T cells (Rosenberg et al., 1987, N. Engl. J. Med. 316:889-897). However, the toxicity of the high-dose IL-2 and activated lymphocyte treatment has been considerable, including high fevers, hypotension, damage to the endothelial wall due to capillary leak syndrome, and various adverse cardiac events such as arrhythmias and myocardial infarction (Rosenberg et al., 1988, N. Engl. J. Med. 319:1676-1680). Furthermore, the demanding technical expertise required to generate TILs, the quantity of material needed, and the severe adverse side effects limit the use of these techniques to specialized treatment centers.

Antigen-specific CTL can be primed in vivo by immunization of animals with antigen-expressing cells, or with the antigen plus selected adjuvants (Udono et al., 1994, Proc. Natl. Acad. Sci. U.S.A. 91:3077-3081; Hadden, 1994, Int. J. Immunopharmacol. 16:703-710).

CTLs specific for class I MHC—peptide complexes could be used in treatment of cancer and viral infections, and ways have been sought to generate them in vitro without the requirement for priming in vivo. These include the use of dendritic cells pulsed with appropriate antigens (Inaba et al., 1987, J. Exp. Med. 166:182-194; Macatonia et al., 1989, J. Exp. Med. 169:1255-1264; De Bruijn et al., 1992, Eur. J. Immunol. 22:3013-3020). RMA-S cells (mutant cells expressing high numbers of 'empty' cell surface class I MHC molecules) loaded with peptide (De Bruijn et al., 1991, Eur. J. Immunol. 21:2963-2970; De Bruijn et al., 1992, supra; Houbiers et al., 1993, Eur. J. Immunol. 26:2072-2077) and macrophage phagocytosed-peptide loaded beads (De Bruijn et al., 1995, Eur. J. Immunol. 25, 1274-1285). Fusion of B cells or dendritic cells with tumor cells has been previously demonstrated to elicit anti-tumor immune responses but not T cell priming in vitro (Guo et al., 1994, Science, 263:518-520; Gong et al., 1997, Nat. Med. 3:558-561; Celluzzi, 1998, J. Immunol. 160:3081-3085).

Although tumor progression involves processes such as tissue invasion that can activate inflammatory responses, the immune system largely ignores or tolerates disseminated cancers. This implies that successful tumors must develop specific mechanisms to evade immune surveillance. While much effort has been focused on how tumors resist killing by effector T cells, little is known about mechanisms that block initiation of immune responses during transformation and malignant progression.

Citation or discussion of a reference herein shall not be construed as an admission that such is prior art to the present invention.

3. SUMMARY OF THE INVENTION

The invention relates to ex vivo immunotherapeutic methods for treating and/or preventing cancer and neoplastic disease. The methods of the invention comprise decreasing Stat3 expression and/or function in tumor cells and/or antigen presenting cells.

The invention relates to methods that comprise decreasing Stat3 expression and/or function in tumor cells ex vivo, inactivating the tumor cells to prevent further cell division of the tumor cells and using the inactivated tumor cells as a vaccine against cancer.

The invention further relates to methods comprising decreasing Stat3 function in tumor cells ex vivo and using them to activate T cells in vitro. In these embodiments, the tumor cells with decreased Stat3 function are co-cultured with T-cells to activate the T-cells. In certain embodiments, antigen-presenting cells are also present in the culture. The activated T-cells are subsequently used as a vaccine to treat or prevent a cancer or a neoplastic disease.

The invention further relates to a method involving activating T cells with antigen-presenting cells. These methods comprise decreasing Stat3 expression and/or function in tumor cells and culturing the tumor cells with decreased Stat3 expression and/or function. Subsequently, antigen-presenting cells are exposed to supernatant derived from the culture of tumor cells with decreased Stat3 function. The antigen-presenting cells that were exposed to supernatant derived from tumor cells with decreased Stat3 expression and/or function are subsequently incubated with T cells to activate the T cells. The T cells are then administered to a patient in need of prevention or treatment of a cancer or a neoplastic disease.

In another embodiment, the invention comprises methods for decreasing Stat3 expression and/or function in antigen-presenting cells. The antigen-presenting cells so treated are then mixed with tumor cells that have been treated to prevent further cell division are then co-administered to a subject to stimulate the immune-response in the subject. In certain other embodiments, the antigen-presenting cells with decreased Stat3 expression and/or function are then mixed with molecules that display the antigenicity of a tumor, and then co-administered to a subject to stimulate the immune-response in the subject. Molecules that display the antigenicity of a tumor cell can be, but are not limited to, peptides, glycoproteins, glycopeptides, or RNA molecules and DNA molecules. In even other embodiments, the antigen-presenting cells with decreased Stat3 expression and/or function of the invention are mixed with molecules displaying the antigenecity of an infectious agent, or cells displaying such an antigenic molecule, or with an infectious agent that has been modified such that it does not cause disease in a subject, and then co-administered to a subject to stimulate the immune-response in the subject. In a particular embodiment, the infectious agent is a virus or a bacterium. A molecule displaying the antigenicity of the infectious agent can be a, but is not limited to, a peptide, a glycoprotein, a glycopeptide, a RNA molecule and a DNA molecule.

The invention also encompasses methods for stimulating dendritic cell differentiation. The methods comprise antagonizing Stat3 expression and/or function in tumor cells and culturing the tumor cells with decreased Stat3 expression and/or function. Supernatant derived from the culture of tumor cells with decreased Stat3 expression and/or function is then used to treat dendritic cells. The differentiated dendritic cells can then be administered to a patient to augment the patient's immune response.

The methods of the invention can be used to treat and/or prevent a tumor, cancer and/or neoplastic disease. In certain embodiments, the methods of the invention are used to inhibit or reduce the growth of a cancer or a neoplastic cell in a patient. In certain embodiments, the methods of the invention are used to stimulate or to augment the immune response in a patient against the cancer or the neoplastic disease that is to be treated in the patient.

As used herein, the term "Stat3 expression" refers to Stat3 gene or protein expression. Thus, methods for inhibiting or decreasing Stat3 expression may be use to inhibit or decrease the expression of the Stat3 gene or protein.

As used herein, the term "Stat3 function" refers to one or more Stat3 activities. Thus, "decreasing Stat3 function" means reducing or eliminating one or more Stat3 activities. Such stat3 activities include, but are not limited to, protein dimerization, nuclear transport, transactivation activity, nuclear transport, DNA binding activity, signal transduction and/or downstream effectors in the Stat3 signaling pathway.

The following abbreviations are used herein:

| | Abbreviation |
|---|---|
| IL-12 | Interleukin-12 |
| MHC II | Class II Major Histocompatibility Complexe |
| IRE | Insulin Response Element |
| GFP | Green Fluorescence Protein |
| PAGE | Polyacrylamide Gel Electrophoresis |
| GM-CSF | Granulocyte-macrophage-colony Stimulating Factor |
| PBS | Phosphate Buffered Saline |
| LPS | Lipopolysaccharide |
| IFN | Interferon |
| NO | Nitric Oxide |
| iNOS | Inducible NO Synthase Isoform |
| L-NMA | N-Methyl-L-Arginine |
| IPPITU | S-isopropylisothiourea |
| EITU | S-ethylisothiourea |
| MITU | S-methylisothiourea |
| AEITU | S-(2-aminoethyl)isothiourea |
| RPA | RNAse Protection Assay |
| DCs | Dendritic Cells |
| s.c. | subcutaneously |

4. BRIEF DESCRIPTION OF THE FIGURES

FIG. 1. Interrupting Stat3 signaling in tumor cellsleads to increased pro-inflammatory cytokine and chemokine RNA expression. a, Total RNA isolated from B16 tumor cells transfected with the vector control (GFP), Stat3β, control oligonucleotides (CO), or Stat3 anti-sense oligonucleotides (ASO) or exposed to apoptosis-inducing doses of UV irradiation was analyzed by RPA. Data is presented as fold-CO transfected B16 cells (arbitrary units quantified using ImageQuant Software). b, c, RPA analysis of RNA from CT26 cells expressing vector control or Stat3β (b) and SCK-1 cells transfected with CO or ASO (c). d, Microarray of Human melanoma cell line A2058 transfected with Stat3β-GFP vectors or GFP control vector. Increases in proinflammatory cytokine expression and activation of the interferon pathway were assayed compared to non treated cells as well as expression of RANTES, IP-10, IL-8, and L32.

FIG. 2. Constitutive Stat3 activity inhibits induced interleukin-6 and RANTES RNA expression in Balb/c 3T3 fibroblasts. a, Transformation of 3T3 fibroblasts by v-Src, which signals through Stat3, inhibits IFNγ and LPS-induced RNA expression of IL-6 and RANTES. Data is presented as percent RNA expression from IFNγ and LPS stimulated 3T3/c (wt) cells normalized to untreated controls. Right panel: EMSA demonstrates increased Stat3 DNA-binding in v-Src expressing 3T3 cells as compared to control cells. b, Enforced expression of the constitutively-activated Stat3 protein, Stat3C, suppresses IFNγ and LPS-induced RNA expression of IL-6 and RANTES. Data presented as in (a). Right panel: EMSA demonstrates increased Stat3 DNA-binding in Stat3C transfected 3T3/c cells as compared to control pcDNA transfected cells.

FIG. 3. Soluble factors elaborated by Stat3-interrupted tumor cells stimulate peritoneal macrophages and neutrophils. a, Soluble factors produced by Stat3β-transfected B16 cells stimulate macrophage to express CD86. b, Expression of RANTES in macrophages was up-regulated by soluble factors produced by Stat3β-transfected B16 cells as determined by RPA (insert). c, Neutrophils incubated with soluble factors produced by Stat3β-transfected B16 cells secreted elevated levels of TNF-a as determined by ELISA, n=3. d, e, Tissue sections of B16 tumors treated with either an empty vector (GFP) or the Stat3β-expression vector were stained with Mac-3 antibody for detection of macrophages (d); Giemsa for neutrophils (e). ). f, Tissue sections of SCK-1 tumors treated with either control (CO) or anti-sense oligonucleotide (ASO).

FIG. 4. The pro-inflammatory mediators secreted by Stat3-interrupted tumor cells activate relatively mature DCs, which in turn activate antigen-specific CD4+ T cells in vitro. a, ELISA showing IL-12 production by mature DC incubated in various supernatants, as indicated; n=3. b, The mean florescent intensity (MFI) of each surface marker in DCs cultured in medium without any tumor supernatants was assigned one: wt(open bar); GFP (striped bar); Stat3β (closed bar). c, d, Purified CD4+ T cells derived from transgenic mouse with HA-specific CD4+ TCR were incubated, in the presence of increasing concentration of HA peptide, with DCs treated with various supernatants, as indicated. Data shown are representative of three experiments using supernatants derived from B16 cells tranfected with either plasmid vectors or oligonucleotides. T cells alone (open circles); medium (closed diamonds); wt (closed squares); GFP (closed triangles); Stat3β (closed circles).

FIG. 5. The pro-inflammatory mediators elaborated by Stat3-interrupted tumor cells activate T cells, including tumor antigen-specific CD8+ T cells, in vivo. a, T cell infiltration at the B16 tumor site after Stat3β gene transfer. Tumor sections from either pIRES-EGFP or pIRES-Stat3β treated B16 tumors were stained with anti-CD3 antibodies. b, Activation of TRP2-specific, CD8+ T cells in vivo as determined by IFNγ ELISPOT assays. The bars represent mean numbers of IFNγ+ T cells detected in $5\times10^5$ splenocytes from indicated mice involving three independent experiments (n=9 for each group; except naïve mice, n=8). c, Melanoma surgical specimens from 4 representative patients, showing presence of heavy immune cell infiltrates in pY-Stat3-negative, but not pYStat3-positive (red) tumors. The percentage of $CD11c^+$ $CD86^{+hi}$MHC class $II^{+hi}$ DCs was later determined by flow cytometric analysis (see FIG. 7).

FIG. 6. Constitutive stat3 signaling in transformed cells induces expression of factors that inhibit DC differentiation. a, v-Src transformation-induced inhibition of DC functional differentiation is Stat3-dependent. Progenitor cells cultured for 8 days with DC medium plus supernatants derived from wild-type 3T3 cells (open bars), v-Src transfected 3T3 cells infected with either control virus (MSCV(striped bars)) or Stat3D (dominant-negative (closed bars)) were subjected to flow cytometric analyses to determine the proportion of $CD11c^+CD86^{+hi}$ and $CD11c^+$MHC class $II^{+hi}$ DCs. DCs differentiated in medium supplemented with the various 3T3 supernatants were also tested for their abilities to activate naïve syngeneic T cells in either medium alone (closed circles) or with 1 mg/ml ovalbumin (OVA (open circles)). Levels of VEGF secreted by the above mentioned 3T3 cell variants inversely correlated with proportions of functional DCs (far right panel). b,c, Enforced Stat3 activity stimulates the release of factors that inhibit DC differentiation. For 3T3 cells, either control virus (open bars), or Stat3C (closed bars) was transduced. VEGF levels in 3T3/Stat3C (closed bars) cultures are higher than that of 3T3/MSCV (closed bars) as shown in the far right panel. d, RT-PCR was performed on 3T3 either transfected with v-Src, v-Src with a dominant-negative form of Stat3, or a vector control. e, VEGF is necessary for B16 tumor supernatant-induced inhibition of DC maturation. Tumor factors, including VEGF, activate Stat3 signaling in BMPCs as determined by EMSAs. Tumor supernatants from indicated tumor cells were present in BMPC culture on day 0 for one hour. Stat3 inhibitor, pY*LKTK and control peptide, pYLKTK, were added to BMPC culture incubated with CT26 supernatant. f, Blocking Stat3 signaling in BMPCs abrogates tumor supernatant-induced inhibition of DC functional differentiation. Tumor supernatants with and without indicated peptides were present for the entire 8-day culture. Data represent one of three experiments with similar results. g, Immunohistochemical analysis of tissue-sections from lymphnodes of melanoma patients. The sections were double labeled with $CD1a^+$ antibodies to visualize dendritic cells and with anti-phospho Stat3 antibodies to visualize activated Stat3 in nuclei. The two top panels show tissue samples free of tumor cells. Note the absence of activated Stat3 in the nuclei of the dendritic cells. The two bottom panels show tissue samples with tumor cells. Note the presence of activated Stat3 in the nuclei of the dendritic cells.

Figure 7A:
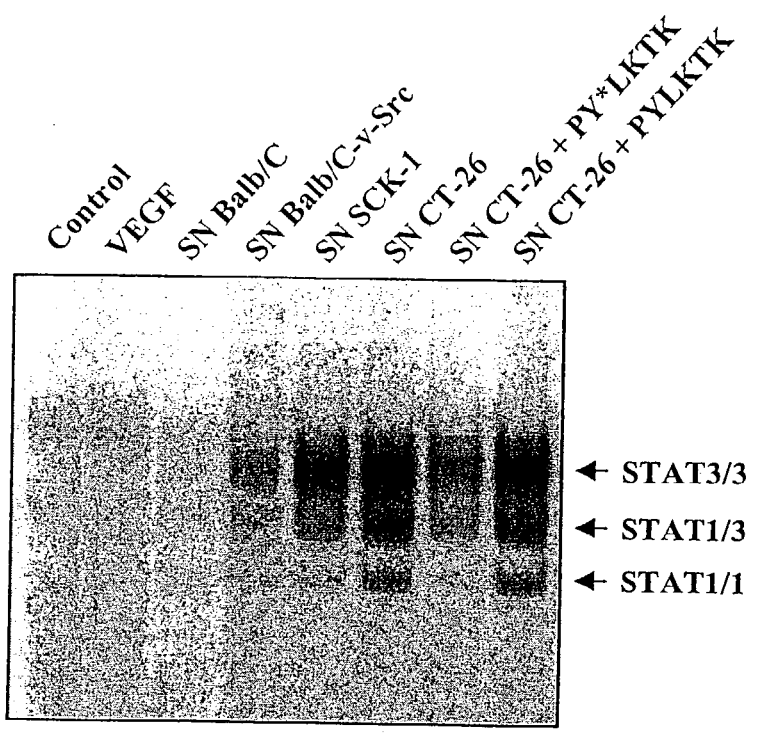
Figure 7B:
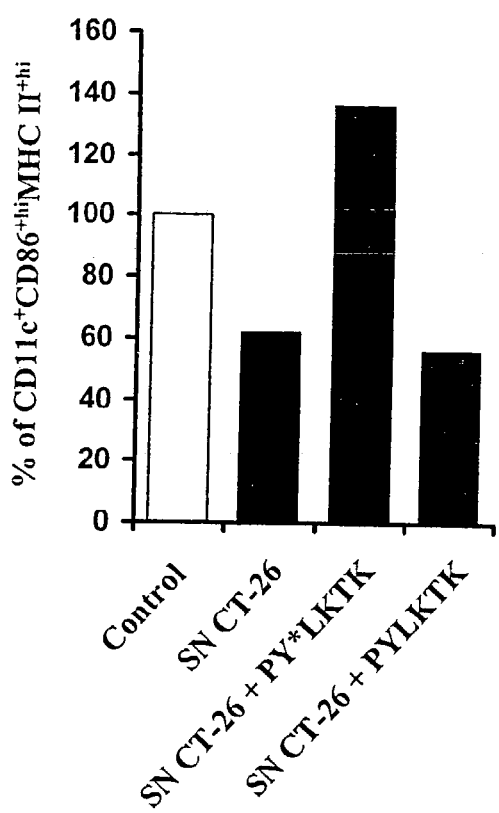

FIG. 7. Inhibition of Stat activity in dendritic cells alleviates the negative effect of tumor-secreted factors on DC differentiation. a, Stat activation in DCs treated for 1 hour with recombinant VEGF (100 ng/ml) or incubated for 15 min. with various supernatants as indicated. The last two lanes represent nuclear extracts isolated from cells pretreated with 250µM of an inhibitory anti-STAT3 (PY*LKTK)(SEQ ID NO: 11); or control (PYLKTK)(SEQ ID NO: 12)peptide. b, Inhibition of Stat activity can relieve the negative effect of tumor-derived factors on DC differentiation. Bone marrow progenitor cells were cultured for 6 days in DC medium alone or in the presence of supernatant from CT26 tumor cells (5%) plus 375 µM of anti-Stat3 (PY*LKTK) (SEQ ID NO: 11); or control (PYLKTK) (SEQ ID NO: 12); peptide. The percentage of CD11c$^+$CD86$^{+hi}$MHC class II$^{+hi}$ DCs was later determined by flow cytometric analysis (shown in FIG. 5f).

5. DETAILED DESCRIPTION OF THE INVENTION

The present invention relates to ex vivo immunotherapeutic methods for treating and/or preventing cancer. The methods of the invention comprise decreasing Stat3 expression and/or function in tumor cells and/or antigen presenting cells. In certain embodiments, Stat3 expression can be decreased by any technique known to the skilled artisan. Methods to decrease Stat3 expression include but are not limited to, mutations in the Stat3 gene, knock-out of the Stat3 gene, antisense technology, targeting of Stat3 protein for protein degradation, activating negative regulators of Stat3 expression, and antagonizing positive regulators of Stat3 expression. In certain other embodiments, Stat3 activity can be decreased by amino acid exchanges in the Stat3 protein, anti-Stat3 antibodies, dominant negative Stat3 protein, negative regulators of Stat3 function, and use of antagonists of Stat3, such as small molecule antagonists of Stat3.

In certain embodiments, the methods of the invention comprise decreasing Stat3 expression and/or function in tumor cells ex vivo, inactivating the tumor cells to prevent further cell division of the tumor cells and using the inactivated tumor cells as a vaccine against cancer. In certain embodiments, the tumor cells are treated with irradiation to prevent their cell division. The tumor cells with decreased Stat3 expression and/or function that are treated such that further cell division is prevented are subsequently administered to the subject in need of treating and/or preventing cancer.

The invention further relates to methods comprising decreasing Stat3 function in tumor cells ex vivo and using them to activate T cells in vitro. The tumor cells with decreased Stat3 function are cultured with T-cells to activate the T-cells. In certain embodiments, antigen-presenting cells are also present in the culture. The activated T-cells are subsequently administered to the subject in need of treatment and/or prevention of cancer. Care should be taken that tumor cells that are capable of further cell divisions are not administered to the patient. To avoid that risk, tumor cells can be irradiated before incubation with the T cells. In other embodiments, the tumor cells and T cells are irradiated after the incubation.

The invention further relates to a method for activating T cells with antigen-presenting cells. These methods comprise decreasing Stat3 expression and/or function in tumor cells and culturing the tumor cells with decreased Stat3 expression and/or function. Subsequently, antigen-presenting cells are exposed to supernatant derived from the culture of tumor cells with decreased Stat3 function. The antigen-presenting cells that were exposed to supernatant derived from tumor cells with decreased Stat3 expression and/or function are subsequently incubated with T cells to activate the T cells. The T cells are then administered to the subject. In certain embodiments, to avoid contamination of the T cells that are to be administered to the subject with tumor cells capable of cell division, irradiation can be used at different steps of the procedure to prevent the tumor cells from further cell division. In a more specific embodiment, the supernatant derived from the tumor cells with decreased Stat3 expression and/or function is irradiated.

In another embodiment, the invention comprises methods for decreasing Stat3 expression and/or function in antigen-presenting cells. The antigen-presenting cells so treated and then mixed with tumor cells that have been treated to prevent further cell division are then co-administered to a subject to stimulate the immune-response in the subject. In certain other embodiments, the antigen-presenting cells with decreased Stat3 expression and/or function are then mixed with molecules that display the antigenicity of a tumor, and then co-administered to a subject to stimulate the immune-response in the subject. Molecules that display the antigenicity of a tumor cell can be, but are not limited to, peptides, glycoproteins, glycopeptides, or RNA molecules and DNA molecules. In even other embodiments, the antigen-presenting cells with decreased Stat3 expression and/or function of the invention are mixed with molecules displaying the antigenecity of an infectious agent, or cells displaying such an antigenic molecule, or with an infectious agent that has been modified such that it does not cause disease in a subject, and then co-administered to a subject to stimulate the immune-response in the subject. In a particular embodiment, the infectious agent is a virus or a bacterium. A molecule displaying the antigenicity of the infectious agent can be a, but is not limited to, a peptide, a glycoprotein, a glycopeptide, a RNA molecule and a DNA molecule.

The invention also encompasses methods for stimulating dendritic cell differentiation. The methods comprise antagonizing Stat3 expression and/or function in tumor cells and culturing the tumor cells with decreased Stat3 expression and/or function. Supernatant derived from the culture of tumor cells with decreased Stat3 expression and/or function is then used to treat dendritic cells. In certain embodiments, the differentiation of dendritic cells can be assayed by, e.g., determining IL-12 levels, MHC II levels, CD86 levels, and/or CD40 levels. In certain specific embodiments, the differentiation of dendritic cells can be assayed by determining the potency of the dendritic cells to activate T cells.

The methods of the invention can be used to treat and/or prevent a tumor, cancer and/or neoplastic disease. In certain embodiments, the methods of the invention are used to inhibit or reduce the growth of a cancer or a neoplastic cell in a patient. In certain embodiments, the methods of the invention are used to stimulate or to augment the immune response in a patient against the cancer or the neoplastic disease that is to be treated in the patient.

5.1 Methods for Treating or Preventing Cancer Using STAT3 Inhibitors

5.1.1 Tumor Cells with Decreased STAT3 Expression and/or Function

In certain embodiments, the invention provides methods for the use of Stat3 inhibitors in vaccines for the treatment and/or prevention of cancer or a neoplastic disease. In this aspect of the invention, Stat3 expression or function is decreased in tumor cells. The tumor cells can be obtained from various sources. Tumor cells can be identified and isolated by any method known in the art. Stat3 expression or function in the tumor cells can be decreased by any method known to the skilled artisan. Subsequently, the tumor cells with decreased Stat3 expression and/or function are administered as a vaccine by any method known to the skilled artisan.

In one embodiment, the tumor cells can be obtained from the patient who is to be treated, i.e., the tumor cells are autologous. In certain embodiments, a mixture of autologous and allogeneic cells is used. In other embodiments, allogeneic tumor cells are used. In a preferred embodiment, tumor cells can be obtained from the subject using biopsy. Tumor cells can be isolated by surgery, endoscopy, other biopsy techniques, affinity chromatography, and fluorescence activated cell sorting (e.g., with fluorescently tagged antibody against an antigen expressed by the cells). In a preferred embodiment, the tumor cells of the invention may be isolated from a tumor that is surgically removed from a human patient who will be treated. Prior to use, solid cancer tissue or aggregated cancer cells should be dispersed, preferably mechanically, into a single cell suspension by standard techniques. Enzymes, such as, but not limited to, proteases, collagenase, and/or DNase may also be used to disperse cancer cells. Tumor cells can be identified by morphology, enzyme assays, proliferation assays, or the presence of cancer-causing viruses. If the tumor is known to express an antigen specific to that tumor, the tumor cell can also be identified or isolated by any biochemical or immunological method known in the art. In certain embodiments, a mixture of cells that encompasses the tumor cell is used. In a specific embodiment, the tumor cells are isolated. In another embodiment, a cell line is established from the tumor cells that were obtained from the patient. Subsequently, cells from the tumor cell line are used with the methods of the invention.

In certain embodiments, a tumor-specific antigen may be expressed recombinantly in autologous or allogeneic cells. In certain embodiments, the tumor-specific antigen is a tumor-specific antigen that is expressed by the tumor that is to be treated in the patient. The cells that express a tumor-specific antigen are subsequently used with the methods of the invention as tumor cells.

In certain other embodiments, the tumor cells are allogeneic tumor cells, i.e., they are obtained from a source different from the patient that is to be treated. In one embodiment, the tumor cells are obtained from a subject by any method well-known to the skilled artisan as discussed above. In one embodiment, the tumor cells are cells of an established cell line. In one embodiment, the allogeneic tumor cells are from the same species as the patient. In a preferred embodiment, the tumor cells are from the same type of tumor as the tumor to be treated in the patient. In a preferred embodiment, the tumor cells express an antigen that is also expressed by the tumor to be treated in the patient. Without being bound by theory, the antigen that is expressed by both the tumor cells and by the tumor to be treated in the patient elicits the antigen-specific immune-response. In one embodiment, the tumor cells express an epitope that is also expressed by the tumor that is to be treated. Without being bound by theory, the tumor cells and the tumor to be treated share at least one epitope in common. In one embodiment, the tumor cells express a tumor-associated antigen that is also expressed by the tumor to be treated in the patient. In one embodiment, the tumor cells express a tumor-specific antigen that is also expressed by the tumor to be treated in the patient. Tumor-specific antigens or fragments or derivatives thereof, are antigens which are present at higher concentration in a tumor cell than a non-tumor cell of the same cell type. For example, such tumor specific or tumor-associated antigens include, but are not limited to, KS 1/4 pan-carcinoma antigen (Perez and Walker, 1990, J. Immunol. 142:3662-3667; Bumal, 1988, Hybridoma 7(4):407-415); ovarian carcinoma antigen (CA125) (Yu, et al., 1991, Cancer Res. 51(2):468-475); prostatic acid phosphate (Tailer, et al., 1990, Nucl. Acids Res. 18(16):4928); prostate specific antigen (Henttu and Vihko, 1989, Biochem. Biophys. Res. Comm. 160(2):903-910; Israeli, et al, 1993, Cancer Res. 53:227-230); melanoma-associated antigen p97 (Estin, et al., 1989, J. Natl. Cancer Inst. 81(6):445-446); melanoma antigen gp75 (Vijayasardahl, et al., 1990, J. Exp. Med. 171(4):1375-1380); high molecular weight melanoma antigen (Natali, et al., 1987, Cancer 59:55-63) and prostate specific membrane antigen. Examples of other such tumor-specific antigens are also known in the art.

Stat3 activity or expression levels can be decreased in the tumor cells by any method well-known to the skilled artisan. Exemplary approaches for decreasing Stat3 expression and function are discussed in Section 5.2. In general, methods to decrease Stat3 expression include, but are not limited to, antisense RNA-mediated approaches, site-specific mutagenesis, double-stranded RNA based approaches (RNAi), agonizing negative regulators of Stat3 expression and antagonizing positive regulators of Stat3 expression. Methods to decrease Stat3 function include, but are not limited to, anti-Stat3 based approaches, administering oligonucleotides that comprise the DNA target sequence of Stat3, site-specific mutagenesis of functional sites of the Stat3 molecule, agonizing positive regulators of Stat3 function and antagonizing positive regulators of Stat3 function. In certain embodiments, Stat3 function and/or expression in tumor cells is decreased ex vivo. In certain embodiments, Stat3 function and/or expression in tumor cells is decreased in tissue culture. Such methods are well-known to the skilled artisan, protocols for which are widely available (see, for example, Current Protocols in Molecular Biology, ed. Ausubel et al., John Wiley and Sons, Inc., 1997, which is incorporated herein by reference.

The tumor cells are treated to prevent further cell division as discussed in Section 5.4. In a specific embodiment, the tumor cells are irradiated. In certain embodiments, the tumor cells are treated subsequent to decreasing Stat3 function and/or expression in the tumor cells. In other embodiments, the tumor cells are treated prior to decreasing Stat3 function and/or expression in the tumor cells. In certain embodiments, the tumor cells are treated concurrently with decreasing Stat3 function and/or expression in the tumor cells.

Subsequent to decreasing Stat3 expression and/or function in the tumor cells and irradiating the tumor cells, the tumor cells are administered to a patient. In certain embodiments, the patient has a cancer or a neoplastic disease. In a preferred embodiment, the tumor cells are autologous to the patient. In another preferred embodiment, the tumor cells are allogeneic to the patient. In certain embodiments, the tumor cells are administered to prevent the occurrence of cancer or a neoplastic disease. In other embodiments, the tumor cells are administered to a patient with a predisposition for cancer to prevent disease, or to prevent a reoccurrence of the disease. In the preferred embodiment, the patient is a human.

5.1.2 Antigen-Presenting Cells with Decreased STAT3 Expression and/or Function

Methods for use of antigen-presenting cells with decreased Stat3 expression and/or function as a vaccine are also provided. Such treated antigen-presenting cells are co-administered with tumor cells or with at least one molecule displaying the antigenicity of the tumor to a patient to treat and/or prevent a cancer or a neoplastic disease. Any technique known in the art can be used to obtain the tumor cells for this aspect of the invention. Any technique known to the skilled artisan can be used to obtain the molecule that displays the antigenicity of the tumor. In a preferred embodiment, the tumor cells are of the same type as the tumor to be treated or prevented in the patient. In another preferred embodiment, the molecule that displays the antigenicity of the tumor is derived from a tumor of the same type as the tumor-type to be treated. The antigen-presenting cell can be any cell capable of presenting an antigen to a T cell and specifically activate T cells against the antigen. In a preferred embodiment, the antigen-presenting cell is a dendritic cell. In another preferred embodiment, the antigen-presenting cell is a macrophage. In yet another preferred embodiment, the antigen-presenting cell is a B lymphocyte. In certain other embodiments, the antigen-presenting cells with decreased Stat3 expression and/or function are co-administered with an infectious agent that has been inactivated, i.e., it is incapable of causing pathological symptoms in the subject, or with a molecule that displays the antigenicity of the infectious agent.

In certain embodiments of the invention, Stat3 expression and/or function is decreased in antigen-presenting cells, and the antigen-presenting cells are then co-administered with tumor cells to a patient to stimulate the immune-response against the tumor in the subject. Any method known in the art can be used to decrease the expression and/or function of Stat3. Exemplary approaches to decrease the expression and/or function of Stat3 are described in Section 5.2.

Antigen-presenting cells useful for this aspect of the invention can be autologous to the patient in which the tumor is to be treated or prevented. In other embodiments, the antigen-presenting cells are allogeneic. Exemplary methods for the isolation of immune cells are described in Section 5.1.2.

In a preferred embodiment, the antigen-presenting cell is a macrophage. In certain embodiments of the invention, the macrophages are activated before administering them to the patient. In certain more specific embodiments, the macrophages are activated with LPS. In certain embodiments, the macrophages are activated with at least 1 ng/ml, 10 ng/ml, 50 ng/ml, 100 ng/ml, 0.5 µg/ml, 1 µg/ml, 1.5 µg/ml, 2 µg/ml, 2.5 µg/ml, 5 µg/ml, or at least 10 µg/ml LPS. In certain embodiments, the macrophages are activated with at most 1 ng/ml, 10 ng/ml, 50 ng/ml, 100 ng/ml, 0.5 µg/ml, 1 µg/ml, 1.5 µg/ml, 2 µg/ml, 2.5 µg/ml, or at most 10 µg/ml LPS. In certain embodiments, the macrophages are activated for at least 0.5 hour, 1 hour, 2.5 hours, 5 hours, 7.5 hours, 10 hours, 15 hours, 20 hours or for at least one day. In certain embodiments, the macrophages are activated for at most 0.5 hour, 1 hour, 2.5 hours, 5 hours, 7.5 hours, 10 hours, 15 hours, 20 hours, or for at most one day.

In a preferred embodiment, the macrophages are activated in a suspension with 2.5 µg/ml LPS for 5 hours, and washed twice.

In certain embodiments, the methods for activation of macrophages includes, but is not limited to, treatment of macrophages with IFN-γ. In certain embodiments, the macrophages are activated with IFN-γ and LPS. In more specific embodiments, the macrophages are activated with IFN-γ followed by activations with LPS. In certain embodiments, the macrophages are activated with at least 0.05 U/ml IFN-γ, 0.1 U/ml IFN-γ, 0.2 U/ml IFN-γ, 0.4 U/ml IFN-γ, 0.75 U/ml IFN-γ, 1 U/ml IFN-γ, 2 U/ml IFN-γ, 4 U/ml IFN-γ, 8 U/ml IFN-γ, 15 U/ml IFN-γ, or at least 25 U/ml IFN-γ. In certain embodiments, the macrophages are activated with at most 0.05 U/ml IFN-γ, 0.1 U/ml IFN-γ, 0.2 U/ml IFN-γ, 0.4 U/ml IFN-γ, 0.75 U/ml IFN-γ, 1 U/ml IFN-γ, 2 U/ml IFN-γ, 4 U/ml IFN-γ, 8 U/ml IFN-γ, 15 U/ml IFN-γ, or at most 25 U/ml IFN-γ. In certain embodiments, the macrophages are activated with IFN-γ for at least 0.5 hour, 1 hour, 2.5 hours, 5 hours, 7.5 hours, 10 hours, 15 hours, 20 hours, or for at least one day. In certain embodiments, the macrophages are activated with IFN-γ for at most 0.5 hour, 1 hour, 2.5 hours, 5 hours, 7.5 hours, 10 hours, 15 hours, 20 hours, or for at most one day. In certain embodiments, the macrophages are activated with LPS for at least 0.5 hour, 1 hour, 2.5 hours, 5 hours, 7.5 hours, 10 hours, 15 hours, 20 hours, or for at least one day. In certain embodiments, the macrophages are activated with LPS for at most 0.5 hour, 1 hour, 2.5 hours, 5 hours, 7.5 hours, 10 hours, 15 hours, 20 hours, or for at most one day. In certain embodiments, the macrophages are activated with at least 1 ng/ml, 10 ng/ml, 50 ng/ml, 100 ng/ml, 0.5 µg/ml, 1 µg/ml, 1.5 µg/ml, 2 µg/ml, 2.5 µg/ml, 5 µg/ml, or at least 10 µg/ml LPS. In certain embodiments, the macrophages are activated with at most 1 ng/ml, 10 ng/ml, 50 ng/ml, 100 ng/ml, 0.5 µg/ml, 1 µg/ml, 1.5 µg/ml, 2 µg/ml, 2.5 µg/ml, 5 µg/ml, or at most 10 µg/ml LPS Any combination of concentrations and durations of IFN-γ and LPS treatment can be used with the methods of the invention.

Without being bound by theory, macrophages that were activated with lower amounts of IFN-γ and/or LPS produce less NO than macrophages that were activated with higher amounts of INF-γ and/or LPS. Lower NO production by the macrophages is correlated with higher efficacy of the macrophages.

In certain embodiments, the activated macrophages are treated such that NO production is eliminated. In more specific embodiments, NO production by macrophages is eliminated by treating the macrophages with an inhibitor of iNOS. Inhibitors of iNOS include, but are not limited to, L-NMA, IPPITU, EITU, MITU, and AEITU.

In another preferred embodiment of the invention, the antigen-presenting cells are dendritic cells ("DC's"). Dendritic cells can be isolated or generated from blood or bone marrow, or secondary lymphoid organs of the subject, such as but not limited to spleen, lymph nodes, tonsils, Peyer's patch of the intestine, and bone marrow, by any of the methods known in the art. Preferably, DCs used in the methods of the invention are differentiated, relatively mature, dendritic cells. The source of dendritic cells is preferably human blood monocytes.

Immune cells obtained from such sources typically comprise predominantly recirculating lymphocytes and macrophages at various stages of differentiation and maturation. Dendritic cell preparations can be enriched by standard techniques (see e.g., Current Protocols in Immunology, 7.32.1-7.32.16, John Wiley and Sons, Inc., 1997). In one embodiment, for example, DCs may be enriched by depletion of T cells and adherent cells, followed by density gradient centrifugation. DCs may optionally be further purified by sorting of fluorescence-labeled cells, or by using anti-CD83 MAb magnetic beads.

Alternatively, a high yield of a relatively homogenous population of DCs can be obtained by treating DC progenitors present in blood samples or bone marrow with cytokines, such as granulocyte-macrophage colony stimulating factor (GM-CSF) and interleukin 4 (IL-4). Under such conditions, monocytes differentiate into dendritic cells without cell proliferation. Further treatment with agents such as TNFα stimulates terminal differentiation of DCs.

In a specific embodiment of the invention, the dendritic cells are activated before administration. Dendritic cells can be activated with beta-defensin 2, for example (Biragyn et al. Science 2002;298:1025-1029).

The tumor cells and the antigen-presenting cells with decreased Stat3 expression and/or function are then co-administered to the patient in need of treatment. In a preferred embodiment, the tumor cells and the antigen-presenting cells are co-administered at a ratio of 1:1. In another preferred embodiment, the tumor cells and the antigen-presenting cells are co-administered at a ratio of at least 1 tumor cell per antigen-presenting cell, at least 2 tumor cells per antigen-presenting cell, at least 3 tumor cells per antigen-presenting cell, at least 5 tumor cells per antigen-presenting cell, at least 10 tumor cells per antigen-presenting cell, at least 25 tumor cells per antigen-presenting cell, at least 50 tumor cells per antigen-presenting cell, at least 100 tumor cells per antigen-presenting cell, at least 500 tumor cells per antigen-presenting cell, at least 1,000 tumor cells per antigen-presenting cell, or at least 10,000 tumor cell per antigen-presenting cell.

In an alternative embodiments, the tumor cells and the antigen-presenting cells are co-cultured at a ratio of at most 1 tumor cell per antigen-presenting cell, at most 2 tumor cells per antigen-presenting cell, at most 3 tumor cells per antigen-presenting cell, at most 5 tumor cells per antigen-presenting cell, at most 10 tumor cells per antigen-presenting cell, at most 25 tumor cells per antigen-presenting cell, at most 50 tumor cells per antigen-presenting cell, at most 100 tumor cells per antigen-presenting cell, at most 500 tumor cells per antigen-presenting cell, at most 1,000 tumor cells per antigen-presenting cell, or at most 10,000 tumor cell per antigen-presenting cell. In certain embodiments, the tumor cells and the antigen-presenting cells are co-administered at a ratio of at least 1 antigen-presenting cell per tumor cell, at least 2 antigen-presenting cells per tumor cell, at least 3 antigen-presenting cells per tumor cell, at least 5 antigen-presenting cells per tumor cell, at least 10 antigen-presenting cells per tumor cell, at least 25 antigen-presenting cells per tumor cell, at least 50 antigen-presenting cells per tumor cell, at least 100 antigen-presenting cells per tumor cell, at least 500 antigen-presenting cells per tumor cell, at least 1,000 antigen-presenting cells per tumor cell, or at least 10,000 antigen-presenting cells per tumor cell. In certain embodiments, the tumor cells and the antigen-presenting cells are co-cultured at a ratio of at most 1 antigen-presenting cell per tumor cell, at most 2 antigen-presenting cells per tumor cell, at most 3 antigen-presenting cells per tumor cell, at most 5 antigen-presenting cells per tumor cell, at most 10 antigen-presenting cells per tumor cell, at most 25 antigen-presenting cells per tumor cell, at most 50 antigen-presenting cells per tumor cell, at most 100 antigen-presenting cells per tumor cell, at most 500 antigen-presenting cells per tumor cell, at most 1,000 antigen-presenting cells per tumor cell, or at most 10,000 antigen-presenting cells per tumor cell.

Tumor cells with decreased Stat3 expression and/or function are then administered with antigen presenting cells to a patient in need of treatment. In a preferred embodiment, $1 \times 10^6$ to $1 \times 10^9$ tumor cells are administered to a patient, in combination with $1 \times 10^6$ to $1 \times 10^9$ antigen-presenting cells. In another preferred embodiment, $5 \times 10^7$ to $2 \times 10^8$ tumor cells are used together with $5 \times 10^7$ to $2 \times 10^8$ tumor cells. In a specific embodiment, approximately $1 \times 10^6$ tumor cells are used with $1 \times 10^6$ antigenic cells.

5.1.3 Methods for the Treatment of Prevention of Infectious Disease

In certain embodiments of the invention, Stat3 expression and/or function is decreased in antigen-presenting cells. The antigen-presenting cells with decreased Stat3 expression and/or function are then mixed with molecules displaying the antigenicity of an infectious agent, or with an infectious agent that has been modified such that it does not cause disease in a subject, and then administered to a subject to stimulate the immune-response in the subject. The antigen presenting cells may be isolated prior to administration, or may be co-administered with the antigenic molecule. In a preferred embodiment, the infectious agent, or the infectious agent from which a molecule that displays the antigenicity of the infectious agent is derived, is of the same type as the infectious agent with which the subject that is to be treated is infected. A molecule displaying the antigenicity of the infectious agent can be, but is not limited to, a peptide, a glycoprotein, a glycopeptide, a RNA molecule and a DNA molecules.

5.1.3.1 Target Infectious Diseases

Infectious diseases that can be treated or prevented by the methods of the present invention are caused by infectious agents including, but not limited to, viruses, bacteria, fungi protozoa, helminths, and parasites. The invention is not limited to treating or preventing infectious diseases caused by intracellular or extracellular pathogens. Combination therapy encompasses in addition to the administration of pharmaceutical compositions of the invention, the uses of one or more modalities that aid in the prevention or treatment of infectious diseases, which modalities include, but is not limited to antibiotics, antivirals, antiprotozoal compounds, antifungal compounds, and antihelminthics. Other treatment modalities that can be used to treat or prevent infectious diseases include immunotherapeutics, polynucleotides, antibodies, cytokines, and hormones as described above.

Infectious virus of both human and non-human vertebrates, include retroviruses, RNA viruses and DNA viruses. Examples of virus that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picomaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Retroviruses that are contemplated include both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian mycloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Reoviridae, including the genus *Orthoreovirus* (multiple serotypes of both mammalian and avian retroviruses), the genus *Orbivirus* (Bluetongue virus, Eugenangee virus, Kemerovo virus, African horse sickness virus, and Colorado Tick Fever virus), the genus *Rotavirus* (human rotavirus, Nebraska calf diarrhea virus, murine rotavirus, simian rotavirus, bovine or ovine rotavirus, avian rotavirus); the family Picornaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus *Cardiovirus* (Encephalomyocarditis virus (EMC), Mengovirus), the *genus Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, Feline picornavirus and Norwalk virus; the family Togaviridae, including the genus *Alphavirus* (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza virus* (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza virus* (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), Chandipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxviridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A,B,C,D,E and ungrouped; simian adenoviruses (at least 23 serotypes), infectious canine hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus *Adeno*-associated viruses, the genus *Parvovirus* (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents.

Many examples of antiviral compounds that can be used in combination with the methods of the invention are known in the art and include but are not limited to: rifampicin, nucleoside reverse transcriptase inhibitors (e.g., AZT, ddI, ddC, 3TC, d4T), non-nucleoside reverse transcriptase inhibitors (e.g., Efavirenz, Nevirapine), protease inhibitors (e.g., aprenavir, indinavir, ritonavir, and saquinavir), idoxuridine, cidofovir, acyclovir, ganciclovir, zanamivir, amantadine, and Palivizumab. Other examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime.

Bacterial infections or diseases that can be treated or prevented by the methods of the present invention are caused by bacteria including, but not limited to, bacteria that have an intracellular stage in its life cycle, such as mycobacteria (e.g., *Mycobacteria tuberculosis, M. bovis, M. avium, M. leprae,* or *M. africanum*), rickettsia, mycoplasma, chlamydia, and legionella. Other examples of bacterial infections contemplated include but are not limited to infections caused by Gram positive bacillus (e.g., *Listeria, Bacillus* such as *Bacillus anthracis, Erysipelothrix* species), Gram negative bacillus (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio,* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species. Specific examples of infectious bacteria include but are not limited to: *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella neumoniae, Pasturella multocida, Fusobacterium nucleatum, Streptobacillus moniliformis, Treponema pallidum, Treponema pertenue, Leptospira, Rickettsia,* and *Actinomyces israelli*

Antibacterial agents or antibiotics that can be used in combination with the methods of the invention include but are not limited to: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Additional examples of antibacterial agents include but are not limited to Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmnenoxime Hydrochloride; Cefmnetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin;

Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofingin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Fungal diseases that can be treated or prevented by the methods of the present invention include but not limited to aspergilliosis, crytococcosis, sporotrichosis, coccidioidomycosis, paracoccidioidomycosis, histoplasmosis, blastomycosis, zygomycosis, and candidiasis.

Antifungal compounds that can be used in combination with the methods of the invention include but are not limited to: polyenes (e.g., amphotericin b, candicidin, mepartricin, natamycin, and nystatin), allylamines (e.g., butenafine, and naftifine), imidazoles (e.g., bifonazole, butoconazole, chlordantoin, flutrimazole, isoconazole, ketoconazole, and lanoconazole), thiocarbamates (e.g., tolciclate, tolindate, and tolnaftate), triazoles (e.g., fluconazole, itraconazole, saperconazole, and terconazole), bromosalicylchloranilide, buclosamide, calcium propionate, chlorphenesin, ciclopirox, azaserine, griseofilvin, oligomycins, neomycin undecylenate, pyrrolnitrin, siccanin, tubercidin, and viridin. Additional examples of antifungal compounds include but are not limited to Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofingin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafuigin; Undecylenic Acid; Viridoflilvin; Zinc Undecylenate; and Zinoconazole Hydrochloride.

Parasitic diseases that can be treated or prevented by the methods of the present invention including, but not limited to, amebiasis, malaria, leishmania, coccidia, giardiasis, cryptosporidiosis, toxoplasmosis, and trypanosomiasis. Also encompassed are infections by various worms, such as but not limited to ascariasis, ancylostomiasis, trichuriasis, strongyloidiasis, toxoccariasis, trichinosis, onchocerciasis, filaria, and dirofilariasis. Also encompassed are infections by various flukes, such as but not limited to schistosomiasis, paragonimiasis, and clonorchiasis. Parasites that cause these diseases can be classified based on whether they are intracellular or extracellular. An "intracellular parasite" as used herein is a parasite whose entire life cycle is intracellular. Examples of human intracellular parasites include *Leishmania* spp., *Plasmodium* spp., *Trypanosoma cruzi, Toxoplasma gondii, Babesia* spp., and *Trichinella spiralis*. An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites". These parasites may exist most of their lives or only a small portion of their lives in an extracellular environment, but they all have at least one obligate intracellular stage in their life cycles. This latter category of parasites includes *Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp.

5.1.4 Stimulating Dendritic Cell Differentiation

In another aspect of the present invention, inhibiting Stat3 can be used to promote dendritic cell differentiation. In certain embodiments of the invention, dendritic cells are treated with the supernatant from tumor cells with decreased Stat3 expression and/or function to stimulate differentiation of the dendritic cells. The differentiated dendritic cells can be administered to a patient to stimulate an immune response in the patient against the tumor. In preferred embodiments, the tumor cells are of the same type as the tumor to be treated or prevented in the subject.

In certain embodiments of the invention, the dendritic cells are activated in vivo by targeting the dendritic cells in a lymphoid organ. In a specific embodiment, the supernatant from tumor cells with decreased Stat3 expression and/or function is administered to a subject to activate dendritic cell differentiation. In an even more specific embodiment, the supernatant is administered tissue-specifically by any method known to the skilled artisan.

In certain embodiments, the dendritic cells are autologous. In certain other embodiments, the dendritic cells are allogeneic. In certain embodiments, the tumor cells are autologous. In certain other embodiments, the tumor cells are allogeneic.

The tumor cells can be obtained by any method well-known to the skilled artisan. Exemplary methods for the isolation of tumor cells are described in Section 5.1.1. Supernatant from the tumor cells can be obtained by any method known to the skilled artisan; exemplary approaches are described in Section 5.1.2. In one embodiment, the supernatant is irradiated to ensure that no tumor cells that are capable of cell division remain in the supernatant.

The dendritic cells may be mature or immature dendritic cells, but are preferably relatively mature dendritic cells. Exemplary methods for the isolation of dendritic cells are described in Section 5.1.2. Subsequent to their isolation, dendritic cells are cultured by any standard technique well-known to the skilled artisan. The supernatant obtained from the tumor cells with decreased Stat3 expression and function is added to the culture of dendritic cells. In certain embodiments, at least 0.1%, 0.25%, 0.5%, 1%, 2.5%, 5%, 7.5%, 10%, 15%, 20%, 25%, 50%, 75%, 90%, 95% or at least 98% of the dendritic cell culture volume is supernatant from the tumor cells with decreased Stat3 expression and/or function. In certain embodiments, at most 0.1%, 0.25%, 0.5%, 1%, 2.5%, 5%, 7.5%, 10%, 15%, 20%, 25%, 50%, 75%, 90%, 95% or at most 98% of the dendritic cell culture volume is supernatant from the tumor cells with decreased Stat3 expression and/or function. In certain embodiments, the dendritic cells are cultured in the supernatant containing medium for at least 6 hours, 12 hours, 24 hours, 2 days, 3 days, 4 days, 5 days, 6 days, 7 days, 2 weeks, 3 weeks, 4 weeks, 2 months, or 3 months. In certain embodiments, the dendritic cells are cultured in the supernatant-containing medium for at most 6 hours, 12 hours, 24 hours, 2 days, 3 days, 4 days, 5 days, 6 days, 7 days, 2 weeks, 3 weeks, 4 weeks, 2 months, or 3 months.

In a preferred embodiment, the culture is supplemented with 20% to 30% supernatant. In a preferred embodiment, fresh supernatant is added to the culture every other day until day 6 of the culture.

The differentiated dendritic cells can be identified by any technique known to the skilled artisan. For example the expression of certain marker genes by differentiated dendritic cells enables the skilled artisan to identify and isolate differentiated dendritic cells from undifferentiated dendritic cells. Markers for dendritic. cell differentiation are described in Section 5.3.11. In certain embodiments, differentiated dendritic cells are isolated from the culture of dendritic cells by virtue of their expression of markers specific for differentiated dendritic cells. In one embodiment, all cells are collected from the culture by gentle centrifugation and subsequent washing in an isotonic buffer, such as PBS. The differentiated dendritic cells can be isolated from the culture by incubating the cells with a first antibody that binds specifically to a marker that is specifically expressed by differentiated dendritic cells. In one embodiment, the first antibody is labeled with a fluorophor and the differentiated dendritic cells are isolated using FACS. In another embodiment, a secondary antibody that (a) binds specifically to the first antibody and (b) is attached to a solid support is incubated with the cells from the culture after the first antibody has been added. The cells are then washed and the differentiated dendritic cells eluted from the solid support.

The differentiated dendritic cells are administered to a patient. The cells can be administered to the patient by any technique known to the skilled artisan as, e.g., described in Section 5.7.1, below. In certain embodiments, the patient has cancer or a neoplastic disease. In certain embodiments, the differentiated dendritic cells are allogeneic. In other embodiments, the differentiated dendritic cells are autologous. In certain embodiments, the differentiated dendritic cells are administered to prevent the occurrence of cancer or a neoplastic disease. In certain embodiments, the differentiated dendritic cells are administered to a patient to stimulate an immune response against a tumor or a neoplastic growth. In certain embodiments, the differentiated dendritic cells are administered in a patient to inhibit or reduce the growth of a cancer cell and/or a neoplastic cell. In certain embodiments the differentiated dendritic cells are administered to a patient to augment the immune response in the patient against a cancer or a neoplastic disease. In certain embodiments, the tumor cells that were used to obtain the supernatant for incubating the dendritic cells are of the same type as the type of tumor or cancer that is to be treated and/or prevented in the patient.

In certain embodiments of the invention, the differentiation of dendritic cells is stimulated by decreasing Stat3 expression and/or function in cells capable of differentiating into dendritic cells. In a preferred embodiment, bone marrow progenitor cells may be used. The bone marrow progenitor cells can be autologous or allogeneic. Stat3 expression and/or function can be decreased in the bone-marrow progenitor cells by any method known to the skilled artisan. Exemplary methods for decreasing Stat3 expression and/or function in a cell are described in Section 5.2. Differentiated dendritic cells can be identified and isolated by the presence, absence, up-regulation, or down-regulation of any marker known to the skilled artisan. In preferred embodiments, the differentiated dendritic cells are selected by the presence of CD11, up-regulation of CD86, or up-regulation of class II MHC.

5.2 Methods for Decreasing STAT3 Expression and Function

Many methods are known to the skilled artisan to decrease the expression and/or function of Stat3 in a cell. Any technique known in the art can be used to decrease the expression and/or to decrease the function of Stat3 in a cell. In certain embodiments, decreasing Stat3 expression can be accomplished by reducing and/or eliminating the gene-expression of Stat3. In certain embodiments, decreasing Stat3 expression can be accomplished by reducing and/or eliminating the protein expression of Stat3. Several activities of the Stat3 protein can be reduced and/or eliminated to decrease the function of Stat3. Such Stat3 activities include, but are not limited to, dimerization, nuclear transport, transactivation activity, nuclear transport, and/or DNA binding activity.

5.2.1 STAT3 Expression

Any technique to reduce or to eliminate Stat3 gene and/or protein expression can be used with the methods of the invention. For example, in certain embodiments, transcription of Stat3 is reduced or eliminated or silenced. One method that can be used is site-specific mutagenesis. In certain embodiments, parts of the cis-regulatory control elements of the Stat3 gene are mutated or removed by deletion such that the Stat3 gene is transcribed at a lower rate or such that Stat3 gene transcription is abolished.

In another embodiment, Stat3 gene expression can be reduced or eliminated by inactivating or "knocking out" the target gene or its cis-regulatory control element using targeted homologous recombination (e.g., see Smithies, et al., 1985, Nature 317, 230-234; Thomas & Capecchi, 1987, Cell 51, 503-512; Thompson, et al., 1989, Cell 5, 313-321; each of which is incorporated by reference herein in its entirety). For example, a mutant, non-functional cis-regulatory control element (or a completely unrelated DNA sequence) flanked by DNA homologous to the endogenous target gene (either the coding regions or regulatory regions of the target gene) can be used, with or without a selectable marker and/or a negative selectable marker, to transfect cells that express the Stat3 in vivo. Insertion of the DNA construct via targeted homologous recombination results in inactivation of the Stat3 gene. In certain embodiments of the invention, mutations can be introduced into the Stat3 gene using chimeric oligonucleotides.

In a specific embodiment, a cis-regulatory control element of the Stat3 gene that is required for Stat3 expression in macrophages is mutated or removed by homologous recombination in mouse embryonic stem cells to generate mice with macrophages with reduced or absent Stat3 expression.

Alternatively, endogenous Stat3 gene expression can be reduced by targeting deoxyribonucleotide sequences complementary to the regulatory region of Stat3 (i.e., the target gene promoter and/or enhancers) to form triple helical structures that prevent transcription of Stat3 in target cells in the body. (See generally, Helene, 1991, Anticancer Drug Des. 6(6): 569-584; Helene, et al., 1992, Ann. N.Y. Acad. Sci. 660: 27-36; and Maher, 1992, Bioassays 14(12): 807-815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

In certain other embodiments of the invention, Stat3 translation is reduced or eliminated. Any technique well-known to the skilled artisan can be used with the methods of the invention to reduce or eliminate Stat3 translation.

Among the compounds that may exhibit the ability to modulate the translation of Stat3 are antisense and ribozyme molecules. Techniques for the production and use of such molecules are well known to those of skill in the art.

Without being bound by theory, antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of a RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the Stat3 gene could be used in an antisense approach to inhibit translation of endogenous Stat3 mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Stat3 antisense molecules complementary to coding or non-coding regions may be used, members of both are well known in the art. Representative, non-limiting examples of Stat3 antisense molecules include the following: 5'-ACTCAAACTGCCCTCCTGCT-3'(SEQ ID NO: 1); 5'-TCTGAAGAAACTGCTTGATT-3'(SEQ ID NO: 2); 5'-GCCACAATCCGGGCAATCT-3'(SEQ ID NO: 3); 5'-TGGCTGCAGTCTGTAGAAGG-3'(SEQ ID NO: 4); 5'-TTTCTGTTCTAGATCCTGCA-3'(SEQ ID NO: 5); 5'-TAGTTGAAATCAAAGTCATC-3'(SEQ ID NO: 6); 5'-TTCCATTCAGATCTTGCATG-3'(SEQ ID NO: 7); 5'-TCTGTTCCAGCTGCTGCATC-3'(SEQ ID NO: 8); 5'-TCACTCACGATGCTTCTCCG-3'(SEQ ID NO: 9); 5'-GAGTTTTCTGCACGTACTCC-3' (SEQ ID NO: 10)(see, e.g., U.S. Pat. No. 6,159,694, issued Dec.12, 2000, which is incorporated herein in its entirety).

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86: 6553-6556; Lemaitre et al., 1987, Proc. Natl. Acad. Sci. 84: 648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958-976) or intercalating agents (see, e.g., Zon 1988, Pharm. Res. 5: 539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate (S-ODNs), a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., 1987, Nucl. Acids Res. 15: 6625-6641). The oligonucleotide is a 2-0-methylribonucleotide (Inoue et al., 1987, Nucl. Acids Res. 15: 6131-6148), or a chimeric RNA-DNA analogue (Inoue et al., 1987, FEBS Lett. 215: 327-330).

Oligonucleotides to be used with the methods of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85: 7448-7451), etc.

While antisense nucleotides complementary to the Stat3 coding region sequence could be used, those complementary to the transcribed, untranslated region are most preferred.

In one embodiment of the present invention, Stat3 gene expression downregulation is achieved because specific target mRNAs are digested by RNAse H after they have hybridized with the antisense phosphorothioate oligonucleotides (S-ODNs). Since no rules exist to predict which antisense S-ODNs will be more successful, the best strategy is completely empirical and consists of trying several antisense S-ODNs. Antisense phosphorothioate oligonucleotides (S-ODNs) will be designed to target specific regions of Stat3 mRNA of interest. Control S-ODNs consisting of scrambled sequences of the antisense S-ODNs will also be designed to assure identical nucleotide content and minimize differences potentially attributable to nucleic acid content. In order to test the effectiveness of the antisense molecules when applied to cells in culture, such as assays for research purposes or ex vivo gene therapy protocols, cells will be grown to 60-80% confluence on 100 mm tissue culture plates, rinsed with PBS and overlaid with lipofection mix consisting of 8 ml Opti-MEM, 52.8 l Lipofectin, and a final concentration of 200 nM S-ODNs. Lipofections will be carried out using Lipofectin Reagent and Opti-MEM (Gibco BRL). Cells will be incubated in the presence of the lipofection mix for 5 hours. Following incubation the medium will be replaced with complete DMEM. Cells will be harvested at different time points post-lipofection and protein levels will be analyzed by Western blot.

It is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect a cell will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Benoist and Chambon, 1981, Nature 290, 304-310), the promoter contained in the 3 long terminal repeat of Rous sarcoma virus (Yamamoto et al., 1980, Cell 22, 787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), etc. Any type of plasmid, cosmid, YAC or viral vector can be used to prepare the recombinant DNA construct which can be used to transfect the cell.

Ribozyme molecules designed to catalytically cleave target gene mRNA transcripts can also be used to prevent translation of Stat3 gene mRNA and, therefore, expression of Stat3 gene product (see, e.g., PCT International Publication WO90/11364, published Oct. 4, 1990; Sarver, et al., 1990, Science 247, 1222-1225).

Ribozymes are enzymatic RNA molecules capable of catalyzing the specific cleavage of RNA. (For a review, see Rossi, 1994, Current Biology 4: 469-471). The echanism of ribozyme action involves sequence specific hybridization of the ribozyme olecule to complementary Stat3 RNA, followed by an endonucleolytic cleavage event. The composition of ribozyme molecules must include one or more sequences complementary to the Stat3 gene mRNA, and must include the well known catalytic sequence responsible for mRNA cleavage. For this sequence, see, e.g., U.S. Pat. No. 5,093, 246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, Molecular Biology and Biotechnology: A Comprehensive Desk Reference, VCH Publishers, New York, (see especially FIG. 4, page 833) and in Haseloff and Gerlach, 1988, Nature 334: 585-591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al., 1984, Science, 224:574-578; Zaug and Cech, 1986, Science, 231:470-475; Zaug, et al., 1986, Nature, 324: 429-433; published International patent application No. WO 88/04300 by University Patents Inc.; Been & Cech, 1986, Cell, 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pot III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Anti-sense RNA and DNA, ribozyme, and triple helix molecules to be used with the methods of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In certain embodiments, Stat3 expression is decreased by increasing the degradation of Stat3 protein in the cell. In a specific embodiment, Stat3 can be targeted for degradation by the proteasome pathway.

5.2.1.1 RNA Interference

In certain embodiments, an RNA interference (RNAi) molecule is used to decrease Stat3 expression. RNA interference (RNAi) refers to the use of double-stranded RNA (dsRNA) or small interfering RNA (siRNA) to suppress the expression of a gene comprising a related nucleotide sequence. RNAi is also called post-transcriptional gene silencing (or PTGS). Since the only RNA molecules normally found in the cytoplasm of a cell are molecules of single-stranded mRNA, the cell has enzymes that recognize and cut dsRNA into fragments containing 21-25 base pairs (approximately two turns of a double helix and which are referred to as small interfering RNA or siRNA). The antisense strand of the fragment separates enough from the sense strand so that it hybridizes with the complementary sense sequence on a molecule of endogenous cellular mRNA. This hybridization triggers cutting of the mRNA in the double-stranded region, thus destroying its ability to be translated into a polypeptide. Introducing dsRNA corresponding to a particular gene thus knocks out the cell's own expression of that gene in particular tissues and/or at a chosen time.

Double-stranded (ds) RNA can be used to interfere with gene expression in mammals. dsRNA is used as inhibitory RNA or RNAi of the function of a nucleic acid molecule of the invention to produce a phenotype that is the same as that of a null mutant of a nucleic acid molecule of the invention (Wianny & Zernicka-Goetz, 2000, Nature Cell Biology 2: 70-75).

Alternatively, siRNA can be introduced directly into a cell to mediate RNA interference (Elbashir et al., 2001, Nature 411:494-498). Many methods have been developed to make siRNA, e.g, chemical synthesis or in vitro transcription. Once made, the siRNAs are introduced into cells via transient transfection. See also U.S. Patent Applications 60/265232, Ser. No. 09/821,832 and PCT/US01/10188, directed to RNA Sequence-Specific Mediators of RNA Interference. A number of expression vectors have also been developed to continually express siRNAs in transiently and stably transfected mammalian cells (Brummelkamp et al., 2002 Science 296: 550-553; Sui et al., 2002,. PNAS 99(6):5515-5520; Paul et al., 2002, Nature Biotechnol. 20:505-508). Some of these vectors have been engineered to express small hairpin RNAs (shRNAs), which get processed in vivo into siRNA-like molecules capable of carrying out gene-specific silencing. Another type of siRNA expression vector encodes the sense and antisense siRNA strands under control of separate pol III promoters (Miyagishi and Taira, 2002, Nature Biotechnol. 20:497-500). The siRNA strands from this vector, like the shRNAs of the other vectors, have 5' thymidine termination signals. Silencing efficacy by both types of expression vectors was comparable to that induced by transiently transfecting siRNA.

5.2.2 STAT3 Function

Any technique to decrease the function of Stat3 well-known to the skilled artisan can be used with the methods of the invention. Stat3 activities include, but are not limited to, dimerization, nuclear transport, transactivation activity, and/or DNA binding activity. One or more of these activities can be reduced or eliminated by introducing a site-specific mutation into the Stat3 coding region. Such mutations can be introduced by a homologous recombination approach as described above. In certain embodiments of the invention, RNA/DNA oligonucleotides are used to introduce a mutation in the coding region of the Stat3 gene (see, e.g., Bandyopadhyay, P. et al., 1999, J. Biol. Chem. 274, 10163-10172).

In certain embodiments, the transactivation activity of Stat3 is decreased. In certain more specific embodiments, amino acids that are required for the transactivation activity of Stat3 are deleted or mutated by site-specific mutagenesis.

In certain embodiment, Stat3 function is decreased by the expression of a dominant negative form of Stat3. In a specific embodiment, the dominant negative form of Stat3 is Stat3β. Compared to Stat3, Stat3β. lacks the C-terminal transactivation domain. Co-expression of Stat3β inhibits the transactivation potential of Stat3, thus effectively inhibiting Stat3 activity (Caldenhoven et al., 1996, J.Biol. Chem. 271:13221-13227). Stat3β can be introduced into a cell either as protein or as a nucleic acid encoding Stat3β. Any method well-known to the skilled artisan can be used to express recombinant Stat3β in a cell or to introduce Stat3β protein into a cell.

The function of Stat3 in a cell can be decreased by introducing a negative regulator of Stat3, such as SOCS and PIAS, into the cell. Such a negative regulator can either be expressed in the cell from a recombinant nucleic acid molecule or the protein can be introduced into the cell directly.

In another embodiment of the invention, Stat3 function is decreased by inhibiting or reducing the dimerization of Stat3. In a specific embodiments, mutations are introduced into the endogenous Stat3 gene to eliminate those amino acids that are required for dimerization of Stat3. In specific embodiments, a SH2 domain of Stat3 is mutated or deleted. In specific embodiments, the ability of Stat3 to heterodimerize is inhibited. In other embodiments, the ability of Stat3 to homodimerize is inhibited.

In another embodiment, the nuclear transport of Stat3 is inhibited to decrease Stat3 function. In specific embodiment, amino acids that are required for nuclear transport of Stat3 are deleted or exchanged in the endogenously expressed Stat3 protein by site-specific utagenesis. In other embodiments, the cells are incubated with inhibitors of nuclear transport. Without being bound by theory, inhibiting the import of Stat3 into the nucleus will reduce the concentration of Stat3 in the nucleus or completely remove Stat3 from the nucleus. As a result, Stat3 cannot exert its activity as a transcription factor.

In other embodiments, the cells are incubated in the presence of inhibitors of transcription. Such transcription inhibitors are well known to the skilled artisan. In certain embodiments, the DNA-binding activity of Stat3 is inhibited. This can be achieved by mutating or deleting the sites of Stat3 that are required for DNA binding. Alternatively DNA-binding activity may be reduced by administering molecules that bind to the DNA-binding domain of Stat3 to the cells. In a specific embodiment, a molecule that binds to the DNA-binding domain of Stat3 is an oligonucleotide that comprises the nucleotide sequence to which Stat3 binds.

5.3 Assays for Use with the Invention

Many techniques are know to the skilled artisan to assay for the abundance and/or activity of Stat3. Any technique well-know to the skilled artisan for testing DNA binding of Stat3, site-specific DNA-binding activity of Stat3, transactivation activity of Stat3, nuclear transport of Stat3, phosphorylation levels of Stat3, expression of target genes of Stat3, and/or dimerization of Stat3 can be used with the methods of the invention.

Many techniques are known to the skilled artisan to assay for the activation of T-cells and for the differentiation of antigen-presenting cells. Any technique well-known to the skilled artisan to test the expression of marker genes in T-cells and in antigen-presenting cells can be used with the methods of the invention. Any technique well-known to the skilled artisan to test a change in cellular behavior or morphology of T-cells and antigen-presenting cells can be used with the methods of the invention. Detailed protocols for use with the invention are described in, e.g., Current Protocols in Immunology, John E. Coligan et al. (editors), John Wiley & Sons.

5.3.1 Nitric Oxide Production

Any method known to the skilled artisan can be used to detect nitric oxide. In certain embodiments calorimetric test is used to measure the concentration of nitric oxide. In a specific embodiment, the Griess assay is used to detect nitric oxide. Kits to conduct the Griess assay are commercially available from, e.g., Oxford Biomedical Research, Inc. (Oxford, Mich.).

5.3.2 Activation of Immune Cells such as Macrophages, T-Cells, and Neutrophils

The activation of immune cells can be demonstrated for example by measuring the expression levels of markers of activation. In the case of macrophages such markers include, but are not limited to, the nitric oxide synthase, iNOS, and the chemokine RANTES. If the activation of T-cells is to be investigated, interferon-γ (IFN-γ) and interleukin-2 (IL-2) can be used as markers. Expression of the tumor necrosis factor alpha (TNFα) can be used as a marker if neutrophils are used in this assay system. The length of the time period between stimulation and assay of expression of said markers may be changed and depends on the precise experimental conditions. A minimum of experimentation is necessary to establish the assay system to which the invention relates in such a way that it functions optimally. The levels of iNOS, RANTES, IFN-γ, IL-2, and TNFα can be determined by immunoblotting, Northern blotting, RNAse protection assays, immunocytochemistry or similar techniques well known to the skilled artisan. For any of those techniques probes specific to iNOS, RANTES, IFN-γ, IL-2, and TNFα, respectively, have to be employed. Such probes comprise antibodies and antisense RNA molecules. The detection of such probes is well established in the art.

If an animal model is employed, macrophages, T-cells and neutrophils can be isolated from the animal and subsequently analyzed or, alternatively, expression levels of iNOS, RANTES, IFN-γ, IL-2, and TNFα can be tested in situ by immunohistochemistry or in situ hybridization. For any of those techniques probes specific to iNOS, RANTES, IFN-γ, IL-2, and TNFα, respectively, have to be employed. Such probes comprise antibodies and antisense RNA molecules.

The detection of such probes is well established in the art. Quantification and statistical analysis of the data is done by standard methods.

5.3.3 DNA Binding of STAT3

One aspect of the function of Stat3 is its ability to bind DNA. In particular, one aspect of the function of Stat3 is its ability to bind DNA site-specifically. To test the ability of Stat3 to bind DNA, a gel shift assay can be employed. Briefly, oligonucleotides comprising the Stat3 binding sequence are incubated with Stat3 protein under conditions conducive to site-specific binding of Stat3 to the oligonucleotide. The Stat3 protein can be a fragment of Stat3 that comprises the DNA binding domain. In specific embodiments, the oligonucleotide is labeled. The oligonucleotide can be, e.g., radioactively labeled. Alternatively, the oligonucleotide can be labeled with a fluorophore. Subsequent to the incubation step, the reaction mixture is resolved on a gel to separate unbound from bound oligonucleotide. Various techniques are known to visualize the oligonucleotide/protein complex in the gel. In a specific embodiment, the oligonucleotide is visualized by virtue of its radioactivity by autoradiography. A mobility shift from the faster migrating unbound oligonucleotide to the slower migrating oligonucleotide bound to Stat3 demonstrates binding between Stat3 and the oligonucleotide. For general protocols on mobility shift assays, see units 12-2 to 12-8 in Short Protocols in Molecular Biology, Ausubel et al. (editors), John Wiley & Sons, Inc., 4$^{th}$ edition, 1999. Additionally, a supershift assay can be conducted to verify the presence of Stat3 in the complex. For the oligonucleotide used in the supershift assay, Stat3 and anti-Stat3 antibodies are incubated and subsequently resolved on a gel. The oligonucleotide/Stat3/anti-Stat3 antibody complex migrates slower in the gel than the oligonucleotide/Stat3 complex. If only a fragment of Stat3 is used for the assay, care should be taken that the antibodies bind to that fragment. For a protocol on antibody supershift assays, see unit 12-10 in Short Protocols in Molecular Biology, Ausubel et al. (editors), John Wiley & Sons, Inc., 4$^{th}$ edition, 1999.

5.3.4 Transactivation Activity of STAT3

In certain embodiments, the transcriptional activity of Stat3 is determined by measuring the expression levels of Stat3's natural target genes.

In certain other embodiments, the transcriptional activity of Stat3 is determined by measuring the expression levels of reporter genes that are under the control of a Stat3 response element and a basal promoter. The biochemical activity of the expression level of the reporter gene represents the activity of the Stat3. Reporter genes that can be used with the methods of invention include, but are not limited to, the genes listed in the Table 1 below:

TABLE 1

Reporter genes and the biochemical properties of the respective reporter gene products

| Reporter Gene | Protein Activity & Measurement |
| --- | --- |
| CAT (chloramphenicol acetyltransferase) | Transfers radioactive acetyl groups to chloramphenicol |
| GAL (b-galactosidase) | Detection by thin layer chromatography and autoradiography |
| GUS (b-glucuronidase) | Hydrolyzes colorless galactosides to yield colored products. |
| LUC (luciferase) | Hydrolyzes colorless glucuronides to yield colored products. |
| GFP (green fluorescent protein) | Oxidizes luciferin, emitting photons |

TABLE 1-continued

Reporter genes and the biochemical properties of the respective reporter gene products

| Reporter Gene | Protein Activity & Measurement |
| --- | --- |
| SEAP (secreted alkaline phosphatase) | luminescence reaction with suitable substrates or with substrates that generate chromophores |
| HRP (horseradish peroxidase) | in the presence of hydrogen oxide, oxidation of 3,3',5,5'-tetramethylbenzidine to form a colored complex |
| AP (alkaline phosphatase) | luminescence reaction with suitable substrates or with substrates that generate chromophores |

In certain embodiments, a reporter gene under the control of a Stat3 response element is cloned into a vector that can be transfected into the cells in which Stat3 activity is to be analyzed. Transfection procedures are well-known to the skill artisan and include, but are not limited to, DEAE-dextran-mediated, Calcium phosphate-mediated, Electroporation, and Liposome-mediated transfection (see Section 5.6.2.2). The abundance and/or activity of the reporter gene is proportional to the activity of the Stat3 response element and consequently to Stat3 transcriptional activity. The abundance of the reporter gene can be measured by, inter alia, Western blot analysis or Northern blot analysis or any other technique used for the quantification of transcription of a nucleotide sequence, the abundance of its mRNA its protein (see Short Protocols in Molecular Biology, Ausubel et al. (editors), John Wiley & Sons, Inc., 4$^{th}$ edition, 1999). In a particular embodiment, a transcriptional run-on assay is used to determine the transcriptional activity from the Stat3 responsive element and thus the activity of Stat3 (for a protocol on run-on assays see, e.g., Reich et al, 1987, Proc. Natl. Acad. Sci. 84:6394-6398). In certain embodiments, the activity of the reporter gene product is measured as a readout of the transcriptional activity of the promoter sequence that is cloned in front of the nucleotide sequence encoding the reporter gene. For the quantification of the activity of the reporter gene product, biochemical characteristics of the reporter gene product can be employed (see Table 1). The methods for measuring the biochemical activity of the reporter gene products are well-known to the skilled artisan.

5.3.5 Nuclear Transport of STAT3

Any technique well-known to the skilled artisan can be used to determine the subcellular localization of Stat3. In certain embodiments, immunocytochemistry using anti-Stat3 specific antibodies is employed to determine the ratio. between Stat3 protein in the cytoplasm and Stat3 protein in the nucleus. In another embodiment, confocal fluorescence microscopy is used to determined the level of Stat3 in the nucleus. In another embodiment Oct. 30, 2002, the Stat3 protein is expressed as a Stat3-GFP fusion protein. The subcellular localization can be determined by confocal fluorescence microscopy.

In certain other embodiments, cytoplasm is separated from nuclei by lysing the cells without lysing the nuclear envelope and subsequent sucrose gradient centrifugation. Protocols for the isolation of nuclei from cells are provided, e.g., in Graham et al., 1994, Anal. Biochem. 220:367-373; Provost et al., 1996, Biochem. J, 319:285-291; Valenzuela, et al., 1997, J. Biol. Chem., 272:12575-12582. The respective Stat3 levels in the cytoplasmic fraction and the nuclear fraction can be determined by Western blot analysis using anti-Stat3 specific antibodies.

5.3.6 Phosphorylation Levels of STAT3

Without being bound by theory, phosphorylation of Stat3, particularly at residues Tyr705 and Ser727, promotes dimerization and subsequent nuclear transport of Stat3. Once in the nucleus, Stat3 is transcriptionally active. An indirect readout of Stat3 phosphorylation is the amount of Stat3 localized to the nucleus. Stat3 phosphorylation can be determined more directly by using antibodies specific to phosphorylated Stat3. In specific embodiments, protein extracts from the cells are subjected to a Western blot analysis using antibodies specific to phosphorylated Stat3. In other embodiments, Stat3 is immunoprecipitated before Western blot analysis with antibodies specific to phosphorylated Stat3. In even other embodiments, Stat3 phosphorylation is determined by Trypsin digestion of immunoprecipitated Stat3 and subsequent 2D gel analysis. Phosphate groups can be radioactively labeled to better visualize the phosphorylated peptides. Alternatively, anti-Phospho-Tyrosine and anti-Phospho-Serine specific antibodies can be used to detect the phosphorylated peptides.

5.3.7 Dimerization Levels of STAT3

In another embodiment, Stat3 dimerization may be assayed to determine the function of Stat3 in a cell. Without being bound by theory, Stat3 dimerizes via reciprocal interactions between the SH2 domains. Any technique well-known to the skilled artisan can be used to determine the levels of Stat3 dimer. In one embodiment, the level of Stat3 dimer is determined by non-denaturing PAGE. In another embodiment, Stat3 dimer concentration is determined by subjecting protein extract from the cells of interest to sucrose-gradient centrifugation. Subsequently to the centrifugation, fractions are collected from the centrifugation tube. The fractions are subjected to Western blot analysis using anti-Stat3 antibodies to visualize the Stat3 protein in the different fractions. The presence of Stat3 in a fraction that corresponds to twice the molecular weight of Stat3 indicates the presence of Stat3 dimer in the protein extract of the cells.

5.3.8 STAT3 Expression

In another embodiment, Stat3 expression levels may be assayed. Any technique well-known to the skilled artisan can be used to determine expression levels of Stat3. In certain embodiments, Stat3 expression is determined by measuring Stat3 mRNA levels. Methods for determining mRNA levels include, but are not limited to, Northern blot analysis using a Stat3 specific probe, RT-PCR using Stat3 specific primers, and in situ hybridization using a Stat3 specific probe. In other embodiments, Stat3 protein levels are determined by methods such as Western blot analysis or immunocytochemistry using anti-Stat3 antibodies.

5.3.9 T Cell Activation

In another embodiment, the activation of T cells may be assayed. T cell activation can be determined in vivo. To determine activation of T cells in vivo, T cell infiltration at a tumor site is determined. In one embodiment, tumor cells are injected into mice. Once the tumors have reached a certain size, the animals are sacrificed and the tumors are subjected to immunohistochemistry using anti-CD3 specific antibodies to visualize T cells.

In other embodiments, the activation of T-cells is determined by measuring the levels of interferon-γ (IFN-γ) or interleukin-2 (IL-2).

5.3.10 Cytotoxicity Assay

Cytotoxicity of immune cells, such as T cells, may be assayed using a $^{51}$Cr release assay, a cytokine assay, or any assay known in the art for measuring reactivity of immune effector cells.

By way of example but not limitation, the following four (4) hour $^{51}$Cr-release assay can be used (see, Palladino et al., 1987, Cancer Res. 47:5074-5079 and Blachere et al., 1993, J. Immunotherapy 14:352-356). In this assay, the immune cells, are added to a target cell suspension, i.e., cells expressing a particular antigen and negative control cells, to give various effector:target (E:T) ratios (usually from 1:1 to 40:1). The target cells are prelabeled by incubating $1 \times 10^6$ target cells in culture medium containing 200 mCi $^{51}$Cr/ml for one hour at 37° C. The labeled cells are washed three times following labeling. Each assay point (E:T ratio) is performed in triplicate. The controls measure spontaneous $^{51}$Cr release wherein no lymphocytes are added to the assays, and 100% release wherein the labeled target cells are lysed with detergent, such as TNEN (10 mM Tris-HCl, 250 mM NaCl, 0.1 mM EDTA and 1% NP-40). After incubating the effector/target cell mixtures for 4 hours, the cells are collected by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm, multiplied by one hundred.

$$\% \text{ cytotoxicity} = \frac{\text{cpm of test sample} - \frac{\text{cpm of spontaneous } ^{51}\text{Cr release}}{\text{cpm of maximal } ^{51}\text{Cr release}} - \text{cpm of spontaneous } ^{51}\text{Cr release}} \times 100$$

In addition, the reactivity of the responding T lymphocytes can also be determined by measuring the levels of cytokines, such as but not limited to tumor necrosis factor, granulocyte-macrophage colony stimulating factor, and interleukin-2, secreted upon stimulation.

5.3.11 Dendritic Cell Differentiation

Differentiation of dendritic cells can be determined by measuring the expression of different markers in the dendritic cells. Such markers include, but are not limited to, interleukin-12, MHC II, CD86, and CD40. The levels of the markers can be determined by any technique well-known to the skilled artisan. For example, mRNA levels can be determined by Northern blot analysis, RT-PCR, or in situ hybridization or any other method known in the art for measuring RNA levels. Protein levels can be determined by Western blot analysis, immunoprecipitation, immunocytochemistry, or any other method for measuring protein levels known in the art (see Short Protocols in Molecular Biology, Ausubel et al. (editors), John Wiley & Sons, Inc., 4$^{th}$ edition, 1999). An increase in the expression of the marker genes indicates the progressed differentiation of the dendritic cells.

The potency of dendritic cells to activate T cells is also an indicator of dendritic cell differentiation.

5.4 Cytostatic Treatment of Tumor Cells

Before administering tumor cells into a patient, the tumor cells have to be inactivated so as to prevent the tumor cells from proliferating. Any technique well-known to the skilled artisan can be used to inactivate the tumor cells. In one embodiment the tumor cells are inactivated by irradiation. Cells can be irradiated at at least 300 rad, 400 rad, 500 rad, 750 rad, 1,000 rad, 2,500 rad, or at least 5,000 rad. Cells can be irradiated with at most 1,000 rad, 2,500 rad, 5,000 rad, 7,500 rad, or at most 10,000 rad. In a preferred embodiment, the tumor cells are irradiated with 3500 rad.

5.5 Activating Immune Cells such as Macrophages, T-Cells, and Neutrophils

Immunologic signaling activity can be tested either in cell culture on various types of cells of the immune system or in an animal model. Accordingly, the fractions, which are obtained from the supernatant as described above, are added either to cells in culture, such as cultures of macrophages, T-cells and neutrophils, or, alternatively, are injected into an animal, preferably a mouse. After a sufficient time period said cells are tested for immunologic activity. This can be. accomplished for example by measuring the expression levels of markers of activation. In the case of macrophages such markers include, but are not limited to, the nitric oxide synthase, iNOS, and the chemokine RANTES. If the activation of T-cells is to be investigated, interferon-gamma (IFN-γ) and interleukin-2 (IL-2) can be used as markers. Expression of the tumor necrosis factor alpha (TNFα) can be used as a marker if neutrophils are used in this assay system. The length of the time period between stimulation and assay of expression of said markers may be changed and depends on the precise experimental conditions. A minimum of experimentation is necessary to establish the assay system to which the invention relates in such a way that it functions optimally. The levels of iNOS, RANTES, IFN-γ, IL-2, and TNFα can be determined by immunoblotting, Northern blotting, RNAse protection assays, immunocytochemistry or similar techniques well known to the skilled artisan. For any of those techniques probes specific to iNOS, RANTES, IFN-γ, IL-2, and TNFα, respectively, have to be employed. Such probes comprise antibodies and antisense RNA molecules. The detection of such probes is well-established in the art.

If an animal model is employed, macrophages, T-cells and neutrophils can be isolated from the animal and subsequently analyzed or, alternatively, expression levels of iNOS, RANTES, IFN-γ, IL-2, and TNFα can be tested in situ by immunohistochemistry or in situ hybridization. For any of those techniques probes specific to iNOS, RANTES, IFN-γ, IL-2, and TNFα, respectively, have to be employed. Such probes comprise antibodies and antisense RNA molecules. The detection of such probes is well established in the art. Quantification and statistical analysis of the data is done by standard methods.

5.5.1 Methods for Stimulating the Immune Response by Inhibiting STAT3 Signaling In another embodiment, based on the regulatory effect of Stat3 on the production of immunologic danger signals and the immune-response, the invention provides methods for stimulating the immune response using antagonists of Stat3 signaling activity. Immunologic danger signals are factors that attract cells of the immune-system to the site of the infection or cancerous growth and activate an immune response. Such immunologic danger signals include, but are not limited to, IFN-γ inducible protein 10 (IP-10), interleukin-6 (IL-6), tumor necrosis factor-alpha (TNFα) and interferon-beta (IFN-13).

In specific embodiments, the invention comprises administering to a patient the supernatant of cells with decreased Stat3 expression and/or function. The invention also encompasses inhibition of Stat3 signaling in the patient locally or systemically to augment the immune response in various diseases. The various embodiments of the invention are described in more detail in the sections below. The goal of any of these embodiments is to increase the concentration of immunologic danger signals either locally or systemically in the patient, thereby augmenting the immune response. Such a strengthening of the patient's own defense system is desirable when the patients natural immune reaction is not sufficient to eliminate the pathogen or the malignant cells. More specifically, some tumors evade immune surveillance by suppressing the expression of immunologic danger signals. The methods of the invention provide an approach to overcome the tumor's ability to evade immune surveillance.

5.5.2 Approaches for Administering the Supernatant of STAT3B Transfected Cells This embodiment of the invention relates to the inhibition of Stat3 signaling in cells such as B 16 melanoma cells by such means as expression of Stat3β, expression of negative regulators of Stat3 signaling as for example PIAS and SOCS, expression of Stat3 antisense nucleotide sequences, administration of in vitro synthesized Stat3 antisense nucleotide sequences, and antibodies specific to Stat3. In the preferred embodiment of the invention, Stat3β is expressed in B16 melanoma cells by means of transfection and supernatant is obtained from said cell culture. The supernatant can then be administered to a patient in order to augment the immune response in various diseases. Such diseases include infectious diseases and various malignancies. The supernatant can be administered by any method known in the art. Some examples of which are described in Section 5.6.4. Said supernatant can be converted into solid form by means such as to lyophilization.

5.5.3 Gene Therapy Approaches to Augment the Immune-Response

In a preferred embodiment, the pharmaceutical of the invention is Stat3β, a dominant negative form of Stat3. Compared to Stat3, Stat3β lacks the C-terminal transactivation domain. Stat3β fails to activate a pIRE containing promoter in transient transfection assays. Instead, co-expression of Stat3β inhibits the transactivation potential of STAT3, thus effectively inhibiting Stat3 activity (Caldenhoven et al. 1996, Journal of Biological Chemistry 271:13221-13227). The dominant negative form of Stat3, Stat3β, can be administered by a gene therapy approach. With this strategy, Stat3β is delivered to the targeted tissue in form of a nucleotide sequence encoding Stat3β under conditions that allow Stat3β expression. In order for the Stat3β gene to be expressed, the gene must be operatively linked to an enhancer/promoter sequence. In order to target only certain organs or tissues, tissue-specific and/or inducible enhancer/promoter sequences can be used. Alternative embodiments of the inventions comprise other inhibitors of Stat3 signaling, such as, but not limited to, the SOCS negative regulatory molecules and the PIAS family of negative regulatory proteins (Starr and Hilton 1999, Bioessays 21:47-52). These factors can also be administered via gene therapy. In order for these genes to be expressed, the respective gene must be operatively linked to an enhancer/promoter sequence. In order to target only certain organs or tissues, tissue-specific and/or inducible enhancer/promoter sequences can be employed. Additionally, the invention relates to suppressing the expression of endogenous Stat3. This can be achieved by administering nucleotide sequences that are in antisense orientation relative to the Stat3 encoding mRNA. Those nucleotide sequences can vary in length from 20 basepairs up to the length of the entire Stat3 cDNA. Antisense nucleotide sequences of different length may differ in their efficacy as drugs, and it may take some experimentation to find the right length to treat the indicated disorder. Such antisense Stat3 nuleotide sequences can be delivered via gene transfer. In order for these antisense Stat3 nucleotide sequences to be expressed, the antisense Stat3 nucleotide sequence must be operatively linked to an enhancer/promoter sequence. For targeting only certain organs or tissues, tissue-specific and/or inducible enhancer/promoter sequences can be employed.

Furthermore, expression of Stat3 can be suppressed by intracellular expression of small RNA therapeutics such as ribozymes. Small RNA therapeutics can be delivered via gene therapy by linking the nucleotide sequences encoding RNA therapeutics operatively to an enhancer/promoter sequence. The invention encompasses the administration of a vector comprising the nucleotide sequence encoding the Stat3 specific ribozyme operatively linked to an enhancer/promoter to a patient by methods described in, thus enhancing the immune response of the patient.

5.6 Therapeutic Methods for Use with the Invention

The present invention encompasses methods for treating or preventing cancer using tumor cells or antigen presenting cells with decreased Stat3 expression or function. The methods provided herein are designed to elicit an immune response against cancer by providing either active or passive immunity against said cancer. As used herein, the phrase "treating or preventing cancer" refers to ameliorating or relieving at least one symptom of cancer. Such symptoms of cancer include, but are not limited to, the appearance of a tumor mass, such as its size, shape, morphology, the rate of tumor growth, or the rate of increase in number of cells, increase in number of tumor masses, or increase in size of tumors or increase rate of metastasis of tumors in a patient. Other symptoms, such as those characteristic of particular cancers, including those paraticular cancers listed in Section 5.8, are well known to the skilled artisan.

5.6.1 Recombinant DNA

In various embodiments of the invention, the Stat3 activity modulator comprises a protein which is encoded by a specific nucleotide sequence. In other embodiments of the invention, the pharmaceutical comprises a nucleotide sequence which is transcribed to generate a biologically active RNA molecule. In even other embodiments of the invention, the Stat3 activity modulator comprises a nucleotide sequence which is to be transcribed and translated. In either case, said nucleotide sequence is inserted into an expression vector for propagation and expression in recombinant cells or in cells of the host in the case of gene therapy.

An expression construct, as used herein, refers to a nucleotide sequence encoding the Stat3 activity modulator, which can be either an RNA molecule or a protein, operably linked to one or more regulatory regions or enhancer/promoter sequences which enables expression of the protein of the invention in an appropriate host cell. "Operably-linked" refers to an association in which the regulatory regions and the nucleotide sequence encoding the Stat3 activity modulator to be expressed are joined and positioned in such a way as to permit transcription, and ultimately, translation.

The regulatory regions necessary for transcription of the Stat3 activity modulator can be provided by the expression vector. In a compatible host-construct system, cellular transcriptional factors, such as RNA polymerase, will bind to the regulatory regions on the expression construct to effect transcription of the Stat3 activity modulator in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5'-non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

Both constitutive and inducible regulatory regions may be used for expression of the Stat3 activity modulator. It may be desirable to use inducible promoters when the conditions optimal for growth of the host cells and the conditions for high level expression of the Stat3 activity modulator are different. Examples of useful regulatory regions are provided below (Section 5.6.3).

In order to attach DNA sequences with regulatory functions, such as promoters, to the sequence encoding the Stat3 activity modulator or to insert the sequence encoding the Stat3 activity modulator into the cloning site of a vector, linkers or adapters providing the appropriate compatible restriction sites may be ligated to the ends of the cDNAs by techniques well known in the art (Wu et al., 1987, Methods in Enzymol 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising a sequence encoding the Stat3 activity modulator operably linked to regulatory regions (enhancer/promoter sequences) can be directly introduced into appropriate host cells for expression and production of the Stat3 activity modulator without further cloning. The expression constructs can also contain DNA sequences that facilitate integration of the sequence encoding the Stat3 activity modulator into the genome of the host cell, e.g., via homologous recombination. In this instance, it is not necessary to employ an expression vector comprising a replication origin suitable for appropriate host cells in order to propagate and express the protein of the invention in the host cells.

A variety of expression vectors may be used in the present invention which include, but are not limited to, plasmids, cosmids, phage, phagemids, or modified viruses. Typically, such expression vectors comprise a functional origin of replication for propagation of the vector in an appropriate host cell, one or more restriction endonuclease sites for insertion of the sequence encoding the Stat3 activity modulator, and one or more selection markers. The expression vector must be used with a compatible host cell which may be derived from a prokaryotic or an eukaryotic organism including but not limited to bacteria, yeasts, insects, mammals, and humans.

Vectors based on *E. coli* are the most popular and versatile systems for high level expression of foreign proteins (Makrides, 1996, Microbiol. Rev. 60:512-538). Non-limiting examples of regulatory regions that can be used for expression in *E. coli* may include but not limited to lac, trp, lpp, phoA, recA, tac, T3, T7 and $\lambda P_L$ (Makrides, 1996, supra). Non-limiting examples of prokaryotic expression vectors may include the λgt vector series such as λgt11 (Huynh et al., 1984 in "DNA Cloning Techniques", Vol. I: A Practical Approach D. Glover, ed.), pp. 49-78, IRL Press, Oxford), and the pET vector series (Studier et al., 1990, Methods Enzymol., 185:60-89). However, a potential drawback of a prokaryotic host-vector system is the inability to perform many of the post-translational processing of mammalian cells. Thus, an eukaryotic host-vector system is preferred, a mammalian host-vector system is more preferred, and a human host-vector system is the most preferred.

For expression of the Stat3 activity modulator in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), β-interferon gene, and hsp70 gene (Williams et al., 1989, Cancer Res. 49:2735-42; Taylor et al., 1990, Mol. Cell Biol., 10:165-75). It may be advantageous to use heat shock promoters or stress promoters to drive expression of the Stat3 activity modulator in recombinant host cells.

In addition, the expression vector may contain selectable or screenable marker genes for initially isolating, identifying or tracking host cells that contain DNA encoding the elected Stat3 activity modulator. For long term, high yield production of the elected Stat3 activity modulator, stable expression in mammalian cells is preferred. A number of selection systems may be used for mammalian cells, including but not limited to the Herpes simplex virus thymidine kinase (Wigler et al., 1977, Cell 11:223), hypoxanthine-guanine phosphoribosyl-transferase (Szybalski and Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150: 1); and hygromycin phosphotransferase (hyg), which confers resistance to hygromycin (Santerre et al., 1984, Gene 30:147). Other selectable markers, such as but not limited to histidinol and Zeocin™ can also be used.

5.6.2 Production of Recombinant Proteins 5.6.2.1 Peptide Tagging

If the Stat3 activity modulator is a protein (hereinafter: the protein of the invention), generating a fusion protein comprising a peptide tag can aid its purification. In various embodiments, such a fusion protein can be made by ligating the nucleotide sequence encoding the protein of the invention to the sequence encoding the peptide tag in the proper reading frame. If genomic sequences are used, care should be taken to ensure that the modified gene remains within the same translational reading frame, uninterrupted by translational stop signals and/or spurious messenger RNA splicing signals.

In a specific embodiment, the peptide tag is fused at its amino terminal to the carboxyl terminal of the protein of the invention. The precise site at which the fusion is made is not critical. The optimal site can be determined by routine experimentation.

A variety of peptide tags known in the art may be used in the modification of the protein of the invention, such as but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220-229), the *E. coli* maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc. Other peptide tags are recognized by specific binding partners and thus facilitate isolation by affinity binding to the binding partner, which is preferably immobilized and/or on a solid support. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

5.6.2.2 Expression Systems and Host Cells

Preferred mammalian host cells include but are not limited to those derived from humans, monkeys and rodents, (see, for example, Kriegler M. in "Gene Transfer and Expression: A Laboratory Manual", New York, Freeman & Co. 1990), such as monkey kidney cell line transformed by SV40 (COS-7, ATCC CRL 1651); human embryonic kidney line (293, 293-EBNA, or 293 cells subcloned for growth in suspension culture, Graham et al., J. Gen. Virol., 36:59, 1977; baby hamster kidney cells (BHK, ATCC CCL 10); chinese hamster ovary-cells-DHFR (CHO, Urlaub and Chasin. Proc. Natl. Acad. Sci. 77; 4216, 1980); mouse sertoli cells (Mather, Biol. Reprod. 23:243-251, 1980); mouse fibroblast cells (NIH-3T3), monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI38, ATCC CCL 75); human liver cells (Hep G2, HB 8065); and mouse mammary tumor cells (MMT 060562, ATCC CCL5 1).

A number of viral-based expression systems may also be utilized with mammalian cells to produce the Stat3 activity modulator. Vectors using DNA virus backbones have been derived from simian virus 40 (SV40) (Hamer et al., 1979, Cell 17:725), adenovirus (Van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts (see, e.g., Logan and Shenk, 1984, Proc. Natl. Acad. Sci. (USA) 81:3655-3659).

Other useful eukaryotic host-vector system may include yeast and insect systems. In yeast, a number of vectors containing constitutive or inducible promoters may be used with *Saccharomyces cerevisiae* (baker's yeast), *Schizosaccharomyces pombe* (fission yeast), *Pichia pastoris*, and *Hansenula polymorpha* (methylotropic yeasts). For a review see, Current Protocols in Molecular Biology, Vol. 2, 1988, Ed. Ausubel et al., Greene Publish. Assoc. & Wiley Interscience, Ch. 13; Grant et al, 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. 11, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathem et al., Cold Spring Harbor Press, Vols. I and II.

In an insect system, Autographa califomica nuclear polyhidrosis virus (AcNPV) a baculovirus, can be used as a vector to express the protein of the invention in *Spodoptera frugiperda* cells. The sequences encoding the protein of the invention may be cloned into non-essential regions (for example the polyhedrin gene) of the virus and placed under control of an AcNPV promoter (for example the polyhedrin promoter). These recombinant viruses are then used to infect host cells in which the inserted DNA is expressed. (See e.g., Smith et al., 1983, J Virol 46:584; Smith, U.S. Pat. No. 4,215,051.)

Any of the cloning and expression vectors described herein may be synthesized and assembled from known DNA sequences by well known techniques in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Expression constructs containing cloned nucleotide sequence encoding the protein of the invention can be introduced into the host cell by a variety of techniques known in the art, including but not limited to, for prokaryotic cells, bacterial transformation (Hanahan, 1985, in DNA Cloning, A Practical Approach, 1:109-136), and for eukaryotic cells, calcium phosphate mediated transfection (Wigler et al., 1977, Cell 11:223-232), liposome-mediated transfection (Schaefer-Ridder et al., 1982, Science 215:166-168), electroporation (Wolff et al., 1987, Proc Natl Acad Sci 84:3344), and microinjection (Cappechi, 1980, Cell 22:479-488).

For long term, high yield production of the properly processed protein of the invention, stable expression in mammalian cells is preferred. Cell lines that stably express protein of the invention may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while the protein of the invention is expressed continuously.

5.6.2.3 Protein Purification

Generally, the protein of the invention can be recovered and purified from recombinant cell cultures by known methods, including ammonium sulfate precipitation, acid extraction, anion or cation exchange chromatography, phosphocellulose chromatography, immunoaffinity chromatography, hydroxyapatite chromatography, and lectin chromatography. Before the protein of the invention can be purified, total protein has to be prepared from the cell culture. This procedure comprises collection, washing and lysis of said cells and is well known to the skilled artisan.

However, the invention provides methods for purification of the protein of the invention which are based on the properties of the peptide tag present on the protein of the invention. One approach is based on specific molecular interactions between a tag and its binding partner. The other approach relies on the immunospecific binding of an antibody to an epitope present on the tag or on the protein which is to be purified. The principle of affinity chromatography well known in the art is generally applicable to both of these approaches.

Described below are several methods based on specific molecular interactions of a tag and its binding partner.

A method that is generally applicable to purifying protein of the invention that are fused to the constant regions of immunoglobulin is protein A affinity chromatography, a technique that is well known in the art. Staphylococcus protein A is a 42 kD polypeptide that binds specifically to a region located between the second and third constant regions of heavy chain immunoglobulins. Because of the Fc domains of different classes, subclasses and species of immunoglobulins, affinity of protein A for human Fc regions is strong, but may vary with other species. Subclasses that are less preferred include human IgG-3, and most rat subclasses. For certain subclasses, protein G (of Streptococci) may be used in place of protein A in the purification. Protein-A sepharose (Pharmacia or Biorad) is a commonly used solid phase for affinity purification of antibodies, and can be used essentially in the same manner for the purification of the protein of the invention fused to an immunoglobulin Fc fragment. Bound protein of the invention can be eluted by various buffer systems known in the art, including a succession of citrate, acetate and glycine-HCl buffers which gradually lowers the pH. This method is less preferred if the recombinant cells also produce antibodies which will be copurified with the protein of the invention. See, for example, Langone, 1982, J. Immunol. meth. 51:3; Wilchek et al., 1982, Biochem. Intl. 4:629; Sjobring et al., 1991, J. Biol. Chem. 26:399; page 617-618, in Antibodies A Laboratory Manual, edited by Harlow and Lane, Cold Spring Harbor laboratory, 1988.

Alternatively, a polyhistidine tag may be used, in which case, the protein of the invention can be purified by metal chelate chromatography. The polyhistidine tag, usually a sequence of six histidines, has a high affinity for divalent metal ions, such as nickel ions ($Ni^{2+}$), which can be immobilized on a solid phase, such as nitrilotriacetic acid-matrices. Polyhistidine has a well characterized affinity for $Ni^{2+}$-NTA-agarose, and can be eluted with either of two mild treatments: imidazole (0.1-0.2 M) will effectively compete with the resin for binding sites; or lowering the pH just below 6.0 will protonate the histidine sidechains and disrupt the binding. The purification method comprises loading the cell culture lysate onto the $Ni^{2+}$-NTA-agarose column, washing the contaminants through, and eluting the protein of the invention with imidazole or weak acid. $Ni^{2+}$-NTA-agarose can be obtained from commercial suppliers such as Sigma (St. Louis) and Qiagen. Antibodies that recognize the polyhistidine tag are also available which can be used to detect and quantitate the protein of the invention.

Another exemplary peptide tag that can be used is the glutathione-S-transferase (GST) sequence, originally cloned from the helminth, *Schistosoma japonicum*. In general, a protein of the invention-GST fusion expressed in a prokaryotic host cell, such as *E. coli*, can be purified from the cell culture lysate by absorption with glutathione agarose beads, followed by elution in the presence of free reduced glutathione at neutral pH. Since GST is known to form dimers under certain conditions, dimeric protein of the invention may be obtained. See, Smith, 1993, Methods Mol. Cell Bio. 4:220-229.

Another useful peptide tag that can be used is the maltose binding protein (MBP) of *E. coli*, which is encoded by the malE gene. The protein of the invention binds to amylose resin while contaminants are washed away. The bound protein of the invention-MBP fusion is eluted from the amylose resin by maltose. See, for example, Guan et al., 1987, Gene 67:21-30.

The second approach for purifying the protein of the invention is applicable to peptide tags that contain an epitope for which polyclonal or monoclonal antibodies are available. It is also applicable if polyclonal or monoclonal antibodies specific to the protein of the invention are available. Various methods known in the art for purification of protein by immunospecific binding, such as immunoaffinity chromatography, and immunoprecipitation, can be used. See, for example, Chapter 13 in Antibodies A Laboratory Manual, edited by Harlow and Lane, Cold Spring Harbor laboratory, 1988; and Chapter 8, Sections I and II, in Current Protocols in Immunology, ed. by Coligan et al., John Wiley, 1991; the disclosure of which are both incorporated by reference herein.

5.6.3 Antibodies to STAT3 and Derivatives

According to the invention, Stat3, its fragments or other derivatives, or analogs thereof, may be used as an immunogen to generate antibodies which immunospecifically bind such an immunogen. Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Examples of immunologically active portions of immunoglobulin molecules include F(ab) and F(ab')2 fragments which can be generated by treating the antibody with an enzyme such as pepsin or papain. In a specific embodiment, antibodies to a human Stat3 protein are produced. In another embodiment, antibodies to a domain of Stat3 are produced.

Various procedures known in the art may be used for the production of polyclonal antibodies to Stat3 or derivative or analog. In a particular embodiment, rabbit polyclonal antibodies to an epitope of Stat3 encoded by a sequence or fragment of SEQ ID NO: 2, or a subsequence thereof, can be obtained. For the production of antibody, various host animals can be immunized by injection with the native Stat3, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed toward an Stat3 sequence or analog thereof, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al, 1985, in Monoclonal Antibodies and Cancer Therapy, Alan R. Liss, pp. 77-96). In fact, according to the invention, techniques developed for the production of "chimeric antibodies" (Morrison et al, 1984, Proc. Natl. Acad. Sci. U.S.A. 81:6851-6855; Neuberger et al, 1984, Nature 312:604-608; Takeda et al., 1985, Nature 314:452-454) by splicing the genes from a mouse antibody molecule specific for Stat3 together with genes from a human antibody molecule of appropriate biological activity can be used; such antibodies are within the scope of this invention.

According to the invention, techniques described for the production of single chain antibodies (U.S. Pat. No. 4,946,778) can be adapted to produce Stat3-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for Stat3s, derivatives, or analogs.

Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a STAT, e.g., the transcriptional activation domain, DNA binding domain, dimerization domain, SH2 domain, or SH3 domain, one may assay generated hybridomas for a product which binds to a Stat3 fragment containing such domain. For selection of an antibody that specifically binds a first Stat3 homolog but which does not specifically bind a different Stat3 homolog, one can select on the basis of positive binding to the first Stat3 homolog and a lack of binding to the second Stat3 homolog.

Antibodies specific to a domain of Stat3 are also provided, such as to a transcriptional activation domain, DNA binding domain, a dimerization domain, SH2 domain, SH3 domain.

The foregoing antibodies can be used in methods known in the art relating to the localization and activity of the Stat3 sequences of the invention, e.g., for imaging these proteins, measuring levels thereof in appropriate physiological samples, in diagnostic methods, etc.

In another embodiment of the invention (see infra), anti-Stat3 antibodies and fragments thereof containing the binding domain are used as therapeutics.

Anti-Stat3 antibodies can be obtained from Santa Cruz Biotechnology, Inc. (Santa Cruz, Calif.), Research Diagnostics, Inc. (Flanders, N.J.) or Zymed Laboratories (South San Francisco, Calif.). Alternatively, anti-Stat3 antibodies antibodies can be produced by any method known in the art for the synthesis of antibodies, in particular, by chemical synthesis or preferably, by recombinant expression techniques.

5.7 Pharmaceutical Formulations and Modes of Administration

In a preferred aspect, a pharmaceutical of the invention comprises a substantially urified protein, nucleic acid, chemical, cell or mixture of cells (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Various delivery systems are known and can be used to administer the pharmaceutical of the invention, e.g., encapsulation in liposomes, microparticles, microcapsules, receptor-mediated endocytosis (see, e.g., Wu and Wu, 1987, J. Biol. Chem. 262:4429-4432), construction of a nucleic acid as part of a retroviral or other vector, etc. Methods of introduction include but are not limited to intradermal, intramuscular, intraperitoneal, intravenous, subcutaneous, intranasal, epidural, and oral routes. Nucleic acids and proteins of the invention may be administered by any convenient route, for example by infusion or bolus injection, by absorption through epithelial or mucocutaneous linings (e.g., oral mucosa, rectal and intestinal mucosa, etc.) and may be administered together with other biologically active agents such as chemotherapeutic agents. Administration can be systemic or local.

In a specific embodiment, it may be desirable to administer the nucleic acid or protein of the invention by injection, by means of a catheter, by means of a suppository, or by means of an implant, said implant being of a porous, non-porous, or gelatinous material, including a membrane, such as a sialastic membrane, or a fiber. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527-1533; Treat et al., 1989, in Liposomes in the Therapy of Infectious Disease and Cancer, Lopez-Berestein and Fidler (eds.), Liss, N.Y., pp. 353-365; Lopez-Berestein, ibid., pp. 317-327; see generally, ibid.)

In yet another embodiment, the compound or composition can be delivered in a controlled release system. In one embodiment, a pump may be used (see Langer, supra; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105).

Other controlled release systems are discussed in the review by Langer, 1990, Science 249:1527-1533.

In a specific embodiment where a nucleic acid of the invention is administered, the nucleic acid can be administered in vivo to promote expression of its encoded protein or RNA molecule, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination. For a more detailed description of gene therapy approaches, see Section 5.6.3.

As alluded to above, the present invention also provides pharmaceutical compositions (pharmaceuticals of the invention). Such compositions comprise a therapeutically effective amount of a nucleic acid, chemical or protein of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein of the invention, preferably in purified form, together with a suitable amount of carrier so as to provide the form for proper administration to the patient. The formulation should suit the mode of administration.

In a preferred embodiment, the pharmaceutical of the invention is formulated in accordance with routine procedures as a pharmaceutical composition adapted for intravenous administration to human beings. Typically, compositions for intravenous administration are solutions in sterile isotonic aqueous buffer. Where necessary, the pharmaceutical of the invention may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical of the invention is to be administered by infusion, it can be dispensed with an infusion bottle containing sterile pharmaceutical grade water or saline. Where the pharmaceutical of the invention is administered by injection, an ampoule of sterile water for injection or saline can be provided so that the ingredients may be mixed prior to administration.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The amount of the nucleic acid or protein of the invention which will be effective in the treatment or prevention of the indicated disease can be determined by standard clinical techniques. In addition, in vitro assays may optionally be employed to help identify optimal dosage ranges. The precise dose to be employed in the formulation will also depend on the route of administration, and the stage of indicated disease, and should be decided according to the judgment of the practitioner and each patient's circumstances. Effective doses may be extrapolated from dose-response curves derived from in vitro or animal model test systems.

The subject can be an animal, including, but not limited, a cow, horse, sheep, pig, chicken, turkey, quail, cat, dog, mouse, rat, rabbit, and a guinea pig. In certain embodiments, the subject is a mammal. In one embodiment, the subject is a human.

5.7.1 Administration of Cells

Cells, such as tumor cells, activated T cells, and/or antigen-presenting cells, can be reinfused into a subject systemically, preferably intradermally, by conventional clinical procedures. In one embodiment, cells are reinfused by systemic administration into the autologous patient. The cells can be administered one time or repeatedly. If different cell types are to be administered, the different cells can be administered concurrently with each other or subsequent to each other.

In certain embodiments, at least $5\times10^5$, at least $1\times10^6$, at least $5\times10^6$, at least $1\times10^7$, at least $5\times10^7$, at least $1\times10^8$, at least $5\times10^8$, at least $1\times10^9$, at least $5\times10^9$, at least $1\times10^{10}$, at least $5\times10^1$, or at least $1\times10^{11}$ cells, at least $5\times10^{11}$, or at least $1\times10^{12}$ tumor cells are administered into a subject. In certain embodiments, at most $5\times10^5$, at most $1\times10^6$, at most $5\times10^6$, at most $1\times10^7$, at most $5\times10^7$, at most $1\times10^8$, at most $5\times10^8$, at most $1\times10^9$, at most $5\times10^9$, at most $1\times10^{10}$, at most $5\times10^{10}$, or at most $1\times10^{11}$ cells, at most $5\times10^{11}$, or at most $1\times10^{12}$ tumor cells are administered into a subject.

In certain other embodiments, at least $5\times10^5$, at least $1\times10^6$, at least $5\times10^6$, at least $1\times10^7$, at least $5\times10^7$, at least $1\times10^8$, at least $5\times10^8$, at least $1\times10^9$, at least $5\times10^9$, at least $1\times10^{10}$, at least $5\times10^{10}$, or at least $1\times10^{11}$ cells, at least $5\times10^{11}$, or at least $1\times10^{12}$ activated T cells are administered into a subject. In certain embodiments, at most $5\times10^5$, at most $1\times10^6$, at most $5\times10^6$, at most $1\times10^7$, at most $5\times10^7$, at most $1\times10^8$, at most $5\times10^8$, at most $1\times10^9$, at most $5\times10^9$, at most $1\times10^{10}$, at most $5\times10^{10}$, or at most $1\times10^{11}$ cells, at most $5\times10^{11}$, or at most $1\times10^{12}$ activated T cells are administered into a subject.

In certain other embodiments, at least $5\times10^5$, at least $1\times10^6$, at least $5\times10^6$, at least $1\times10^7$, at least $5\times10^7$, at least $1\times10^8$, at least $5\times10^8$, at least $1\times10^9$, at least $5\times10^9$, at least $1\times10^{10}$, at least $5\times10^{10}$, or at least $1\times10^{11}$ cells, at least $5\times10^{11}$, or at least $1\times10^{12}$ differentiated dendritic cells are administered into a subject. In certain embodiments, at most $5\times10^5$, at inost $1\times10^6$, at most $5\times10^6$, at most $1\times10^7$, at most $5\times10^7$, at most $1\times10^8$, at most $5\times10^8$, at most $1\times10^9$, at most $5\times10^9$, at most $1\times10^{10}$, at most $5\times10^{10}$, or at most $1\times10^{11}$ cells, at most $5\times10^{11}$, or at most $1\times10^{12}$ differentiated dendritic cells are administered into a subject.

5.8 Target Diseases and Disorders

With respect to specific proliferative and oncogenic disease, the diseases that can be treated or prevented by the methods of the present invention include, but are not limited to: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

As is described hereinbelow, the studies that were performed by the inventors herein are standard, universally-accepted tests in animal models predictive of prophylactic and therapeutic benefit.

6. EXAMPLES

6.1 Regulation of the Innate and Adaptive Immune Responses by STAT3 Signaling in Tumor Cells Recent studies in genetically-deficient mice demonstrate that multiple components of both the innate and adaptive immune system can act as extrinsic tumor suppressors (Kaplan et al. 1998 Immunology 95: 7556-7561, Shankaran et al., 2001, Nature 410: 1107). Indeed, tissue disruption, such as that associated with invasion and metastatic spread of cancer, can stimulate pro-inflammatory signals similar to pathogen infection, which activates antigen presenting cells, leading to antigen-specific immune responses. The immune system, however, is generally tolerant to established cancers (Fuchs, et al. 1996, Semin. in Immunol. 8: 271-280, Pardoll, 1998, Nat Med 4: 525-531), suggesting that the cancers develop mechanisms to inhibit elaboration and/or sensing of immunologic danger signals.

In this example, the role of Stat3 activation in blocking the initiation of antitumor immunity is addressed. Stat3 represents an interesting potential negative regulator of inflammatory responses as mice devoid of the Stat3 gene in macrophages and neutrophils produce elevated levels of pro-inflammatory cytokines upon LPS stimulation, leading to development of chronic enterocolitis (Takeda et al., 1999, Immunity 10: 39-49). Stat3 is a common point of convergence for oncogenic tyrosine kinases and constitutively-activated Stat3 enhances tumor cell proliferation and prevents apoptosis (Catlett-Falcone et al., 1999, Immunity 10:105-115; Grandis et al., 2000, Proc Nat Acad Sci USA 97: 4227-

4232, Bromberg et al., 1999, Cell 98: 295-303, Bowman et al., 2001, Proc Nat Acad Sci USA 98: 7319-7324).

Constitutively activated Stat3, which is inducible by numerous oncogenic pathways and found in greater than 50% of diverse cancers (Bowman et al., 2000, Oncogene 19: 2474-2488; Bromberg et al, 2000, Oncogene 19: 2468-2473; Catlett-Falcone et al., 1999, Immunity 10: 105-115; Grandis et al., 2000, Proc Nat Acad Sci USA 97: 4227-4232), suppresses tumor expression of pro-inflammatory mediators, and in parallel induces production of factors that inhibit functional differentiation of dendritic cells (DCs). Interrupting Stat3 signaling in tumor cells enhances expression of several pro-inflammatory cytokines and chemokines that activate cellular components of innate immunity as well as DCs, resulting in stimulation of antigen-specific T cells both in vitro and in vivo. Conversely, transformation of 3T3 fibroblasts with v-Src, which signals through Stat3, (Yu et al., 1995, Science 269: 81-83), or enforced expression of a constitutively-activated Stat3 protein, Stat3C (Bromberg et al., 1999, Cell 98: 295-303), inhibits the expression of induced pro-inflammatory mediators. Further, the Example shows that transformation by either v-Src or Stat3C induces elaboration of factors, one of which is VEGF, that inhibit functional differentiation of DCs. The presented findings demonstrate that immune evasion likely occurs at the early stages of cancer development via activation of Stat3, which inhibits both the production and sensing of inflammatory signals critical for eliciting innate and adaptive immunity.

6.2 Methods

Cell Lines and Mice

BALB/c3T3 fibroblasts and v-Src-transformed BALB/c3T3 cells were grown in DMEM supplemented with 5% calf serum. B16 melanoma, CT26 and SCK mammary carcinoma cell lines were grown in RPMI medium supplemented with 10% fetal bovine serum. Female, 6-8 weeks old, C57BL/6 and BALB/c mice were purchased from the National Cancer Institute (Fredrick, Md.). TCR transgenic mice expressing an $\alpha/\beta$ TCR specific for amino acids 110-120 from influenza hemagglutinin (HA) presented by I-E$^d$ (6.5) were the gift of Dr. Harald von Boehmer, Harvard University. Mice were housed in American Association for Accreditation of Laboratory Animal Care-approved, specific pathogen- and viral antibody-free facilities located at the H. Lee Moffitt Cancer Center & Research Institute and Oncology Department, Johns Hopkins University School of Medicine.

Transfection

Transfection of murine tumor cells with either plasmid expression vectors and oligonucleotidets were carried out as previously described (Niu et al., 2002, Oncogene, supra).

Electrophoretic Mobility Shift Assays (EMSA) and Western Blot Analysis

EMSA and Western blot analysis to detect Stat3 DNA-binding activity and protein levels, respectively, were performed as previously described (Turkson et al., 1998, Mol. Cell. Biol. 18: 2545-2552).

Retroviral Transduction of BALB/c3T3 and BALB/c3T3v-Src

Stable cell lines producing high titer MSCV retrovirus encoding Stat3C or Stat3D (dominant-negative) were kindly provided by Dr. D. Link (University of Washington; McLemore, M. L., et al 2001 *Immunity* 14, 193-204). Supernatants from these cell lines were used to infect BALB/c3T3 or BALB/c3T3v-Src cells. Two to three times of infection were routinely performed to achieve nearly 100% transduction efficiency as indicated by green florescence. The presence of Stat3C or Stat3D expression was confirmed by Stat3 DNA-binding assays.

RNase Protection Assays (RPA)

Total RNA isolation and RPAs were performed as previously described (Niu, G., et al., 2001, Cancer Res. 61, 3276-3280). For B16 cells, mCK-1b, mCK-2b, mCK3b and mCK-5 multi-template probes (PharMingen) were used. For SCK, CT26, BALBc/3T3 cells and its derivatives, only mCD3b and mCK5 were used in the RPAs.

Probes Included in the Templates:

mCK-1b: IL-4, IL-5, IL-10, IL-13, IL-15, IL-9, IL-2, IL-3, IFNg; mCK-2b: IL-12p35, IL-12p40, IL-10, IL-1a, IL-1b, IL-IRa, IGIF, IL-6, IFNg, MIF; mCK-3b: LTb, TNFa, IL-6, IFNg, IFNb, TGFb1, TGFb2, TGFb3, MIF; mCK-5: Ltn, RANTES, Eoxtaxin, MIP1a, MIP1b, IP-10, MCP-11, TCA-3.

In vivo Experiments

To test if Stat3-interrupted tumor cells could activate tumor antigen-specific T cells in vivo, B16 or CT26 tumor cells were transiently transfected with either GFP or Stat3β vectors. B16 cells or CT26 tumor cells transduced by GM-CSF expression vector (Dranoff et al, 1993, Proc Natl Acad Sci USA 90:3539-3543) were also included in the experiments. Various groups of tumor cells ($1 \times 10^6$/mouse) were then irradiated (4,000 Rads) and injected s.c. into C57BL mice (B16 cells) or BALB/c mice (CT26 cells) twice a week for to two weeks. Two weeks after last injection, splenocytes were prepared from these mice and used in IFNg ELISPOT assays. To determine if blocking Stat3 signaling in tumors would attract/activate immune cells, B16 tumors were allowed to grow until about 5 mm in diameter. Gene therapy with either the GFP control empty vector or Stat3β expression vector was carried out as previously reported, (Niu, G., et al. 1999 Cancer Res 59, 5059-5063). Tissue sections from control vector-treated and Stat3b-treated tumors were stained with Mac-3 antibody (PharMingen) for detection of macrophages, anti-CD3e (Transduction Laboratories) for T cells or Giemsa staining for detecting neutrophils.

Enzyme-linked Immunospot (ELISPOT) Assays

ELISPOT assays were essentially carried out as described (Lu, Z., et al. 2000 J. Exp. Med. 191, 541-550), except different antigen peptides were used. Splenocytes prepared from mice receiving irradiated, transfected tumor cells were incubated in medium ±10 mg/ml of either TRP2$_{181-188}$ peptide (for B16 tumor cells) or AH1 peptide (for CT26 tumor cells) for 48 h.

Bone Marrow Progenitor Cells and Functional Assays

Preparation of bone marrow progenitor cells (BMPCs) and generation of bone marrow-derived mature DCs were carried out according to a previously described protocol (Lu et al., 2000, J. Exp. Med. 191: 541-550). Relatively mature DCs were obtained by incubating, BMPCs in medium containing GM-CSF and IL-4 for 6 days. Relatively mature DCs were then incubated in DC medium supplemented with 1:1 with supernatants from B16 tumor cells tranfected with no DNA, GFP control empty vector or Stat3β expression vector. Following 48 hours culture, suspension cells were collected and analyzed for IL-12 secretion by ELISA (R & D) and expression of DC-surface markers (CD86, CD40 and MHC Class II) by flow cytometry. All antibodies were purchased from PharMingen and surface expression was analyzed using a FACScan cytofluorometer (Becton Dickinson) as previously described, (Lu et al., 2000, supra). For DC differentiation experiments, BMPCs were cultured in DC medium supplemented with 20 to 30% of supernatants from 3T3 variants or B16 transfectants from day 0. Fresh medium supplemented with supernatants was added to the culture every other day until day 6. To examine the effects of the supernatants on DC functional differentiation, cells generated from bone marrow progenitors were incubated overnight with 1 mg/ml ovalbumin (OVA) (Sigma) and used to stimulate naïve T cells isolated from lymph nodes of syngeneic mice. T-cell proliferation was measured by [$^3$H]-thymidine incorporation over 18 hours.

Enrichment of CD4$^+$ T Cells for Antigen-specific Proliferation and IL-2 Production Assays Enrichment of CD4+ T cells from CD4$^+$ TCR Tg mice (6.5) was performed as described, (Lu et al., 2000, supra). Twice enriched CD4+ T cells were 95-98% pure with 45-50% displaying 6.5$^+$CD4$^+$ as determined by FACS. analysis. Proliferation assays and IL-2 ELISA in response to $HA_{110}$-120 peptide were carried as previously reported (Lu et al., 2000, supra).

6.3 Results

Figure 1B:
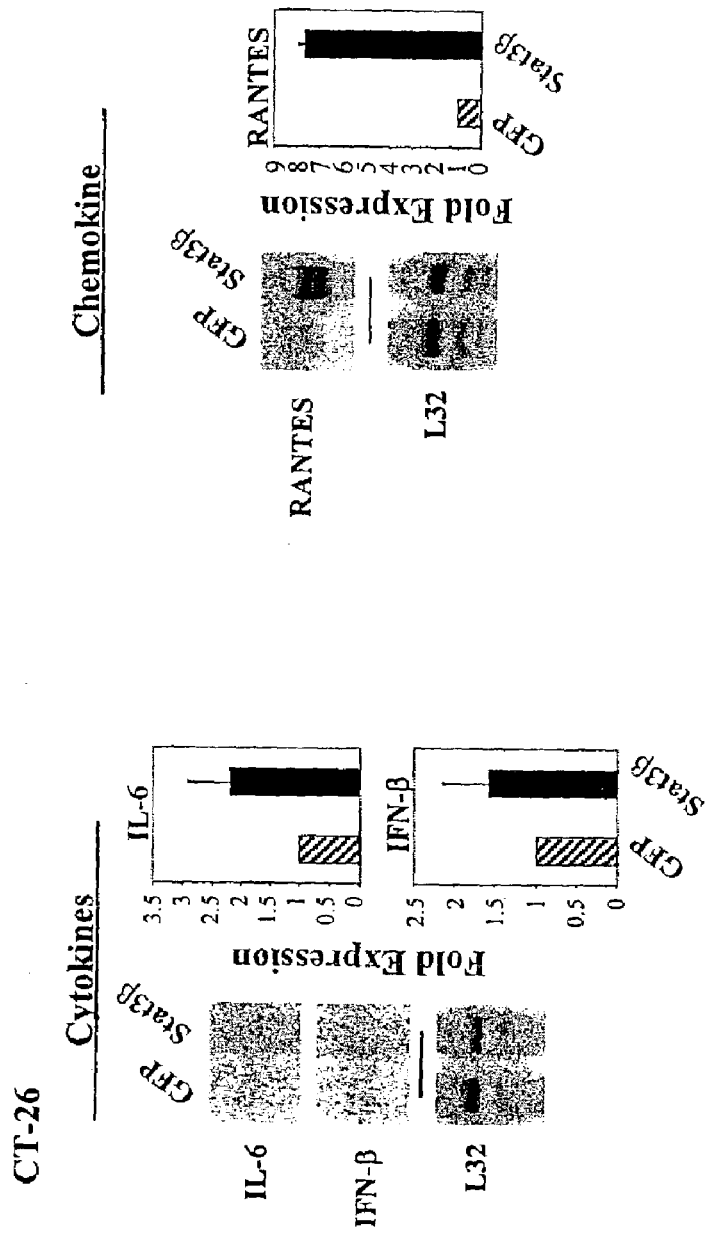
Figure 1C:
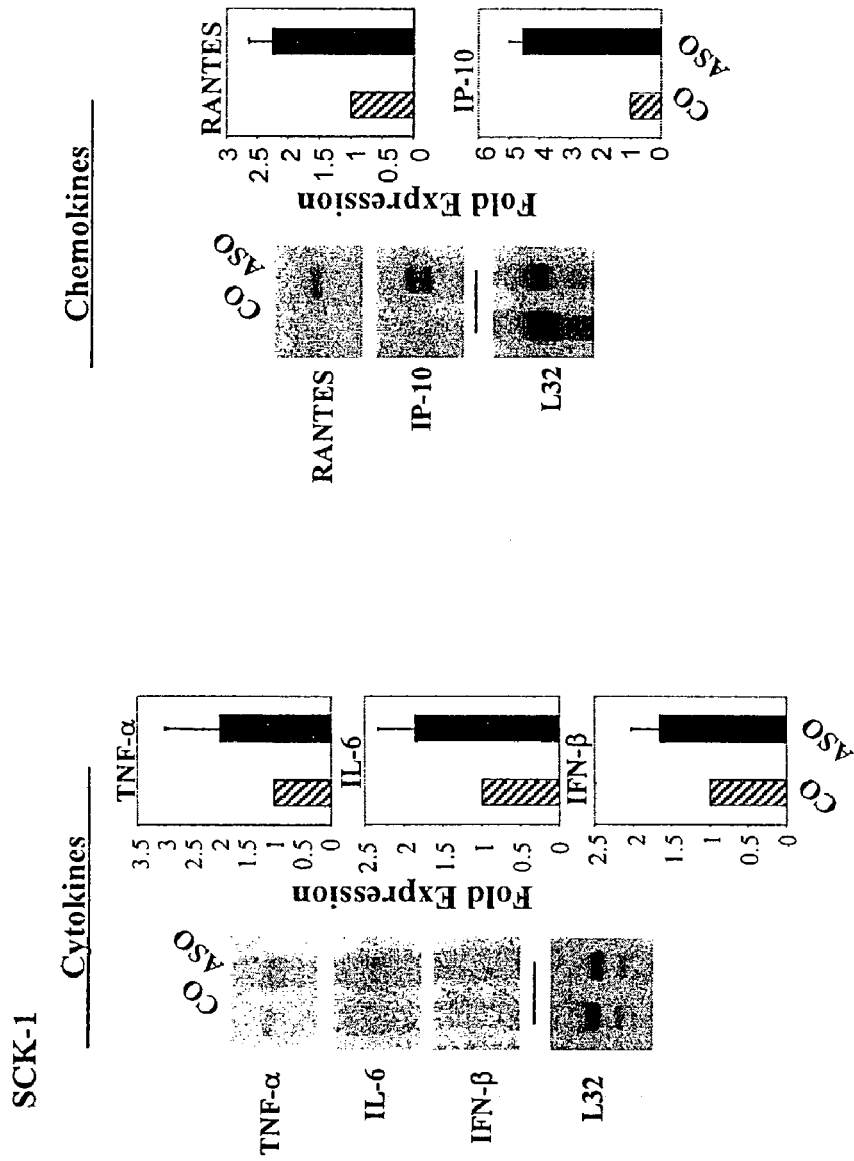

To investigate whether constitutive activation of Stat3 has an inhibitory effect on generation of immunologic danger signals, Stat3 signaling in tumor cells was disrupted by transfecting either a dominant-negative variant of Stat3, designated Stat3 β (Catlett-Falcone et al., 1999, Immunity 10: 105-115), or an anti-sense Stat3 oligonucleotide, (Niu et al., 2002, Oncogene, supra). As with human tumors, a majority of murine tumor cell lines display constitutively activated Stat3 (Bowman et al., 2000, Oncogne 19: 2474-2488, Niu et al., 2002, Oncogene, supra, Niu et al., 1999 Cancer Res 59: 5059-5063). Consistent with previous studies (Niu et al., 2002, Oncogene supra), transfecting either Stat3β expression vector or anti-sense Stat3 oligonucleotide into these murine tumor cells resulted in inhibition of Stat3 DNA-binding activity (data not shown). RNase protection assays (RPA) using multi-template RNA probes indicated that expression of the pro-inflammatory cytokines, IFNγ, TNF-<, IL-6 and the chemokines, RANTES and IP-10, was significantly elevated in B16 melanoma cells transfected with either Stat3β or the anti-sense Stat3 oligonucleotide (FIG. 1a). The autoradiograms in FIG. 1a are representative of three independent experiments. The adjacent histograms represent the means of three experiments normalized to RNA expression of L32 and GAPDH. The up-regulation of these pro-inflammatory mediators was specific, since no increase in the expression of many other genes, including IL-4 and IL-10, was detected (see complete list of cytokine and chemokine RNAs tested in Methods). Because interrupting Stat3 signaling induces growth arrest and apoptosis of B16 cells (Nui et al. 2001, *Cancer Res* 61: 3276-3280), RNA was prepared before the initiation of any apoptotic morphologic changes. Moreover, Applicants examined the effects of apoptosis-inducing doses of UV irradiation on cytokine and chemokine RNA expression. As shown in FIG. 1a, UV irradiation had no detectable effects on the expression of the indicated cytokins/chemokines, suggesting that their induction after Stat3 blockade was not a general response to an apoptotic stimulus. The expression of pro-inflammatory mediators is not specific to B16 melanoma cells. Interruption of Stat3 signaling in CT26 murine tumor cell lines with constitutive Stat3 activity (Niu, G. et al., 2002, Oncogene 21(46): 7001-10) similarly induced expression of these cytokines and chemokines (FIG. 1b,c). For the data represented in FIG. 1b and c, the relative levels of RNA were determined and quantified as in FIG. 1a. The absence of IP-10 in the CT-26 tumor cells is caused by a nucleotide substitution in the ip-10 gene of Balb/c mice resulting in incomplete RNA:RNA hybridization facilitating RNA degradation under experimental conditions. These findings are consistent with the notion that constitutive Stat3 signaling in tumors inhibits the expression of immunologic danger signals.

Figure 1D:
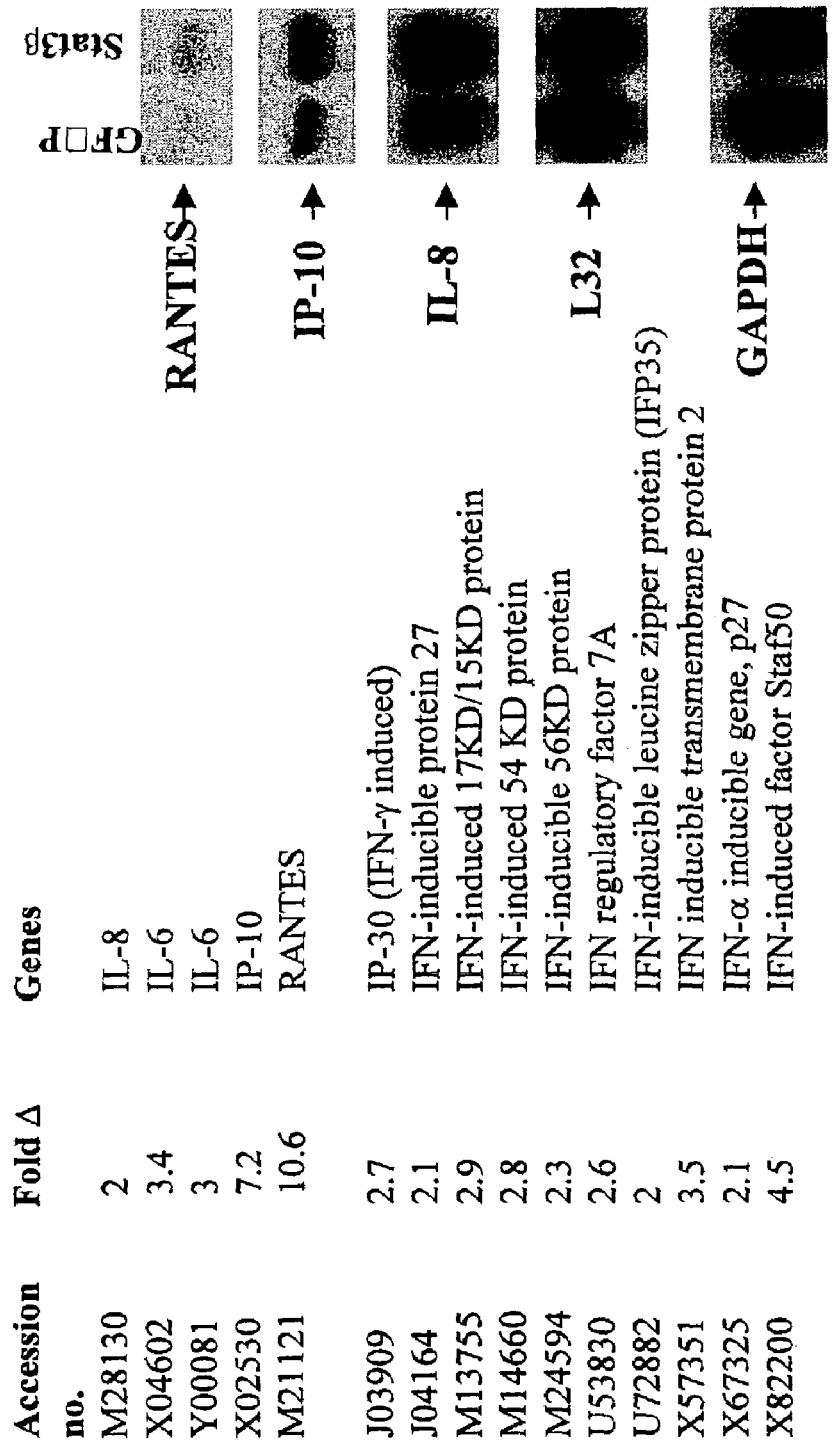

It was next determined whether blocking Stat3 signaling in human tumor cells would also result in expression of pro-inflammatory mediators. Human melanoma A2058 cells, which display Stat3 activity, were subjected to transient transfection of either the GFP control vector or a Stat3β expression vector. Microarray analysis and RNase protection assay of these transfected cells indicated that blocking Stat3 in human tumor cells could also lead to expression of pro-inflammatory mediators (FIG. 1d). Interestingly, a large proportion of the genes activated by Stat3-blockade are IFN inducible, suggesting that Stat3 activity opposes IFN/Stat1 signaling.

Figure 2A:
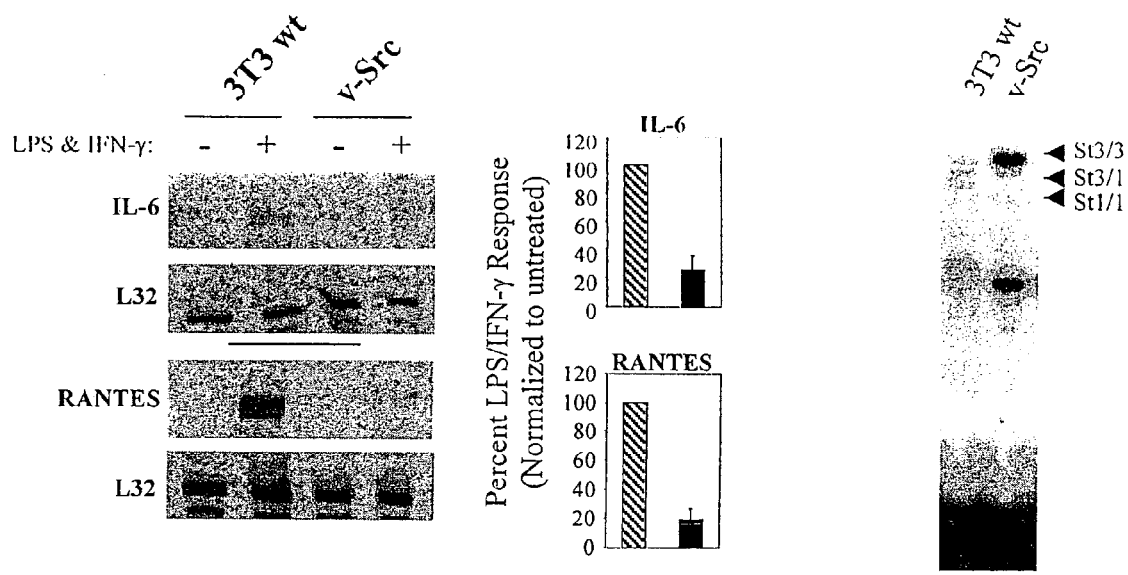
Figure 2B:
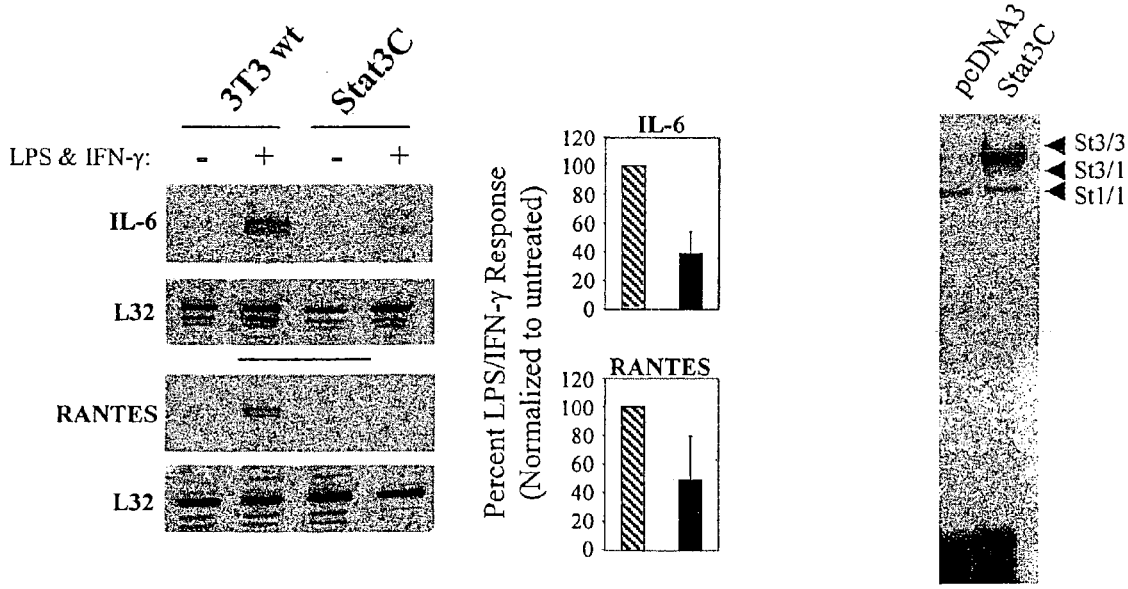

To further explore the role of Stat3 in down-regulating the expression of inflammatory mediators, Applicants asked whether constitutive Stat3 activity could inhibit induced expression of pro-inflammatory cytokines and chemokines. Treatment of normal BALB/c 3T3 fibroblasts, which lack constitutively-activated Stat3, with IFNγ and LPS resulted in up-regulation of IL-6 and RANTES (FIG. 2a). The autoradiograms in FIG. 2a are representative of three independent RPAs. The adjacent histograms represent the means of three experiments normalized to RNA expression of L32 and GAPDH. Stat3 activation was induced in BALB/c 3T3 cells by two independent approaches transformation with v-Src and enforced expression of a constitutively-activated Stat3 mutant, Stat3C (Bromberg et al., 1999, Cell 98: 295-303). As shown in FIG. 2a, v-Src transformation resulted in Stat3 activation and inhibition of cytokine/chemokine induction in 3T3 fibroblasts. Similarly, Stat3C-transfected 3T3 cells exhibited increased Stat3 DNA-binding activity and decreased IL-6 and RANTES RNA expression upon stimulation with LPS and IFNγ when compared to 3T3 cells transfected with a control empty vector (pcDNA3) (FIG. 2b).

These results show that Stat3 activation can inhibit expression of cytokine/chemokine induced by IFNγ/LPS, which signal through Stat1. Together with our findings that blocking Stat3 signaling in cancer cells leads to expression of genes inducible by IFNs and Stat1 activation, data shown here suggest that Stat3 activity antagonizes the pro-inflammatory effects of Stat1. The ability of persistent Stat3 activity in opposing the pro-apoptotic effects of activated Stat1 has been demonstrated previously (Shen et al., 2001, Proc. Natl. Acad. Sci. U S A 98: 1543-1548).

Figures 3A, 3B, 3C:
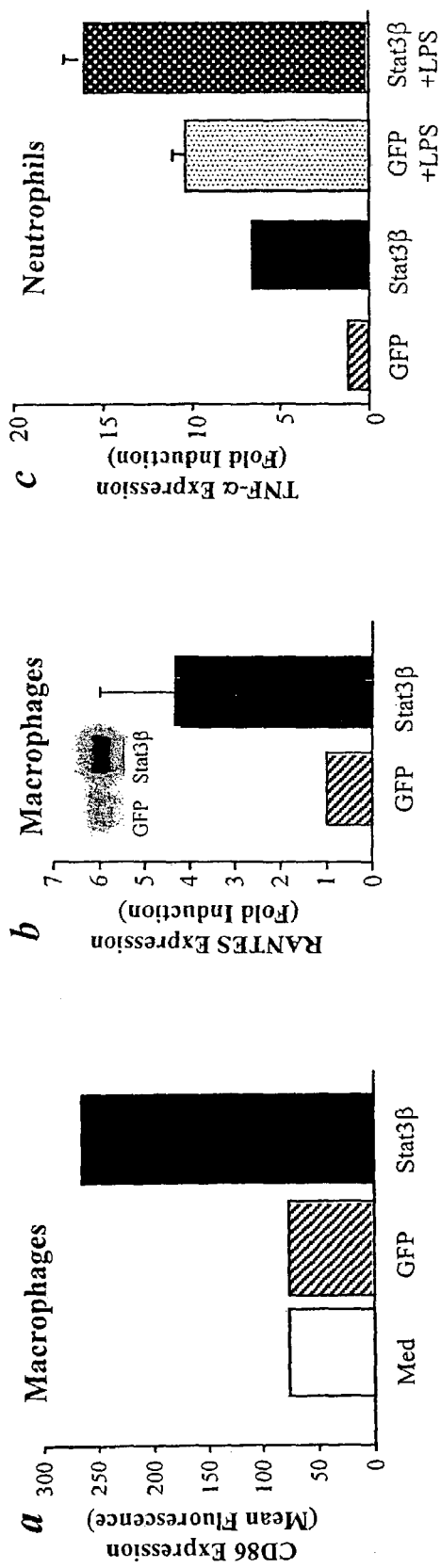
Figure 3D:
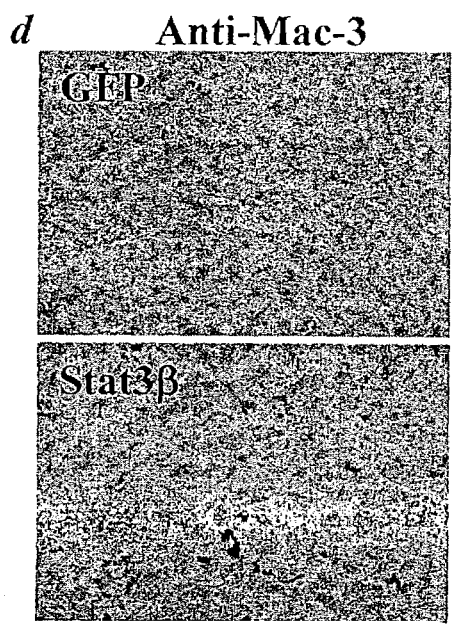
Figure 3E:
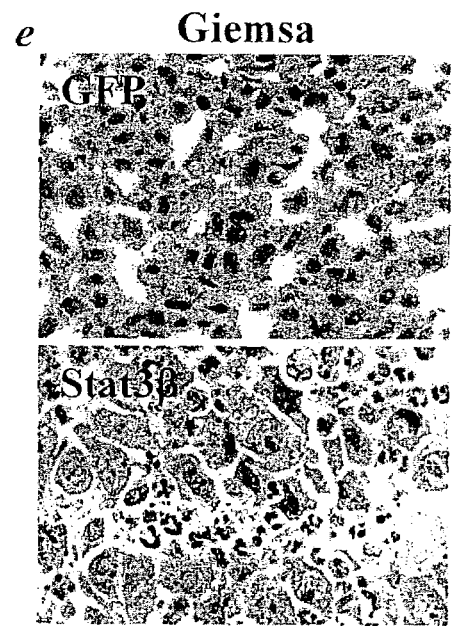
Figure 3F:
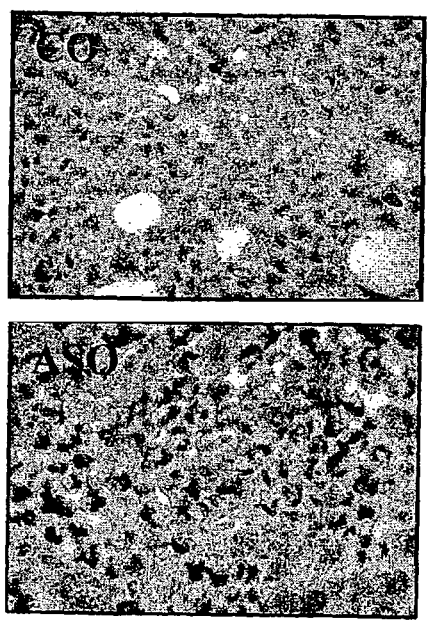

How the inflammatory factors, both defined and undefined, from Stat3-disrrupted tumor cells might affect the innate immune response was next evaluated. Resident peritoneal macrophages treated with supernatants from Stat3β-transfected B16 cells displayed increased expression of CD86 and RANTES (FIG. 3a, b). Data shown in FIG. 3a represent one of three experiments. Quantification of RNA levels in FIG. 3b was based on three experiments. It was also found that the supernatant derived from Stat3β-transfected B16 cells was capable of stimulating TNF-α production by neutrophils (FIG. 3c). These results demonstrate that the pro-inflammatory mediators, including cytokines/chemokines induced by interrupting Stat3 signaling in tumor cells, initiate an amplifying cascade of pro-inflammatory signals and tumoricidal effectors. The question whether disrupting Stat3 signaling in tumor cells could activate innate immune cells in vivo was also examined. Gene transfer of Stat3β into established B16 tumors resulted in infiltration of macrophages (FIG. 3d) and neutrophils (FIG. 3e), consistent with the hypothesis that disrupting Stat3 signaling allows tumor cells to express physiologic danger signals capable of attracting and/or activating the cellular component of innate immunity. Blocking Stat3 signaling by an anti-sense Stat3 oligonucleotide in SCK1 tumors in vivo also led to heavy infiltration of macrophages and neutrophils (FIG. 3f).

Innate immunity critically impacts the development of adaptive immune responses (Janeway, C. A., Jr. 1989, Cold Spring Harb Symp Quant Biol 54: 1-13, Fearon et al., Science 272: 50-54, Medzhitov et al., 1997, Curr. Opin, Immunol. 9: 4-9, Kadowaki et al., 2000, J. Exp. Med. 192: 219-225), which involves the enhancement of antigen-presenting capacity of DCs induced in part by pro-inflammatory cytokines (Gallucci, 1999, Nature Med 5: 1429-1255, Mellman et al., 2001, Cell 106-255-258). Exposure of mature DCs to supernatants from Stat3β-transfected B16 cells resulted in an increased expression of IL-12, MHC Class II, CD86 and CD40 (FIG. 4). A five-fold induction of IL-12 production by DCs treated with Stat3β-transfected CT26 supernatant over control empty vector-transfected CT26 supernatant was also observed. Moreover, DCs exposed to supernatants derived from Stat3-interrupted tumor cells were far more potent in activating naïve antigen-specific T cells to proliferate and produce IL-2 (FIG. 4). Enhanced expression of the DC surface markers and T cell activation were also observed in experiments using supernatants derived from Stat3β-transfected CT26 tumor cells. These results indicate that the pro-inflammatory signals produced by Stat3-disrupted tumor cells could enhance APC function, leading to antigen-specific T cell responses. For the experiments shown in FIG. 4, bone marrow-derived progenitor cells were cultured in DC medium for 5 d followed by 2-day incubation in medium containing 50% supernatants derived from either non-transfected (WT), GFP or Stat3β-transfected B16 cells. The experiments shown in FIG. 4b were repeated using both plasmid and anti-sense oligonucleotide transfection with similar results.

Figure 5A:
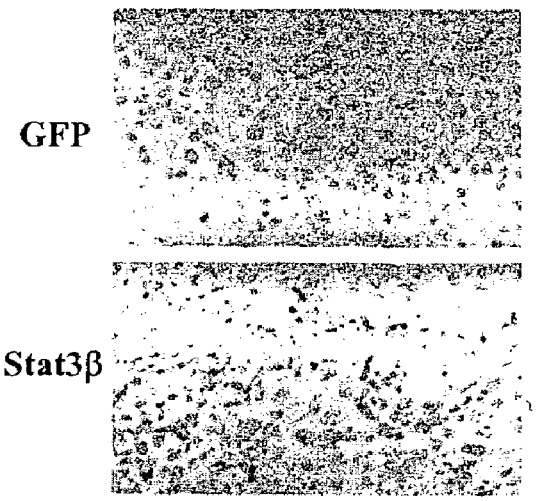
Figure 5B:
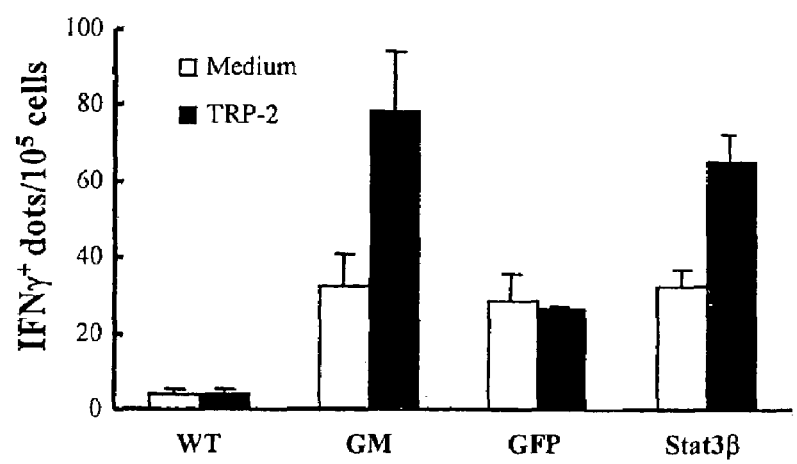

Applicants also investigated whether interrupting Stat3 signaling in tumor cells might cause in vivo activation of T cells, particularly tumor antigen-specific T cells. FIG. 5a shows that blocking Stat3 signaling in the B16 tumors in vivo. by Stat3β gene therapy led to tumor infiltration of T cells. The MHC class I H2-$K^b$ restricted tyrosinase-related protein 2 (TRP2)$_{181-188}$ peptide is recognized by B16 specific CD8+ T cells (Bloom, 1997, J. Exp Med 185: 453-459). To determine whether interrupting Stat3 signaling in tumor cells could lead to activation of tumor-specific CD8+ T cells in vivo, irradiated Stat3β-transfected B16 cells were injected s.c. into C57BL/6 mice. Splenocytes were isolated from these mice and ELISPOT was performed to detect TRP2-specific, IFNγ-producing CD8+ T cells. A significant increase of TRP2-specific IFNγ production was detected in splenocytes from mice that were injected with irradiated Stat3β-B16 cells but not from mice injected with irradiated control GFP-B16 cells (FIG. 5b). For the data shown in FIG. 5b splenocytes were prepared from mice injected with irradiated B16GM-CSF (GM), B16 cells transiently transfected with pIRES-EGFP. (GFP) or pIRES-Stat3β (Stat3β). Splenocytes were incubated in medium±TRP$_{181-188}$ peptide. TRP2-specific, IFNγ+ T cells induced by Stat3β-B16 cells were comparable to those induced by irradiated GM-CSF-transduced B16 cells, which have been shown to generate potent antitumor T cell immune responses, (Dranoff et al., 1993, Proc Natl Acad Sci USA 90: 3539-3543). Injection of Stat3-disrupted CT26 tumor cells was also able to activate a CT26 antigen (AH1)-specific T cell response in vivo at a level comparable to that of GM-CSF-transduced CT26 cells. These results demonstrate that disrupting constitutive Stat3 signaling in tumor cells leads to activation of tumor antigen-specific T cells in vivo.

Figure 5C:
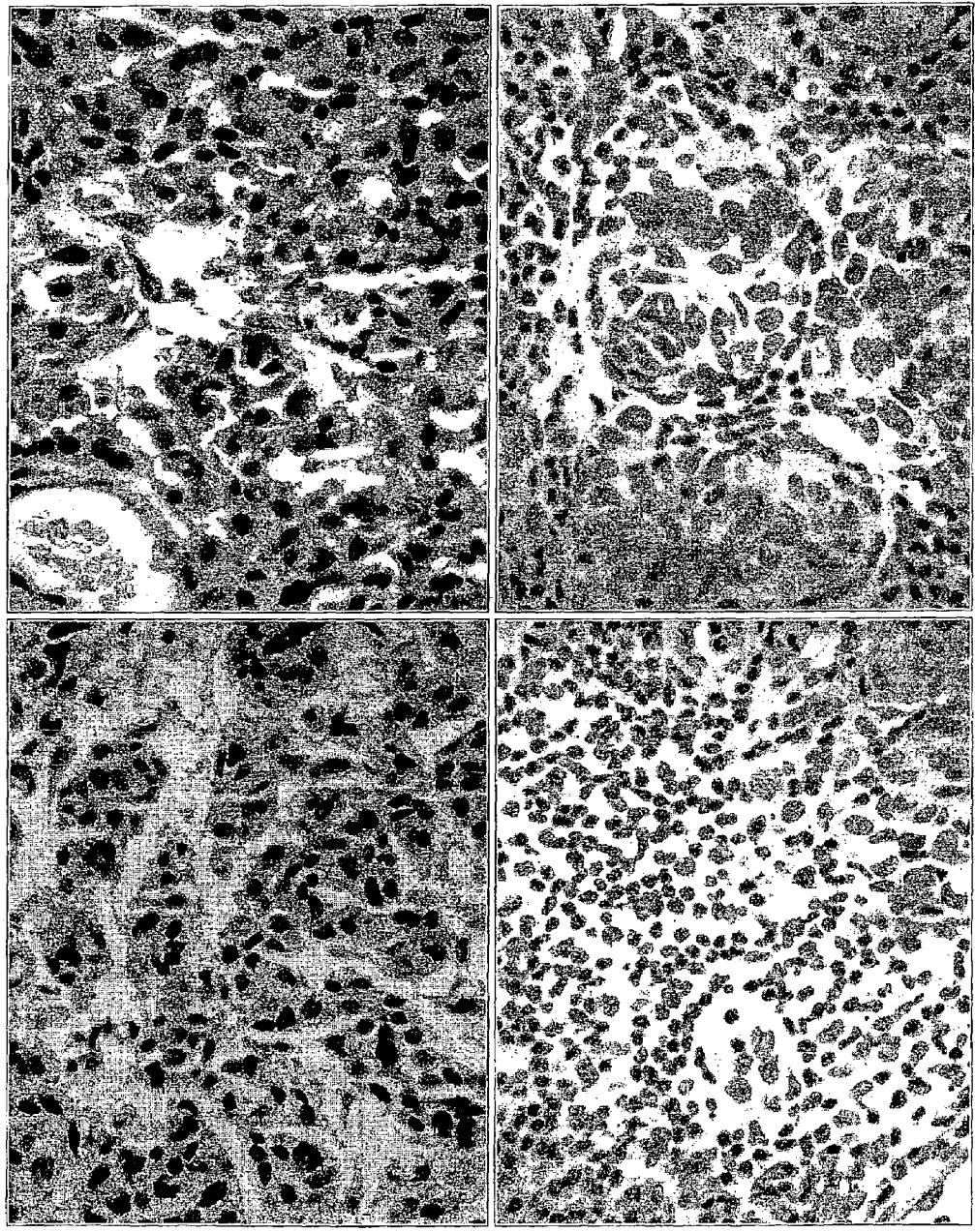

To investigate whether constitutively-activated Stat3 might have a role in human tumor immune evasion, Stat3 activity and infiltrating immune cells in surgically excised human melanoma specimens was coordinately analyzed, which display constitutively activated Stat3 at high frequency (Niu et al., 2002, Oncogene 21: 7001-7010). The results of these experiments showed that blocking Stat3 in human melanoma cells resulted in expression of pro-inflammatory cytokines and chemokines. Immunohistochemical staining of the melanoma specimens with a pY-Stat3 antibody that specifically detects activated Stat3 followed by computer morphometric analyses and quantification demonstrated a marked inverse correlation between pY-Stat3-positive tumor cells and tumor infiltrating lymphocytes (FIG. 5c,d). Taken together, these findings support the conclusion that Stat3 signaling in tumor negatively regulates anti-tumor immunity.

Figure 6A:
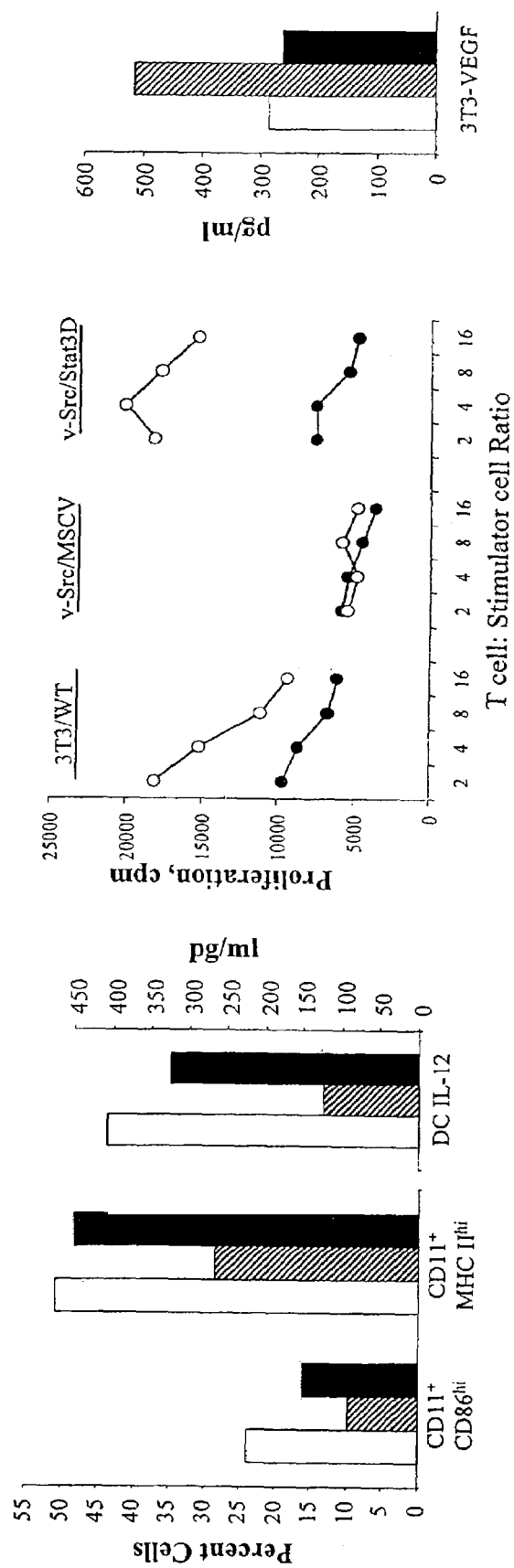

Taken together, the results described above indicate that blocking Stat3 in tumor cells allows them to produce pro-inflammatory mediators capable of activating mature DCs. Another mechanism whereby transformed cells could negatively modulate immune responses is by secreting factors that inhibit DC differentiation/maturation from progenitor cells (Gabrilvoich et al., 1996 Nature Med. 2:1096-1103, Gabrilvoich et al., 1998, Blood 92: 4150-4166). To investigate if transformation by constitutive Stat3 activity could induce the production of DC differentiation inhibitors, the Applicants first assessed the effects of v-Src transformation on DC differentiation. When transformed by v-Src, BALB/c 3T3 fibroblasts produced soluble factors that inhibited differentiation of DC from bone marrow progenitor cells, as indicated by a reduced proportion of CD11c$^+$MHC Class II$^{hi}$ CD86$^{hi}$ cells, and diminished IL-12 secretion (FIG. 6a). ELISA was used to determine DC production of IL-12. Interrupting Stat3 signaling in v-Src-transformed 3T3 cells by a Stat3 dominant-negative protein (Stat3D) (McLemore et al., 2001, Immunity 14: 193-204), inhibited Stat3 DNA-binding activity and blocked release of factors that inhibited DC maturation (FIG. 6a). Moreover, DC precursors maintained in culture containing 3T3v-Src supernatant had reduced ability to activate antigen-specific T cells, whereas blocking Stat3 signaling in v-Src-transformants reversed Src-induced inhibition of T cell activation (FIG. 6a).

Figure 6B:
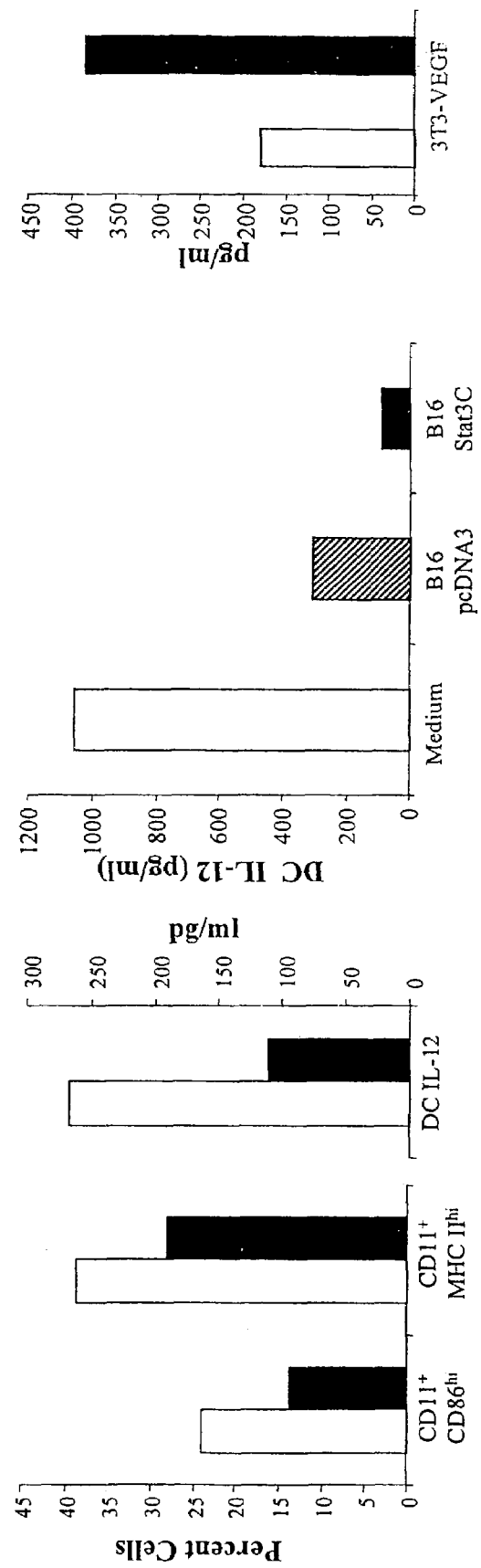

The ability of constitutively-activated Stat3 in promoting the production of factors that inhibit DC functional maturation was further demonstrated by enforcing expression of the constitutively-activated Stat3 mutant, Stat3C. As shown in FIG. 6b, expression of Stat3C induced the elaboration of factors that inhibited DC differentiation as demonstrated by a lowered proportion of CD11c$^+$CD86$^{hi}$ MHC class II$^{hi}$ DCs, and IL-12 production. The inverse correlation between Stat3 activity and DC functional maturation was further demonstrated with the B16 tumor model, which has moderate levels of endogenous Stat3 activity (Niu et al., 2002, Oncogene, supra; Niu et al., 1999, Cancer Res 59: 5059-5063). Culture with supernatants from B16 tumor cells reduced DC production of IL-12 (FIG. 6b). For the data shown in FIG. 6b, B16 tumor cells were transiently transfected with an empty control vector (pcDNA3) or a Stat3C expression vector. Progenitor cells were cultured for 8 days in DC medium supplemented with supernatants derived from indicated cell cultures prior to analyses, as indicated. Similar to previous studies demonstrating that enforced expression of Stat3C increased VEGF production in B16 tumor cells (Niu et al., 2002, Oncogene, supra), VEGF levels in 3T3/Stat3C cultures are higher than that of 3T3/MSCV as shown in the far right panel.

However, after transfecting a Stat3C expression vector, which increased Stat3 activity (Niu et al., 2002, Oncogene, supra). B16 supernatants caused stronger inhibition of DC production of IL-12 (FIG. 6b).

VEGF is a tumor-produced factor known to inhibit DC maturation (Gabrilovich et al. 1996; Nature Med. 2: 1096-1103, Gabrilovich et al., 1998, Blood 92: 4150-4166). Recent studies have shown that activated Stat3 is a direct activator of the VEGF promoter and enforcing Stat3C expression in B16 tumor cells increases VEGF expression (Niu et al, 2002, Oncogene, supra).

Figure 6C:
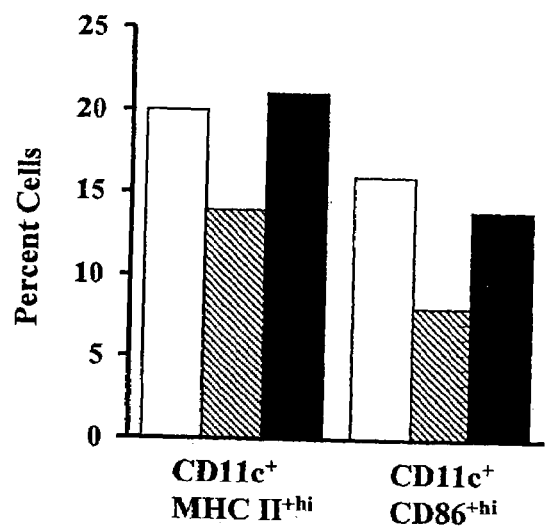
Figure 6D:
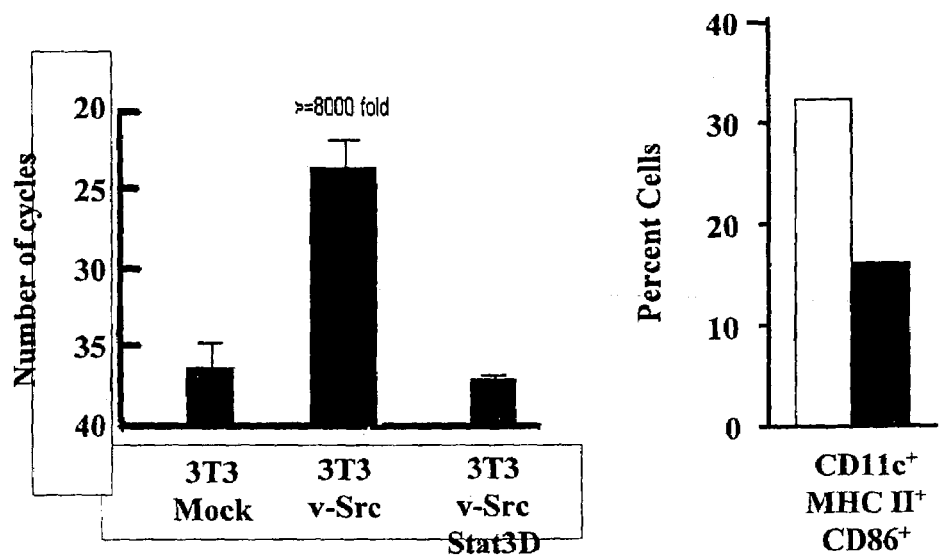
Figure 6E:
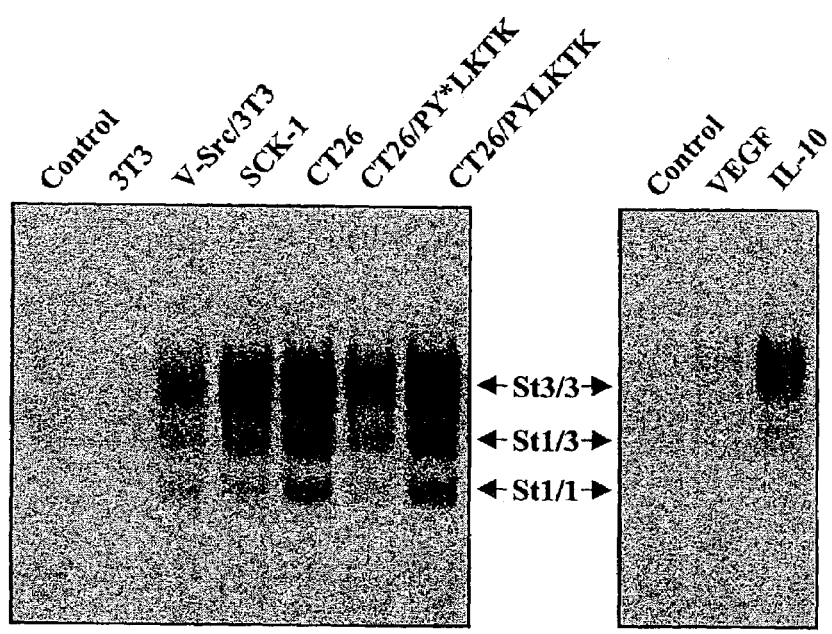
Figure 6F:
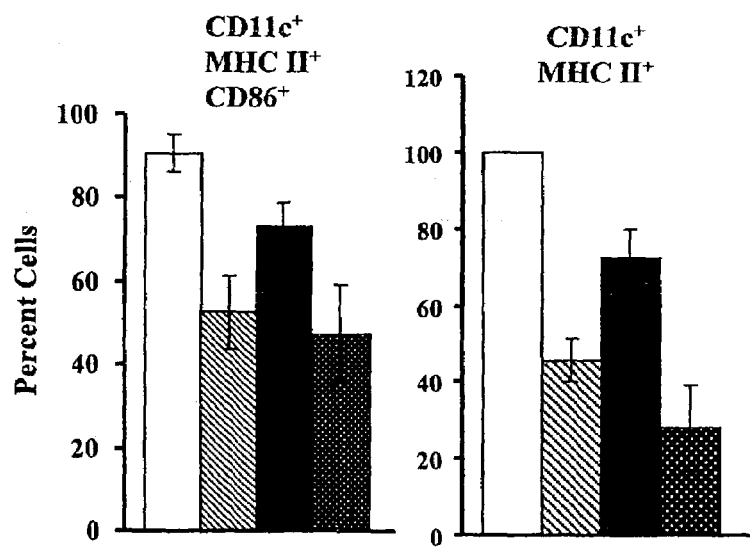

Depleting VEGF by neutralizing VEGF antibodies abrogated most of the inhibition of DC maturation induced by B16 supernatant (FIG. 6c). The proportion of mature functional DCs generated in culture supplemented with the various 3T3 supernatants was also inversely correlated with VEGF levels in these supernatants but VEGF neutralization had relatively little effect on inhibition of DC maturation induced by 3T3vSrc supernatant. These results are consistent with previous reports that VEGF is only one of multiple tumor-derived factors that inhibit DC differentiation. While several tumor-derived factors are capable of inhibiting DC maturation, the signaling pathways involved remain to be delineated. Since Stat3 signaling negatively regulates macrophage activity (Takeda et al., 1999, Immunity 10:39-49), we evaluated the role of Stat3 signaling in mediating inhibition of DC differentiation. We first analyzed whether tumor-derived factors can activate Stat3 in DC progenitors. FIG. 6d shows that supernatants from various tumor cell lines, and to a lesser extent recombinant VEGF, activate Stat3 in DC progenitors. In order to determine whether this activation directly affected DC maturation, we used a peptide inhibitor targeting activated STAT (Turkson et al., 2001, J. Biol. Chem. 276:45443-45455) to block Stat3 signaling in DC progenitor cells. Interrupting Stat3 signaling in DC progenitor cells abrogated tumor supernatant-induced inhibition of DC functional differentiation (FIG. 6d, e). Taken together, these findings support a model of propagated Stat3 signaling in which Stat3 activation in tumors induces the production of factors (one of which is VEGF) that in turn activate Stat3 in DC progenitors, thereby blocking their maturation.

Figure 6G:
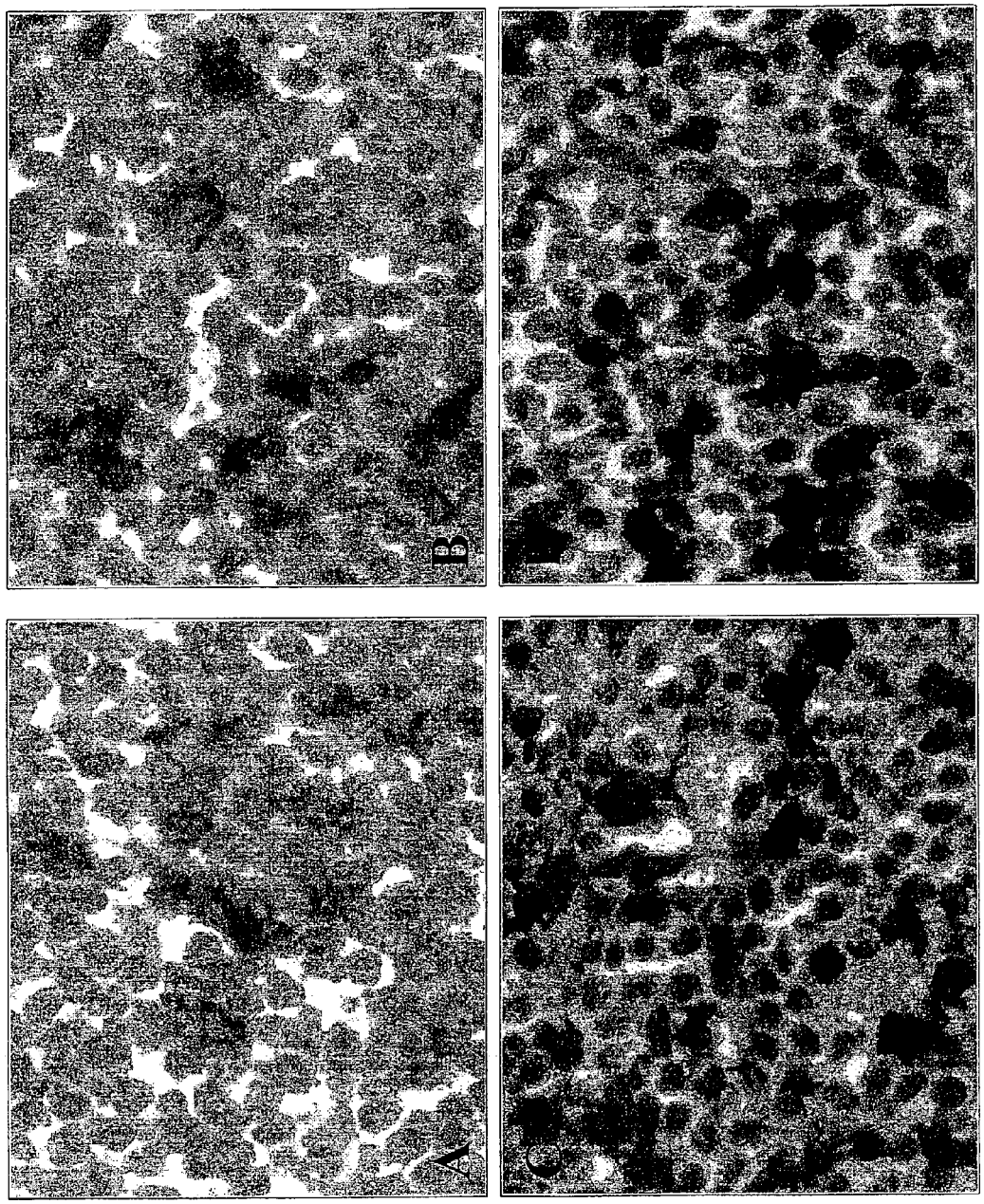

FIG. 6g shows an immunohistochemical analysis of tissue-sections from lymphnodes of melanoma patients. The sections were double labeled with CD1a$^+$ antibodies to visualize dendritic cells and with anti-phospho Stat3 antibodies to visualize activated Stat3 in nuclei. The two top panels show tissue samples free of tumor cells. Note the absence of activated Stat3 in the nuclei of the dendritic cells. The two bottom panels show tissue samples with tumor cells. Note the presence of activated Stat3 in the nuclei of the dendritic cells. These results demonstrate that the presence of tumor cells stimulates the activation of Stat3 in dendritic cells. The results support a model, wherein cell-surface bound signals or secreted factors from the tumor cells activate Stat3 in dendritic cells.

The results described above demonstrate that Stat3 activation in tumors blocks DC function both by inhibiting release of pro-inflammatory DC activators and inducing release of inhibitors of DC maturation. The results described above indicate that Stat3 activation in tumors blocks DC function both by inhibiting release of pro-inflammatory DC activators and inducing release of inhibitors of DC maturation. The proportion of mature functional DCs generated in culture supplemented with the various 3T3 supernatants was also inversely correlated with VEGF levels in these supernatants (far right panels of FIG. 6a,b). Collectively, the above results indicate that constitutive Stat3 signaling inducible by many oncogenic signaling pathways stimulates the elaboration of factors, including VEGF, that negatively modulates antitumor immune responses.

The foregoing examples identify a novel role for Stat3 signaling in tumor evasion of immune surveillance. While constitutive activation of Stat3 in tumor cells had been shown to up-regulate cell cycle regulatory and anti-apoptotic genes critical to the transformation process (Bowman et al., 2000, Oncogene 19, 2474-2488; Catlett-Falcone et al., 1999, Immunity 10, 105-115; Grandis et al., 2000, Proc Nat Acad Sci USA 97, 4227-4232, Bromberg, J. F., et al., 1999, Cell 98, 295-303; Bowman et al., 2001, Proc Nat Acad Sci USA 98: 7319-7324), its role in modulating interactions between tumor cells and the immune system has not been previously recognized. Indeed, recent studies in genetically-manipulated immunodeficient mice demonstrate that the immune system may act as an extrinsic suppressor of tumorigenesis (Kaplan et al., 1998, Immunology 95: 7556-7561; Shankaran et al., 2001, Nature 410, 1107). It is therefore logical that successful development of invasive, metastatic cancer would require the modulation of genes in a manner that inhibits activation of both innate and adaptive elements of the immune surveillance system. The Stat3 signaling pathway in tumor cells accomplishes this both by inhibiting the production of pro-inflammatory danger signals and by inducing the release of factors that inhibit DC functional maturation.

Stat3 signaling in tumor cells negatively regulates genes encoding various pro-inflammatory signals important for activating innate immune responses. Stat3 may also induce other tumor factors besides VEGF that are inhibitory to DC maturation. Previous studies showed that while neutralizing VEGF in tumor cell supernatants effectively abrogated inhibition of DC maturation, adding VEGF protein to DC cultures could only partially mimic the inhibitory effects of tumor cell supernatants (Gabrilovich et al., 1996, Nature Med. 2:1096-11031; Gabrilovich et al., 1998 Blood 92: 4150-4166), suggesting the involvement of other tumor-produced factors in inhibiting DC maturation. Further experiments will also be required to establish a causative role of Stat3 in tumor immune evasion. Nevertheless, while most of the previously described mechanisms by which established tumors evade immune recognition involve various components of the antigen processing and presentation machinery critical for effector T cells (Urban et al., 1982 J Exp Med 155: 557-573; Uyttenhove et al., 1983, J Exp Med. 157: 1040-1052; Wortzel et al., 1983 Nature 304: 165-167), this study underscores a critical role of innate immune response in initiation of tumor immunity. The examples also demonstrate that immune evasion occurs early during malignant progression, since activation of oncogenic tyrosine kinases is an early event in transformation leading to Stat3 activation, which negatively regulates anti-tumor immunity.

In conclusion, the foregoing examples support the methods encompassed by the present invention for interrupting Stat3 signaling with selective inhibitors and their use for treating cancer, suppressing growth of tumors, inducing apoptosis, and activating innate and adaptive anti-tumor immunity.

6.4 Co-Administration STAT3 Knockout Macrophages and Tumor Cells

B16 tumor cells were irradiated at 3500 rad. The macrophages were activated in a suspension with 2.5 µg/ml LPS for 5 hours and washed twice. Each mouse received 1×10$^6$ B16 or B16 GM-CSF tumor cells alone or in combination with 10$^6$ macrophages (LM as control or Stat3−/− macrophages) as indicated in Table 2. The challenge was performed with 2×10$^5$ live B16 tumor cells 5 days later.

TABLE 2

Percentage of B16 tumor in mice treated with different vaccination procedures

| days after challenge with B16 cells | B16 | B16 + LM | B16 + Stat3-/- | B16 GM-CSF | B16 GM-CSF + LM | B16 GM-CSF + Stat3-/- |
|---|---|---|---|---|---|---|
| 9 days | 75 | 50 | 50 | 25 | 25 | 0 |
| 23 days | 100 | 50 | 50 | 50 | 25 | 0 |

The presented data show that the co-administration of tumor cells with macrophages with decreased Stat3 activity is an effective vaccine against the formation and the growth of a cancer.

B16 tumor cells were irradiated at 400 rad. The macrophages were activated in a suspension with IFN-γ for 4 hours followed by LPS for 1.5 h. The concentrations for IFN-γ and for LPS, respectively, were in experiment (a) 4 U/mL IFN-γ; 100 ng/mL LPS and for experiment (b) 0.4 U/mL IFN-γ; 10 ng/mL LPS 2.5 μg/ml LPS. No washing procedure was applied. The cells were gently centrifuged and subsequently re-suspended in their own medium that was used during activation. Each mouse received $1\times10^6$ B16 or B16 GM-CSF tumor cells alone or in combination with $10^6$ macrophages (LM as control or Stat3-/- macrophages) as indicated in Table 3. The challenge was performed with $2\times10^5$ live B16 tumor cells 60 hours later.

TABLE 3

Percentage of B16 tumor in mice treated with different vaccination procedures

| days after challenge with B16 cells | B16 | B16 + LM (a) | B16 + Stat3-/- (a) | B16 GM-CSF | B16 GM-CSF + LM (a) | B16 GM-CSF + Stat3-/- (a) | B16 GM-CSF + Stat3-/- (b) |
|---|---|---|---|---|---|---|---|
| 3 days | 100 | 100 | 100 | 50 | 25 | 25 | 0 |
| 30 days | 100 | 100 | 100 | 100 | 100 | 100 | 25 |

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein, including patent applications, patents, and other publications, are incorporated by reference herein in their entireties for all purposes.

What is claimed is:

1. A method for treating cancer in a subject, said method comprising: (a) decreasing Stat3 expression or function in a tumor cell ; (b) culturing the tumor cells obtained in step (a); (c) contacting antigen-presenting cells with supernatant obtained from the culture of step (b), wherein the supernatant is irradiated before contacting the antigen-presenting cells with the supernatant; (d) contacting cytotoxic T cells with the antigen-presenting cells of step (c), thereby activating the cytotoxic T cells; and (e) administering the cytotoxic T cells to the subject, such that the cancer in the subject is treated.

2. The method of claim 1, wherein decreasing Stat3 expression or function comprises introducing dominant negative Stat3 to the tumor cells.

3. The method of claim 1, wherein decreasing Stat3 expression or function comprises expressing a dominant negative Stat3 gene in the tumor cells.

4. The method of claim 1, wherein decreasing Stat3 expression or function comprises administering Stat3-specific antisense nucleotide sequences to the tumor cells.

5. The method of claim 1, wherein decreasing Stat3 expression or function comprises introducing a mutation in the Stat3 gene of the tumor cells or deleting the Stat3 gene in the tumor cells.

6. The method of claim 1, wherein the cancer is selected from the group consisting of a fibrosarcoma, a myxosarcoma, a liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, an Ewing's tumor, a leiomyosarcoma, a rhabdomyosarcoma, a colon carcinoma, a pancreatic cancer, a breast cancer, an ovarian cancer, a prostate cancer, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a cervical cancer, a testicular tumor, a lung carcinoma, a small cell lung carcinoma, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a melanoma, a neuroblastoma, a retinoblastoma, an acute lymphocytic leukemia, an acute myelocytic leukemia, a chronic leukemia, a polycythemia vera, Hodgkin's disease, a non-Hodgkin's disease, a multiple myeloma, a Waldenstrom's macroglobulinemia, and a heavy chain disease.

7. The method of claim 1, wherein the cells are administered subcutaneously.

8. A method for stimulating dendritic cell differentiation, said method comprising: (a) decreasing Stat3 expression or function in tumor cells; (b) culturing the tumor cells of step (a) to produce a cell culture supernatant; and (c) treating dendritic cells with the supernatant of step (b), to obtain differentiated dendritic cells, wherein said cell culture supernatant is irradiated before treating said dendritic cells.

9. The method of claim 8, wherein decreasing Stat3 expression or function comprises introducing a dominant negative Stat3 into the tumor cells.

10. The method of claim 8, wherein decreasing Stat3 expression or function comprises expressing a dominant negative Stat3 gene in the tumor cells.

11. The method of claim 8, wherein decreasing Stat3 expression or function comprises introducing Stat3-specific antisense nucleotide sequences to the tumor cells.

12. The method of claim 8, wherein decreasing Stat3 expression or function comprises introducing a mutation in the Stat3 gene into the tumor cells or deleting the Stat3 gene in the tumor cells.

* * * * *

UNITED STATES PATENT AND TRADEMARK OFFICE
CERTIFICATE OF CORRECTION

PATENT NO. : 7,638,122 B2
APPLICATION NO. : 10/383707
DATED : December 29, 2009
INVENTOR(S) : Yu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1731 days.

Signed and Sealed this

Ninth Day of November, 2010

David J. Kappos
*Director of the United States Patent and Trademark Office*

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 1
actcaaactg ccctcctgct                                              20

<210> SEQ ID NO 2
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 2
tctgaagaaa ctgcttgatt                                              20

<210> SEQ ID NO 3
<211> LENGTH: 19
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 3
gccacaatcc gggcaatct                                               19

<210> SEQ ID NO 4
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 4
tggctgcagt ctgtagaagg                                              20

<210> SEQ ID NO 5
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 5
tttctgttct agatcctgca                                              20

<210> SEQ ID NO 6
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 6
tagttgaaat caaagtcatc                                              20

<210> SEQ ID NO 7
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

```
<400> SEQUENCE: 7
ttccattcag atcttgcatg                                                    20

<210> SEQ ID NO 8
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 8
tctgttccag ctgctgcatc                                                    20

<210> SEQ ID NO 9
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 9
tcactcacga tgcttctccg                                                    20

<210> SEQ ID NO 10
<211> LENGTH: 20
<212> TYPE: DNA
<213> ORGANISM: Artificial Sequence
<220> FEATURE:
<223> OTHER INFORMATION: antisense sequence used to inhibit translation
      of endogenous Stat3 mRNA

<400> SEQUENCE: 10
gagttttctg cacgtactcc                                                    20

<210> SEQ ID NO 11
<211> LENGTH: 6
<212> TYPE: PRT
<213> ORGANISM: artificial
<220> FEATURE:
<223> OTHER INFORMATION: description of artificial sequence: sequence
      used to inhibit activity of endogenous Stat3
<220> FEATURE:
<221> NAME/KEY: MOD_RES
<222> LOCATION: (2)..(2)
<223> OTHER INFORMATION: PHOSPHORYLATION

<400> SEQUENCE: 11

Pro Tyr Leu Lys Thr Lys
1               5

<210> SEQ ID NO 12
<211> LENGTH: 6
<212> TYPE: PRT
<213> ORGANISM: artificial
<220> FEATURE:
<223> OTHER INFORMATION: description of artificial sequence: control
      sequence used to measure activity of endogenous Stat3

<400> SEQUENCE: 12

Pro Tyr Leu Lys Thr Lys
1               5
```